(12) United States Patent
Valenzuela et al.

(10) Patent No.: US 7,964,576 B2
(45) Date of Patent: Jun. 21, 2011

(54) ANTI-ARTHROPOD VECTOR VACCINES, METHODS OF SELECTING AND USES THEREOF

(75) Inventors: Jesus G. Valenzuela, Rockville, MD (US); Yasmine Belkaid, Norwood, OH (US); Shaden Kamhawi, Rockville, MD (US); David Sacks, Silver Spring, MD (US); Jose M. C. Ribeiro, Rockville, MD (US)

(73) Assignee: The United States of America as represented by the Secretary of the Department of Health and Human Services, Bethesda, MD (US)

( * ) Notice: Subject to any disclaimer, the term of this patent is extended or adjusted under 35 U.S.C. 154(b) by 178 days.

(21) Appl. No.: 12/082,369

(22) Filed: Apr. 9, 2008

(65) Prior Publication Data

US 2009/0053255 A1 Feb. 26, 2009

Related U.S. Application Data

(62) Division of application No. 10/481,180, filed as application No. PCT/US02/19663 on Jun. 18, 2002, now Pat. No. 7,388,089.

(60) Provisional application No. 60/299,391, filed on Jun. 19, 2001.

(51) Int. Cl.
*A61K 48/00* (2006.01)
*A61K 38/00* (2006.01)
*C07H 21/04* (2006.01)
*C12N 15/00* (2006.01)

(52) U.S. Cl. ..... 514/44; 536/23.1; 536/23.7; 435/320.1; 424/184.1

(58) Field of Classification Search .................. None
See application file for complete search history.

(56) References Cited

U.S. PATENT DOCUMENTS 7,388,089 B2 * 6/2008 Valenzuela et al. .......... 536/23.7

OTHER PUBLICATIONS

Bowie et al (Science, 1990, 257:1306-1310).*
Houghten et al. (Vaccines, 1986, Edited by Fred Brown: Cold Spring Harbor Laboratory).*
Holmes, Exp. Opin.Invest. Drugs, 2001, 10(3):511-519).*
Greenspan et al (Nature Biotechnology, 1999, 7:936-937).*
Adler and Theodor, "The mouthparts, alimentary tract and salivary apparatus of the female *Phlebotomus papatasi*," *Ann. Trop. Med. Parasitol.* 20:109, 1926.
Barral et al., "Human immune response to sand fly salivary gland antigens: a useful epidemiological marker?" *Am. J. Trop. Med. Hyg.* 62(6):740-745, 2000.
Belkaid et al., "A natural model of *Leishmania major* infection reveals a prolonged "silent" phase of parasite amplification in the skin before the onset of lesion formation and immunity," *J. Immunol.* 165:969-977, 2000.

Belkaid et al., "Delayed-type hypersensitivity to *Phlebotomus papatasi* sand fly bite: an adaptive response induced by the fly?" *Proc. Natl. Acad. Sci. USA* 97:6704-6709, 2000.
Belkaid et al., "Development of a natural model of cutaneous leishmaniasis: powerful effects of vector saliva and saliva preexposure on the long-term outcome of *Leishmania major* infection in the mouse ear dermis," *J. Exp. Med.* 188:1941-1953, 1998.
Charlab et al., "Toward an understanding of the biochemical and pharmacological complexity of the saliva of a hematophagous sand fly *Lutzomyia longipalpis*," *Proc. Natl. Acad. Sci. USA* 26:15155-15160, 1999.
Gurunathan et al., "Vaccination with DNA encoding the immunodominant LACK parasite antigen confers protective immunity to mice infected with *Leishmania major*," *J. Exp. Med.* 186:1137-1147, 1997.
Gurunathan et al., "Vaccine requirements for sustained cellular immunity to an intracellular parasitic infection," *Nat. Med.* 4:1409-1415, 1998.
Kamhawi et al., "Protection against cutaneous leishmaniasis resulting from bites of uninfected sand flies," *Science* 290:1351-1354, 2000.
Katz et al., "Adenosine, AMP, and protein phosphatase activity in sand fly saliva," *Am. J. Trop. Med. Hyg.* 62:145-150, 2000.
Lerner et al., "Isolation of maxadilan, a potent vasodilatory peptide from the salivary glands of the sand fly *Lutzomyia longipalpis*," *J. Biol. Chem.* 266:11234-11236, 1991.
M. Lamine Mbow, *The Journal of Immunology*, 161:5571-5577, 1998.
Méndez et al., "The potency and durability of DNA- and protein-based vaccines against *Leishmania major* evaluated using low dose, intradermal challenge," *J. Immunol.* 166(8):5122-5128, 2001.
Modi and Tesh, "A simple technique for mass rearing *Lutzomyia longipalpis* and *Phlebotomus papatasi* (Diptera: Psychodidae) in the laboratory," *J. Med. Ent.* 20:568-569, 1983.
Qureshi et al., "Immunomodulatory properties of maxadilan, the vasodilator peptide from sand fly salivary gland extracts," *Am. J. Trop. Med. Hyg.* 54:665-671, 1996.
Ribeiro et al., "Blood-finding strategy of a capillary-feeding sand fly, *Lutzomyia longipalpis*," *Comp. Biochem. Physiol.* 83A:683-686, 1986.
Ribeiro et al., "Salivary apyrase activity of some Old World phlebotomine sand flies," *Insect Biochem.* 19:409-412, 1989.
Ribeiro et al., "Salivary glands of the sand fly *Phlebotomus papatasi* contain pharmacologically active amounts of adenosine and 5'-AMP," *J. Exp. Biol.* 202:1551-1559, 1999.
Sjölander et al., "Induction of a Th1 immune response and simultaneous lack of activation of a Th2 response are required for generation of immunity to leishmaniasis," *J. Immunol.* 160:3949-3957, 1998.

(Continued)

*Primary Examiner* — Patricia A Duffy
*Assistant Examiner* — Padma V Baskar
(74) *Attorney, Agent, or Firm* — Klarquist Sparkman, LLP.

(57) ABSTRACT

The present invention provides methods of selecting and uses of anti-arthropod vector vaccines to prevent Leishmaniasis. The present invention also provides compositions for vaccines to prevent Leishmaniasis.

14 Claims, 12 Drawing Sheets

OTHER PUBLICATIONS

Smelt et al., "B cell-deficient mice are highly resistant to *Leishmania donovani* infection, but develop neutrophil-mediated tissue pathology," *J. Immunol.* 164:3681-3688, 2000.

Theodos et al., "Analysis of enhancing effect of sand fly saliva on *Leishmania* infection in mice," *Infect. Immun.* 59:1592-1598, 1991.

Titus et al., "Salivary gland lysates from the sand fly *Lutzomyia longipalpis* enhanced *Leishmania* infectivity," *Science* 239:1306-1308, 1988.

Valenzuela et al., "The salivary apyrase of the blood-sucking sand fly *Phlebotomus papatasi* belongs to the novel *Cimex* family of apyrases," *J. Exp. Biol.* 204:229-237, 2001.

Valenzuela et al., "Toward a defined anti-Leishmania vaccine targeting vector antigens: characterization of a protective salivary protein," *The Journal of Experimental Medicine*, 194(3):331-342, 2001.

Volf et al., "Salivary proteins and glycoproteins in phlebotomine sandflies of various species, sex and age," *Medical and Veterinary Entomology*, 14(3):251-256, 2000.

Volf and Rohousova, "Species-specific antigens in salivary glands of phlebotomine sandflies," *Parasitology*, 122(1):37-41, 2001.

Waitumbi et al., *Infect. Immun.*, 66(4): 1534-1537, Apr. 1998.

Xu and Liew, "Protection against leishmaniasis by injection of DNA encoding a major surface glycoprotein, gp63, of *L. major*," *Immunology* 84:173-176, 1995.

\* cited by examiner

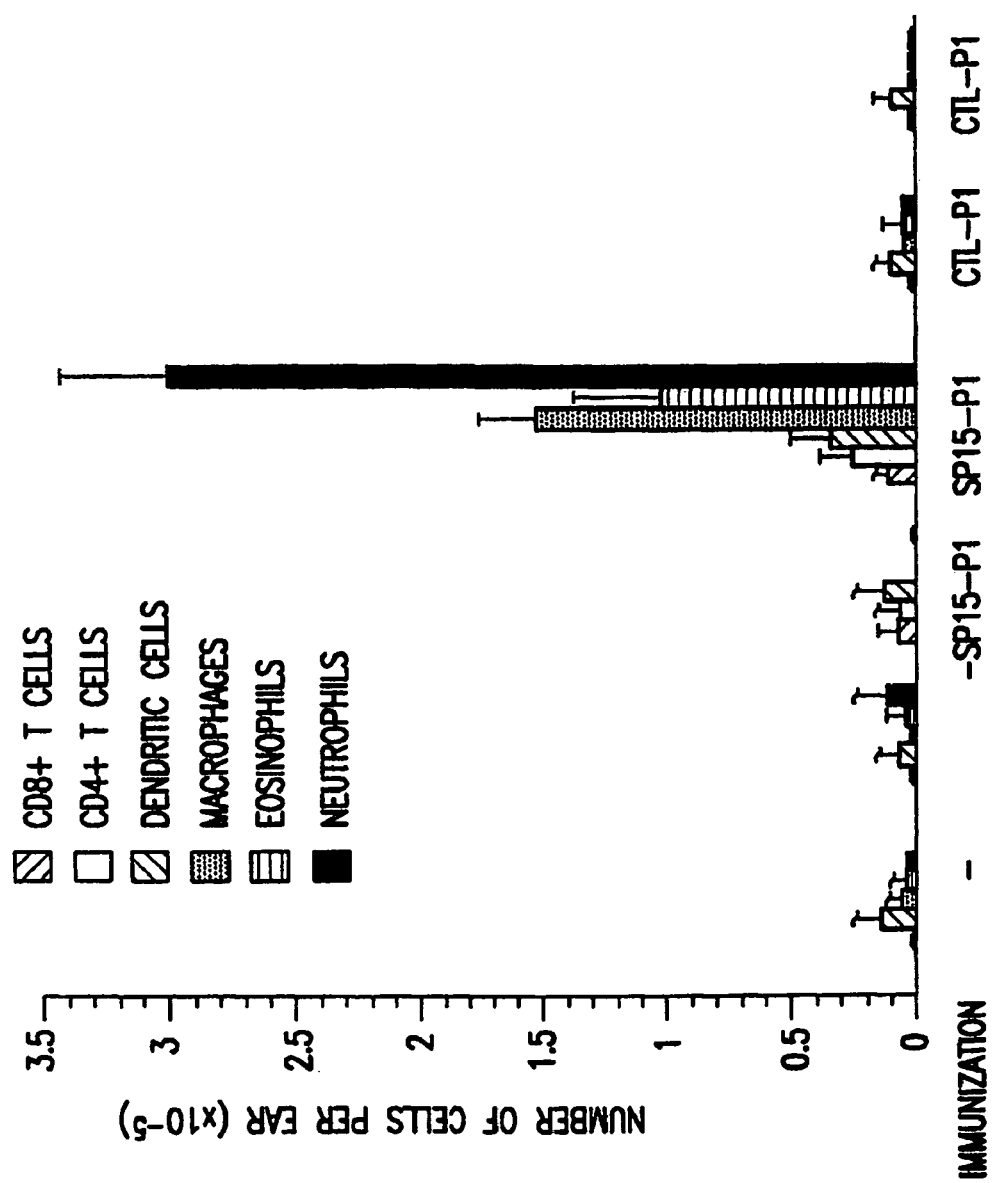

ANTI-ARTHROPOD VECTOR VACCINES, METHODS OF SELECTING AND USES THEREOF

CROSS REFERENCE TO RELATED APPLICATIONS

This application is a divisional of U.S. application Ser. No. 10/481,180, filed Dec. 17, 2003, now U.S. Pat. No. 7,388,089, issued Jun. 17, 2008, which is the U.S. National Stage of International Application No. PCT/US02/19663, filed Jun. 18, 2002, which was published in English under PCT Article 21(2), which in turn claims the benefit of U.S. Provisional Application No. 60/299,391, filed Jun. 19, 2001. The entire disclosure of each of these applications are incorporated by reference herein in their entirety.

FIELD OF THE INVENTION

The present invention relates to the field of vaccines for the prevention of infectious diseases. Specifically, the present invention relates to the methods of selecting and uses of anti-arthropod vector vaccines to prevent Leishmaniases.

INCORPORATION-BY-REFERENCE OF MATERIAL SUBMITTED ON COMPACT DISC

A Sequence Listing is provided in electronic format only on compact discs, as permitted under 37 CFR 1.52(e) and 1.821(c). The discs (copy 1 and copy 2) contain the file entitled "Sequence Listing.txt" (284 KB). The material on these discs is hereby incorporated by reference in its entirety.

BACKGROUND

The leishmaniases are a group of diseases caused by protozoa of the genus *Leishmania* and affect many millions of people worldwide. In humans, infection with the parasite manifests either as a cutaneous disease caused mainly by *L. major*, *L. tropica*, and *L. mexicana*; as a mucocutaneous disease caused mainly by *L. brasiliensis*; or as a visceral disease caused mainly by *L. donovani* and *L. chagasi*. All leishmanial diseases are transmitted to their vertebrate hosts by phlebotomine sand flies, which acquire the pathogen by feeding on infected hosts and transmit them by regurgitating the parasite at the site of a subsequent blood meal (1).

While obtaining a blood meal, sand flies salivate into the host's skin. This saliva contains anticlotting, antiplatelet, and vasodilatory compounds that increase the hemorrhagic pool where sand flies feed (2, 3). Some of these components are additionally immunomodulatory. For example, the New World sand fly *Lutzomyia longipalpis* contains the 6.5-kD peptide, maxadilan, which is the most potent vasodilator known (4). Maxadilan additionally has immunosuppressive activities of its own (5), as do many persistent vasodilators such as prostaglandin $E_2$ (6-8) and calcitonin gene-related peptide (9). Old World sand flies (who share a common ancestor with New World sand flies before the separation of the present tectonic plates, or about the time of irradiation of mammals) do not have maxadilan but instead use AMP and adenosine as vasodilators (10). Adenosine is also an immunomodulatory component, promoting the production of IL-10 and suppressing TNF-α and IL-12 in mice (11-13). Despite what is known about the role of sandfly saliva and disease transmission, much remains unknown, and an effective vaccine does not exist Thus, there is a need to prevent infection with the organisms that cause Leishmaniasis. The present invention provides nine major salivary proteins from the sand fly vector of *L. major, P. papatasi*, and the nucleic acids that encode them, a vaccine comprising the proteins and/or nucleic acids of the invention, and methods of producing an immune response in a subject to prevent Leishmaniasis.

SUMMARY OF THE INVENTION

The present invention provides an isolated nucleic acid, encoding a salivary polypeptide *Phlebotomus papatasi*.

The present invention also provides a nucleic acid that hybridizes under stringent conditions to the nucleic acids having SEQ ID NOS: 19-27.

The present invention provides a nucleic acid encoding a salivary polypeptide having the amino acid sequence of SEQ ID NOS: 10-18 .

Also provided by the present invention is an isolated salivary polypeptide of *Phlebotomus papatasi*.

The present invention provides an isolated salivary polypeptide having the N-terminal sequence of SEQ ID NOS: 1-9.

The present invention provides a salivary polypeptide having the amino acid sequence of SEQ ID NOS. 10-18.

The present invention also provides a vector comprising at least one nucleic acid or fragment thereof, selected from the group consisting of the nucleic acids having SEQ ID NOS: 19-27.

The present invention also provides a composition comprising at least one of the vectors and a pharmaceutically acceptable carrier.

The present invention provides a composition comprising at least one salivary polypeptide, or fragment thereof, selected from the group consisting of the polypeptides having SEQ ID NOS: 10-18 and a pharmaceutically acceptable carrier.

The present invention also provides a method of producing an immune response in a subject, comprising administering to the subject an effective amount of the various compositions of the invention.

The present invention also provides a method of preventing Leishmaniasis in a subject, comprising administering to the subject an effective amount of the various compositions of the invention.

*L. major* promastigotes alone (○) or in the presence of 0.5 pairs of SGH (●). Mice previously vaccinated on the right ear (2-wk intervals) with acrylamide alone, E (■) or mol wt range from 200 to 40 kD, A (♦); 39 to 20 kD, B (◇); or 19 to 3 kD, C (▲) were challenged in the left ear 2 wk following the last immunization with 500 *L. major* promastigotes in the presence of 0.5 pairs of SGH. The above symbols and bars represent the mean induration in mm±SB (5 mice per group) or the mean number of parasites per ear ±SE (4 mice per group). (*) indicate significance at $P<0.05$ when treatment curve (C) was compared with the acrylamide control (E).

Figure 3A:
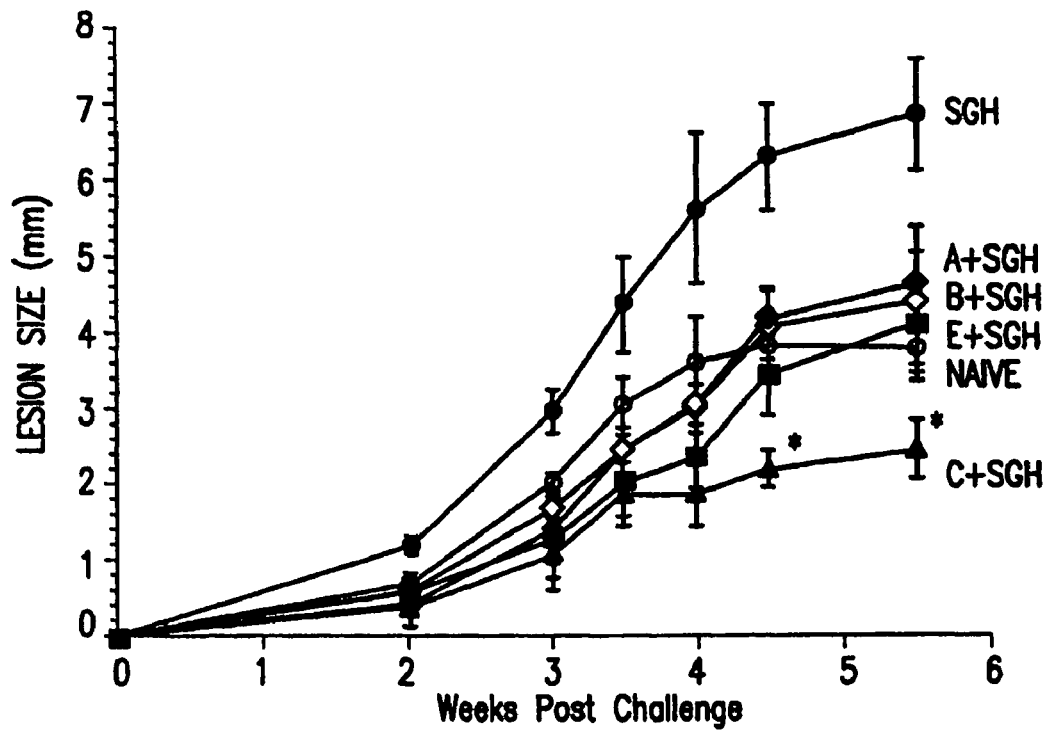
FIG. 3A shows the effect on the lesion size of mouse immunization with fractions of SGH separated by SDS-PAGE.
Figure 3B:
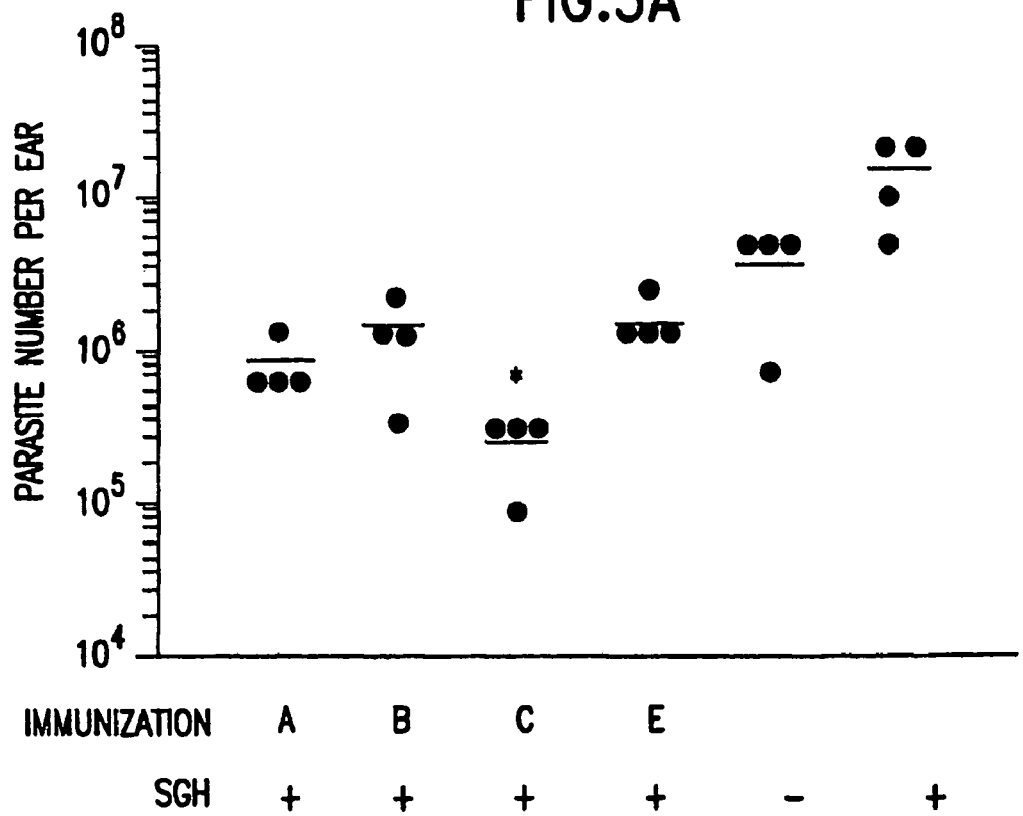
FIG. 3B shows the effect of mouse immunization and number of parasites 4.5wk post challenge following *L. major* infection. Naive mice were inoculated intradermally with 500
Figure 4:
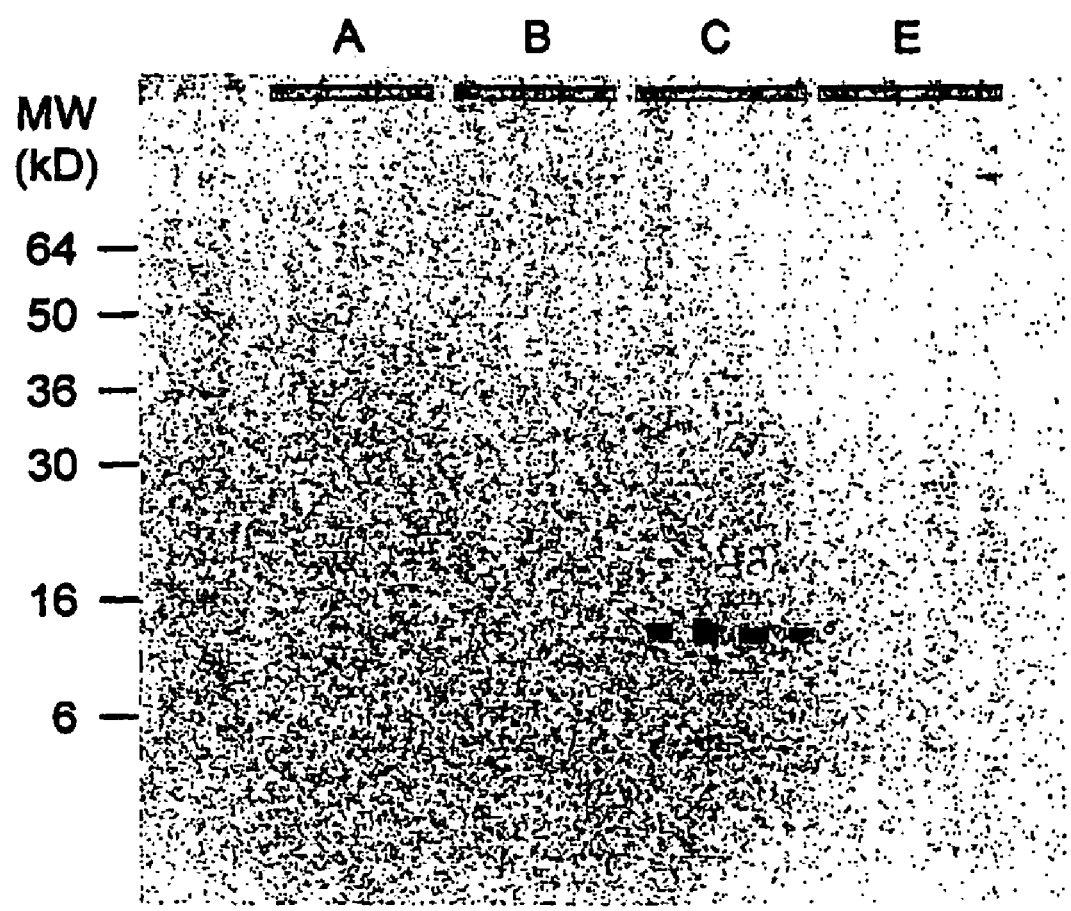

FIG. 4 shows Western blots of SGH of *P. papatasi* reacted with sera from mice immunized with polyacrylamide fractions separating the SGH by SDS-PAGE. Divisions were a high (A), medium (B), and low (C) mol wt region, as detailed in FIG. 3, or from control mice immunized with polyacrylamide (E), as shown.

Figure 5A:
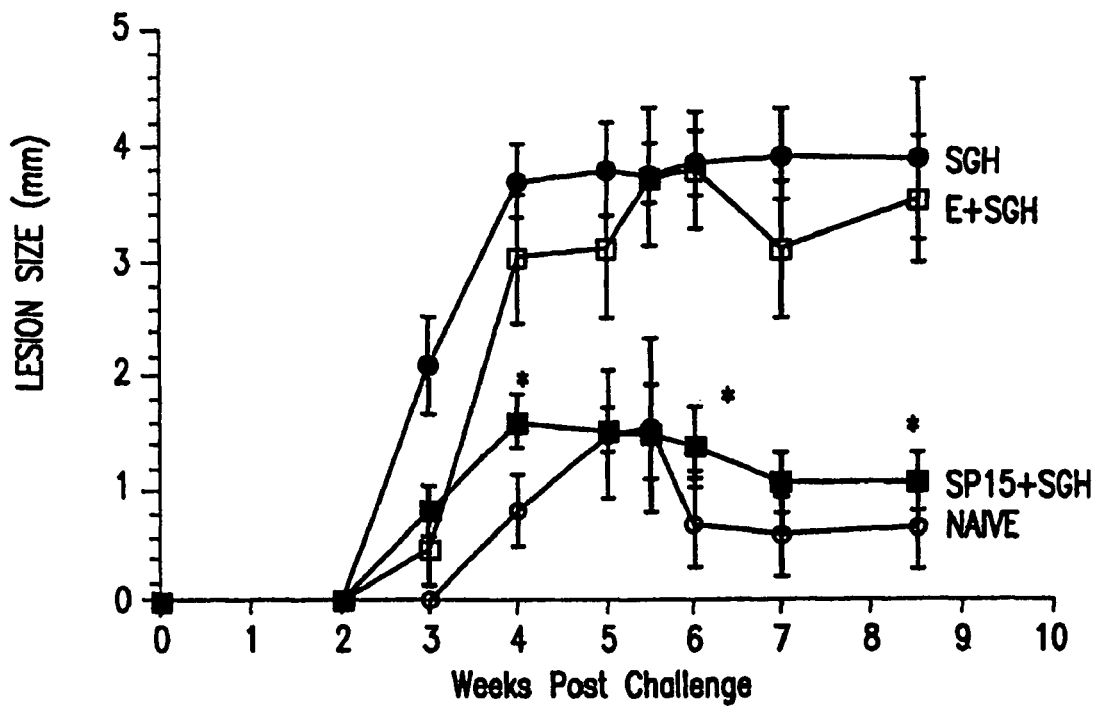

FIG. 5A shows the effect on the lesion size of mouse immunization with band SP15 from SDS-PAGE gels separating the SGH of *P. papatasi*.

Figure 5B:
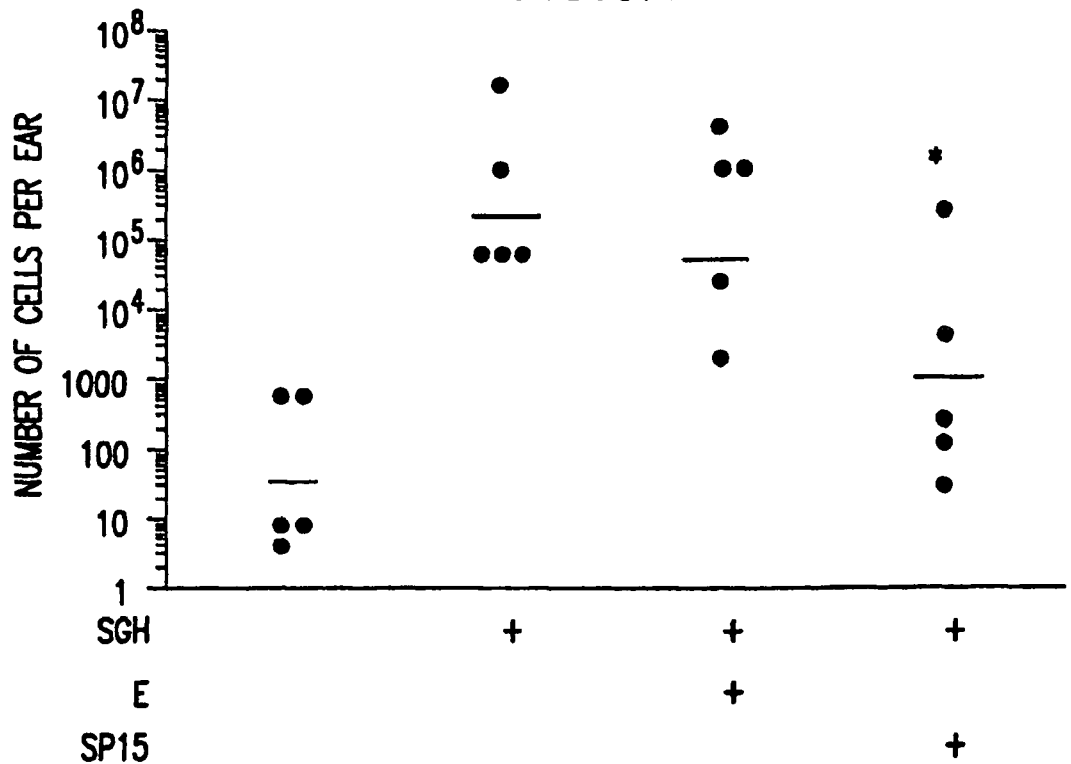

FIG. 5B shows the effect of mouse immunization with band SP15 from SDS-PAGE gels separating the SGH of *P. papatasi* on the number of parasites 9 wk post challenge following *L. major* infection. Naive mice were inoculated intradermally with 500 *L. major* promastigotes alone (○) or in the presence of 0.5 pairs of SGH (●). Mice previously vaccinated on the right ear (2-wk intervals) with acrylamide alone, E (□) or band SP15 (■) were challenged in the left ear 2 wk following the last immunization with 500 *L. major* promastigotes in the presence of 0.5 pairs of SGH. The above symbols and bars represent mean induration in mm±SE (5 mice per group) or mean number of parasites per ear±SE (5 mice per group), (*) indicate significance at $P<0.05$ when the treatment curve was compared with the acrylamide control.

Figure 6A:
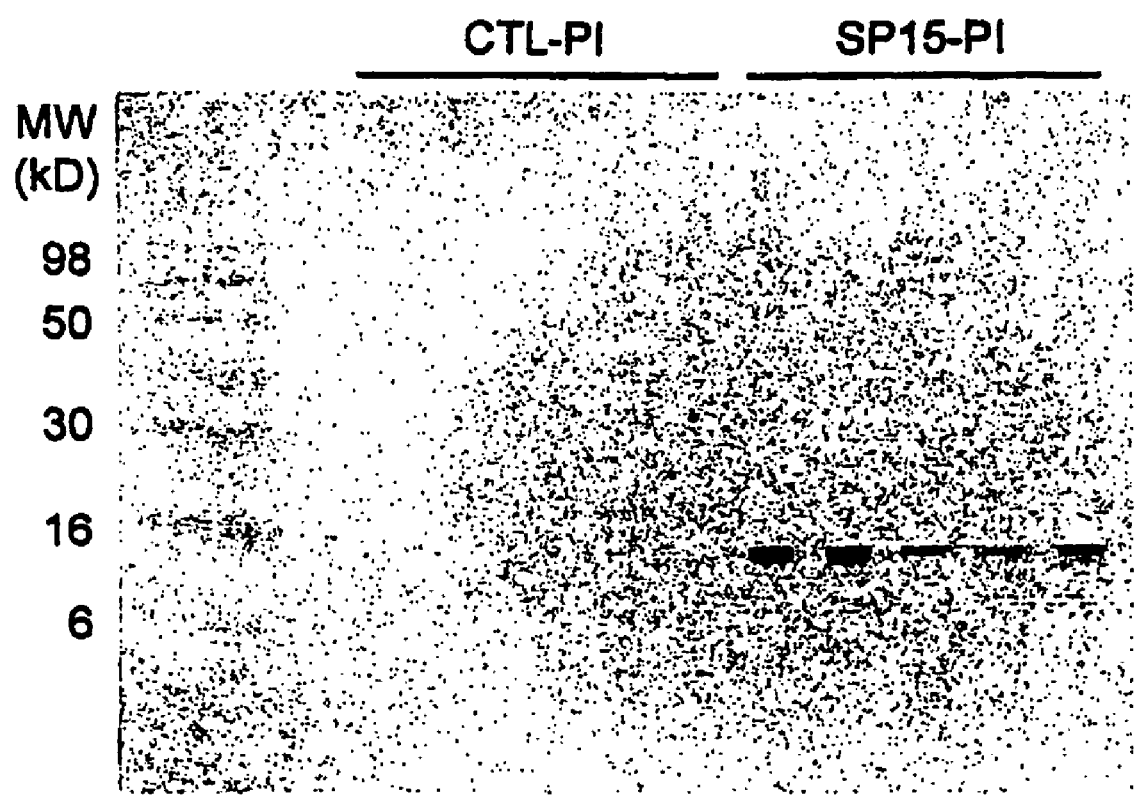

FIG. 6A shows that mouse humoral immunity is generated by injection of the VR1020 plasmid containing the SP15 sequence (SP15-PI). Western blots of salivary homogenates of *P. papatasi* reacted against sera of mice immunized twice in the right ear (2-wk interval) with 5 mg of the SP15-PI or control VR1020 plasmid (CTL-P1).

FIG. 6B shows that mouse cellular immunity is generated by injection of the VR1020 plasmid containing the SP15 sequence (SP15-PI). The DTH reaction was induced by sand fly bites on mice vaccinated with SP15-PI. The left ears of naive mice, mice immunized with SP15-PI, or control CTL-P1 mice were exposed to the bite of 10sand flies. Twenty-four hours later, the mice were sacrificed, and the inflammatory cells (neutrophils, eosinophils, macrophages, dendritic cells, $CD4^+$, and $CD8^+$ T cells) present in the dermis were analyzed. The symbols and bars represent the mean number of cellular subsets per ear ±SE; 7 mice per group.

Figure 7:
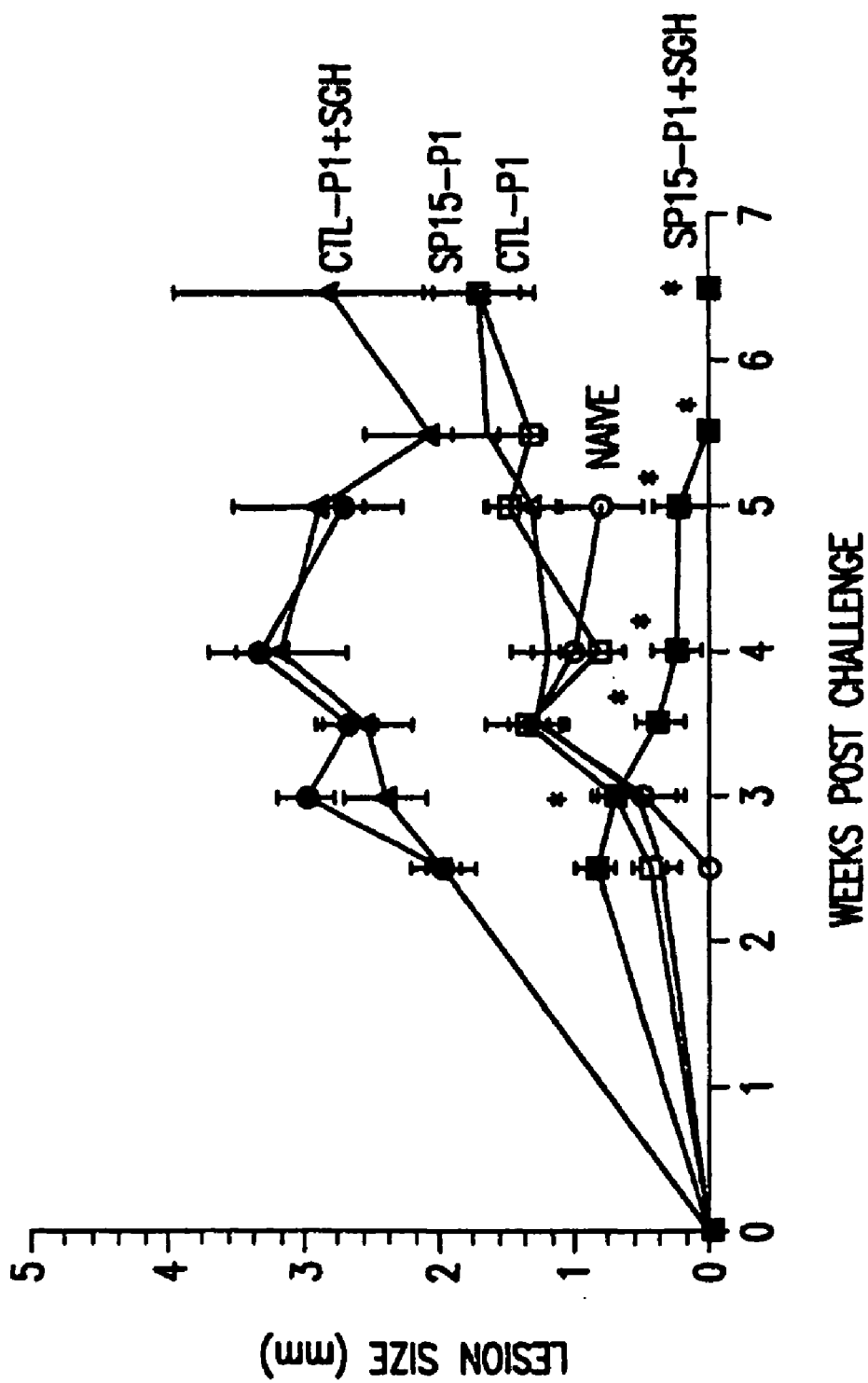

FIG. 7 shows the effect of mouse immunization with SP1S-P1 on the lesion size caused by *L. major* infection. Naive mice were inoculated intradermally with 500*L. major* promastigotes alone (○) or in the presence of 0.5 pairs of SGH (●). Mice previously vaccinated on the right ear (2-wk intervals) with SP15-P1 (□,■) or CTL-P1(△,▲) were challenged in the left ear 2 wk following the last immunization with 500 *L. major* promastigotes in the presence (■,▲) or not (□,△) of 0.5 pairs of SGH. The symbols and bars represent the mean induration in mm±1 SE; 5 mice per group. (*) indicate significance at $P<0.05$ when the treatment curve was compared with the control (CTL-P1+SGH).

Figure 8A:
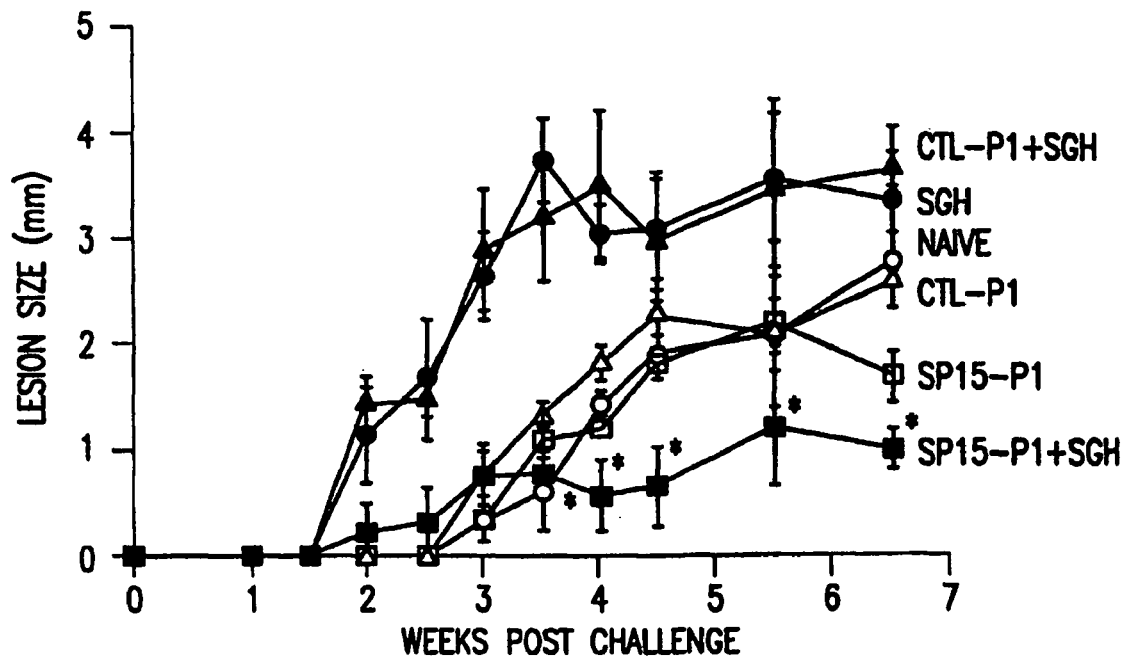

FIG. 8A shows the effect on lesion size and long-term effect of mouse immunization with SP15-PI on *L. major* infection. Naive mice were inoculated intradermally with 500 *L. major* promastigotes alone (○) or in the presence of 0.5 pairs of SGH (●). Mice previously vaccinated on the right ear (2-wk intervals) with SP15-PI (□,■) or CTL-PI (△, ▲) were challenged in the left ear 12 wk following the last immunization with 500 *L. major* promastigotes in the presence (■,▲) or not (□, △) of 0.5 pairs of SGH.

Figure 8B:
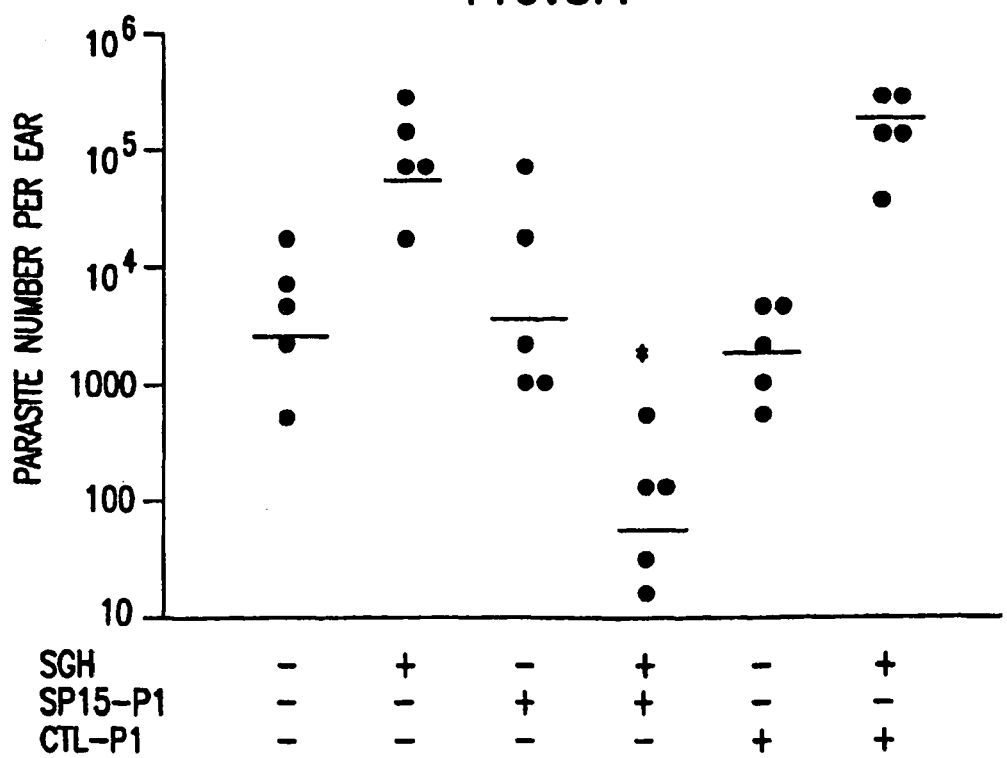

FIG. 8B shows the effect on parasite number and long-term effect of mouse immunization with SP 15-PI on *L. major* infection at 6.5 weeks post challenge. The symbols and bars represent the mean induration in mm±1 SE; 5 mice per group. (*) indicate significance at $P<0.05$ when the treatment curve was compared with the control (CTL-P1+ SGH).

Figure 9A:
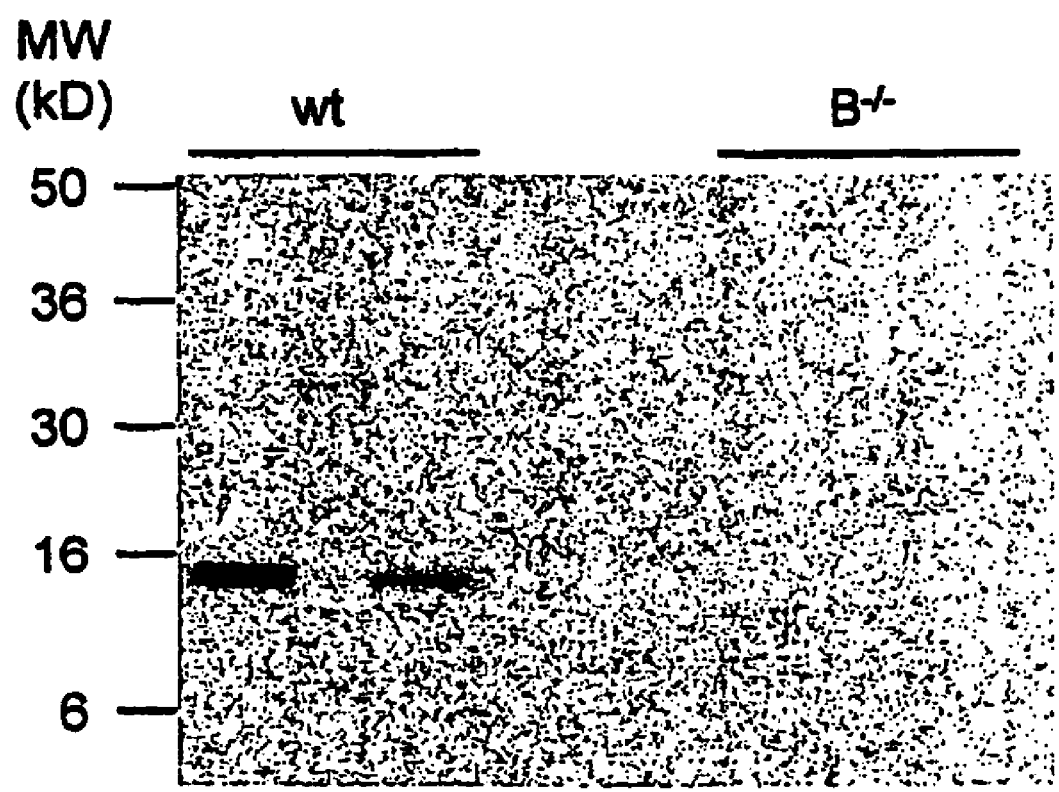

FIG. 9A shows the humoral response and DTH reaction oh $B^{-/-}$ and WT mice following vaccination with SP15-PI. Western blots showing antibody reactivity of WT but not mice against *P. papatasi* salivary homogenates are shown.

Figure 9B:
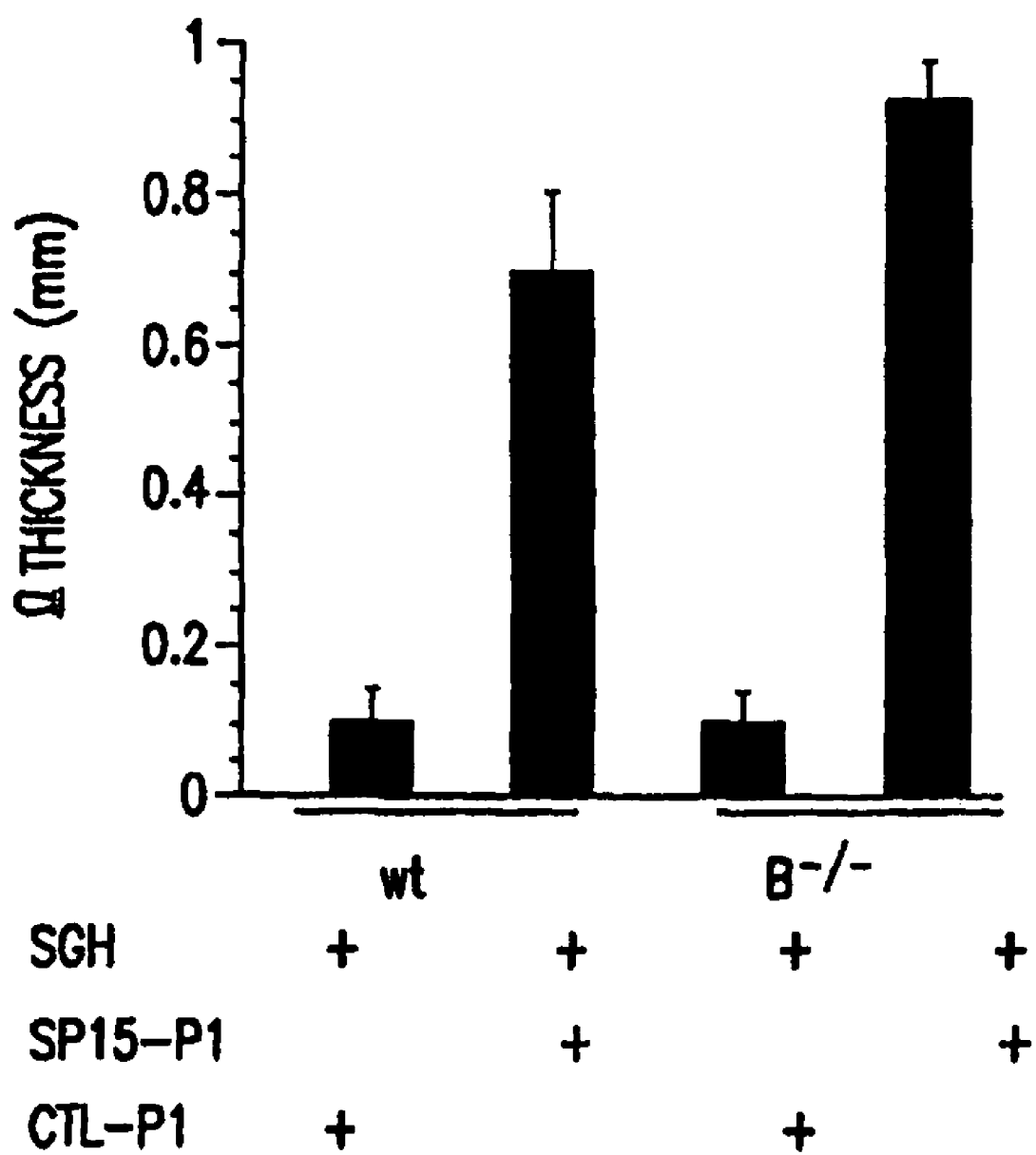

FIG. 9B shows measurements indicating the millimetric difference between the ear challenged with SGH and the non-inoculated ear, on $B^{-/-}$ and WT C57BL/10mice vaccinated with SP15-PI. Mice were immunized twice in the right ear (2-wk intervals) or not with 5 mg of SP15-PI or CTL-P1 and challenged in the left ear 2 wk after the last immunization with 500 *L. major* promastigotes in the presence of 0.5 pairs of SGH. Twenty-four h after inoculation, the ear thickness was measured and the difference between the ear thickness prior to challenge and 24 h after challenge was computed. Symbols and bars represent mean thickness in mm±SE; 5 mice per group.

Figure 10A:
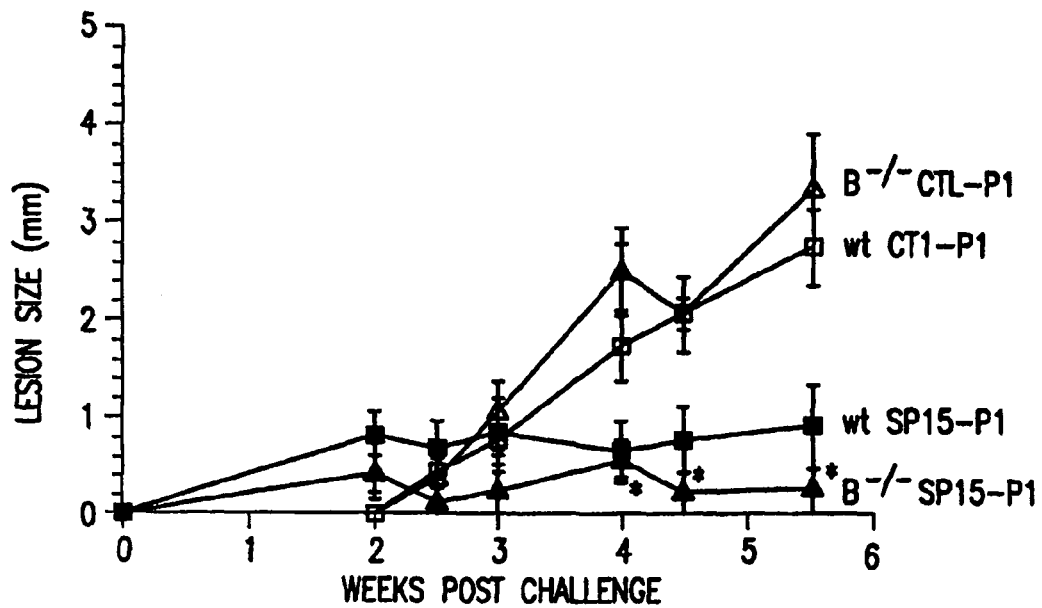

FIG. 10A shows lesion size progression and the role of DTH in mouse immunization with SP15-P1 on subsequent *L. major* infection. Bounce (△,▲) and their controls (C57BL/10, WT) (□,■), were immunized twice in the right ear (2-wk interval) with the VR1020 plasmid with (closed symbols) or without (open symbols), the SP15 sequence and challenged 2 wk later in the left ear with *L. major* promastigotes in combination with 0.5 pairs of homogenized *P. papatasi* salivary glands.

Figure 10B:
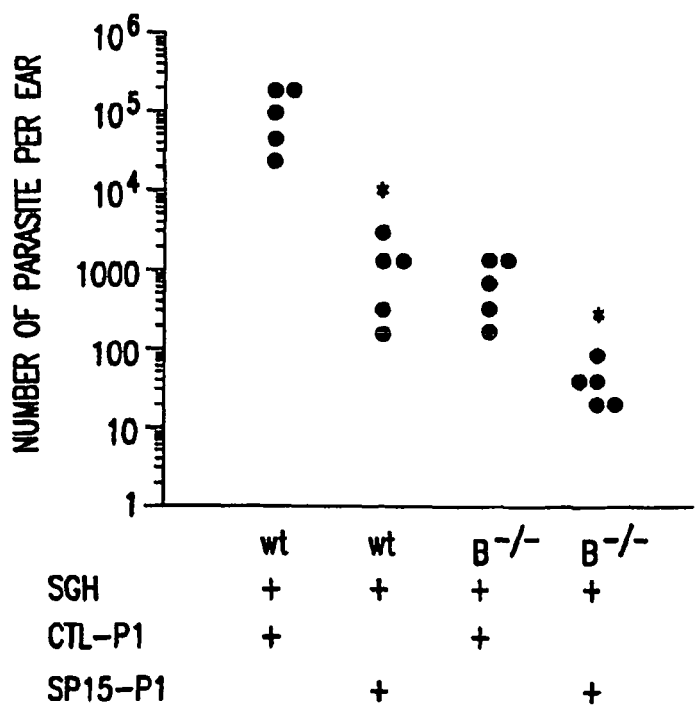

FIG. 10B shows the role of DTH in mouse immunization with SP15-PI on subsequent *L. major* infection and parasite numbers recovered from the lesion at 5.5 wk. Each number and bar represents the average ±SE of five mice. (*) indicates significance at $P<0.05$ when the number of parasites on the SP15-PI group was compared with the controls of the same mouse group.

DETAILED DESCRIPTION OF THE INVENTION

It must be noted that, as used in the specification and the appended claims, the singular forms "a," "an," and "the" include plural referents unless the context clearly dictates otherwise. Thus, for example, reference to "a nucleic acid" includes multiple copies of the nucleic acid and can also include more than one particular species of molecule.

The present invention provides an isolated salivary polypeptide of *Phlebotomus papatasi* (*P. papatasi*) and fragments thereof. An "isolated" polypeptide or fragment thereof of this invention is sufficiently free of contaminants or cell components with which polypeptides or fragments thereof normally occur and is present in such concentration as to be the only significant polypeptide or fragment thereof present in the sample. "Isolated" does not mean that the preparation is technically pure (homogeneous), but it is sufficiently pure to provide the polypeptide or fragment thereof in a form in which it can be used therapeutically.

A salivary polypeptide of *P. papatasi* is a polypeptide produced by the salivary glands of the sandfly and secreted into its saliva. As used herein, a "polypeptide" is a chain of amino acids which correspond to those encoded by a nucleic acid. A polypeptide usually describes a chain of amino acids having more than about 30 amino acids. A "fragment" is a specific part of a polypeptide having about 2 to about 30 amino acids. As used herein to describe an amino acid sequence (protein, polypeptide, peptide, etc.), "specific" means that the amino acid sequence is not found identically in any other source. The determination of specificity is made routine, because of the availability of computerized amino acid sequence databases, wherein an amino acid sequence of almost any length can be quickly and reliably checked for the existence of identical sequences. If an identical sequence is not found, the protein is "specific" for the recited source. The term "polypeptide" can refer to a linear chain of amino acids, or it can refer to a chain of amino acids which have been processed and folded into a functional protein. It is understood, however, that 30 is an arbitrary number with regard to distinguishing polypeptides and fragments. The polypeptides and fragments of the present invention are obtained by isolation and purification of the polypeptides and fragments from cells where they are produced naturally or by expression of exogenous nucleic acid encoding the polypeptide or fragment. The polypeptides and fragments of this invention can be obtained by chemical synthesis, by proteolytic cleavage of a polypeptide and/or by synthesis from nucleic acid encoding the polypeptides and fragments.

Examples of an isolated salivary polypeptide of *P. papatasi* include the polypeptides having the N-terminal sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9.

An example of the salivary polypeptide of the invention is the PpSP12 polypeptide. An example of the PpSP12 polypeptide is the PpSP12 polypeptide of *P. papatasi* having an approximate molecular weight of 12 kDa measured in SDS-PAGE under non-reducing conditions. The PpSP12 polypeptide also has an isoelectric point of 9.4.

A further example of the PpSP12 polypeptide is the polypeptide having the N-terminal sequence defined in SEQ ID NO:1. Additional examples of the PpSP12 polypeptide include the polypeptides having at least one of the amino acid sequences of SEQ ID NOS:28-92. A further example of the PpSP12 polypeptide is the polypeptide having the amino acid sequence of SEQ ID NO: 10.

An example of the salivary polypeptide of the invention is the PpSP14 polypeptide. An example of the PpSP14 polypeptide is the PpSP14 polypeptide of *P. papatasi* having an approximate molecular weight of 14 kDa measured in SDS-PAGE under non-reducing conditions. The PpSP14 polypeptide also has an isoelectric point of 8.61.

A further example of the PpSP14 polypeptide is the polypeptide having the N-terminal sequence defined in SEQ ID NO:2. Additional examples of the PpSP14 polypeptide include the polypeptides having at least one of the amino acid sequences of SEQ ID NOS:93-142. A further example of the PpSP14 polypeptide, is the polypeptide having the amino acid sequence of SEQ ID NO:11.

An example of the salivary polypeptide of the invention is the PpSP15 polypeptide. An example of the PpSP15 polypeptide is the PpSP15 polypeptide of *P. papatasi* having an approximate molecular weight of 15 kDa measured in SDS-PAGE under non-reducing conditions. The PpSP15 polypeptide also has an isoelectric point of 9.43.

A further example of the PpSP15 polypeptide is the polypeptide having the N-terminal sequence defined in SEQ ID NO:3. Additional examples of the PpSP15 polypeptide include the polypeptides having at least one of the amino acid sequences of SEQ ID NOS:143-207. A further example of the PpSP15 polypeptide is the polypeptide having the amino acid sequence of SEQ ID NO:12.

An example of the salivary polypeptide of the invention is the PpSP28 polypeptide. An example of the PpSP28 polypeptide is the PpSP28 polypeptide of *P. papatasi* having an approximate molecular weight of 28 kDa measured in SDS-PAGE under non-reducing conditions. The PpSP28 polypeptide also has an isoelectric point of 8.28.

A further example of the PpSP28 polypeptide is the polypeptide having the N-terminal sequence defined in SEQ ID NO:4. Additional examples of the PpSP28 polypeptide include the polypeptides having at least one of the amino acid sequences of SEQ ID NOS:208-310. A further example of the PpSP28 polypeptide is the polypeptide having the amino acid sequence of SEQ ID NO: 13.

An example of the salivary polypeptide of the invention is the PpSP30 polypeptide. An example of the PpSP30 polypeptide is the PpSP30 polypeptide of *P. papatasi* having an approximate molecular weight of 30 kDa measured in SDS-PAGE under non-reducing conditions. The PpSP30 polypeptide also has an isoelectric point of 9.11.

A further example of the PpSP30 polypeptide is the polypeptide having the N-terminal sequence defined in SEQ ID NO:5. Additional examples of the PpSP30 polypeptide include the polypeptides having at least one of the amino acid sequences of SEQ ID NOS:311-424. A further example of the PpSP30 polypeptide is the polypeptide having the amino acid sequence of SEQ ID NO:14.

An example of the salivary polypeptide of the invention is the PpSP32 polypeptide. An example of the PpSP32 polypeptide is the PpSP32 polypeptide of P. papatasi having an approximate molecular weight of 32 kDa measured in SDS-PAGE under non-reducing conditions. The PpSP32 polypeptide also has an isoelectric point of 9.26.

A further example of the PpSP32 polypeptide is the polypeptide having the N-terminal sequence defined in SEQ ID NO:6. Additional examples of the PpSP32 polypeptide include the polypeptides having at least one of the amino acid sequences of SEQ ID NOS:425-501. A further example of the PpSP32 polypeptide is the polypeptide having the amino acid sequence of SEQ ID NO: 15.

An example of the salivary polypeptide of the invention is the PpSP36 polypeptide. An example of the PpSP36 polypeptide is the PpSP36 polypeptide of P. papatasi having an approximate molecular weight of 36 kDa measured in SDS-PAGE under non-reducing conditions. The PpSP36 polypeptide also has an isoelectric point of 8.9.

A further example of the PpSP36 polypeptide is the polypeptide having the N-terminal sequence defined in SEQ ID NO:7. Additional examples of the PpSP36 polypeptide include the polypeptides having at least one of the amino acid sequences of SEQ ID NOS:502-633. A further example of the PpSP36 polypeptide is the polypeptide having the amino acid sequence of SEQ ID NO: 16.

An example of the salivary polypeptide of the invention is the PpSP42 polypeptide. An example of the PpSP42 polypeptide is the PpSP42 polypeptide of P. papatasi having an approximate molecular weight of 42 kDa measured in SDS-PAGE under non-reducing conditions. The PpSP42 polypeptide also has an isoelectric point of 9.01.

A further example of the PpSP42 polypeptide is the polypeptide having the N-terminal sequence defined in SEQ ID NO:8. Additional examples of the PpSP42 polypeptide include the polypeptides having at least one of the amino acid sequences of SEQ ID NOS:634-759. A further example of the PpSP42 polypeptide is the polypeptide having the amino acid sequence of SEQ ID NO: 17.

An example of the salivary polypeptide of the invention is the PpSP44polypeptide. An example of the PpSP44 polypeptide is the PpSP44 polypeptide of *P. papatasi* having an approximate molecular weight of 44 kDa measured in SDS-PAGE under non-reducing conditions. The PpSP44 polypeptide also has an isoelectric point of 8.70.

A further example of the PpSP44 polypeptide is the polypeptide having the N-terminal sequence defined in SEQ ID NO:9. Additional examples of the PpSP44 polypeptide include the polypeptides having at least one of the amino acid sequences of SEQ ID NOS:760-880. A further example of the PpSP44 polypeptide is the polypeptide having the amino acid sequence of SEQ ID NO: 18.

The present invention provides an antigenic or immunogenic fragment of the polypeptides of the invention. "Antigenic" when used herein means capable of binding specifically to an antibody. "Immunogenic" means capable of producing an immune response. The immune response can be humoral and/or cellular; specifically, the immune response can be characterized by the raising of antibodies directed to the antigen and/or characterized by delayed type hypersensitivity. Thus, the polypeptides and fragments thereof are immunoreactive. As used herein, "immunogenicity" means the ability of a molecule to generate an immune response in a host that reduces the severity of illness when the host is subsequently challenged with the same molecule.

An immunoreactive fragment has an amino acid sequence of at least about 5 consecutive amino acids of a salivary polypeptide amino acid sequence and binds an antibody. An antigenic fragment can be selected by applying the routine technique of epitope mapping to the polypeptides of the present invention to determine the regions of the proteins that contain epitopes reactive with serum antibodies or are immunogenic and capable of eliciting an immune response in an animal. Once the epitope is selected, an antigenic polypeptide containing the epitope can be synthesized directly, or produced recombinantly by cloning nucleic acids encoding the polypeptide in an expression system, according to the standard methods. Alternatively, an antigenic fragment of the antigen can be isolated from the whole antigen or a larger fragment by chemical or mechanical disruption. Fragments can also be randomly chosen from a known salivary polypeptide sequence and synthesized. Two or more fragments that are contiguous in a salivary polypeptide can be combined to form another fragment. The purified fragments thus obtained can be tested to determine their antigenicity and specificity by routine methods. A method of determining immunogenicity is provided in the Examples below.

Polypeptide fragments of the invention include fragments of PpSP12. The fragments can be antigenic or immunogenic fragments of the PpSP12 polypeptide defined by SEQ ID NO:10. Further examples of antigenic or immunogenic (immunoreactive) fragments of the PpSP12 polypeptide include the polypeptide-specific fragments identified in the sequence listing as SEQ ID NOS:28-92.

Polypeptide fragments of the invention include fragments of PpSP14. The fragments can be antigenic or immunogenic fragments of the PpSP14 polypeptide defined by SEQ ID NO:11. Further examples of antigenic or immunogenic (immunoreactive) fragments of the PpSP14 polypeptide include the polypeptide-specific fragments identified in the sequence listing as SEQ ID NOS:93-142.

Polypeptide fragments of the invention include fragments of PpSP15. The fragments can be antigenic or immunogenic fragments of the PpSP15 polypeptide defined by SEQ ED NO:12. Further examples of antigenic or immunogenic (immunoreactive) fragments of the PpSP15 polypeptide include the polypeptide-specific fragments identified in the sequence listing as SEQ ID NOS: 143-207.

Polypeptide fragments of the invention include fragments of PpSP28. The fragments can be antigenic or immunogenic fragments of the PpSP28 polypeptide defined by SEQ ID NO:13. Further examples of antigenic or immunogenic (immunoreactive) fragments of the PpSP28 polypeptide include the polypeptide-specific fragments identified in the sequence listing as SEQ ID NOS:208-310.

Polypeptide fragments of the invention include fragments of PpSP30. The fragments can be antigenic or immunogenic fragments of the PpSP30 polypeptide defined by SEQ ID NO:14. Further examples of antigenic or immunogenic (immunoreactive) fragments of the PpSP30 polypeptide include the polypeptide-specific fragments identified in the sequence listing as SEQ ID NOS:311-424.

Polypeptide fragments of the invention include fragments of PpSP32. The fragments can be antigenic or immunogenic fragments of the PpSP32 polypeptide defined by SEQ ID NO:15. Further examples of antigenic or immunogenic (immunoreactive) fragments of the PpSP32 polypeptide include the polypeptide-specific fragments identified in the sequence listing as SEQ ID NOS:425-501.

Polypeptide fragments of the invention include fragments of PpSP36. The fragments can be antigenic or immunogenic fragments of the PpSP36 polypeptide defined by SEQ ID NO:16. Further examples of antigenic or immunogenic (immunoreactive) fragments of the PpSP36 polypeptide include the polypeptide-specific fragments identified in the sequence listing as SEQ ID NOS:502-633.

Polypeptide fragments of the invention include fragments of PpSP42. The fragments can be antigenic or immunogenic fragments of the PpSP42 polypeptide defined by SEQ ID NO:17. Further examples of antigenic or immunogenic (immunoreactive) fragments of the PpSP42 polypeptide include the polypeptide-specific fragments identified in the sequence listing as SEQ ID NOS:634-759.

Polypeptide fragments of the invention include fragments of PpSP44. The fragments can be antigenic or immunogenic fragments of the PpSP44 polypeptide defined by SEQ ID NO:18. Further examples of antigenic or immunogenic (immunoreactive) fragments of the PpSP44 polypeptide include the polypeptide-specific fragments identified in the sequence listing as SEQ ID NOS:760-880.

Modifications to any of the above polypeptides or fragments can be made, while preserving the specificity and activity (function) of the native polypeptide or fragment thereof. As used herein, "native" describes a protein that occurs in nature. The modifications contemplated herein can be conservative amino acid substitutions, for example, the substitution of a basic amino acid for a different basic amino acid. Modifications can also include creation of fusion proteins with epitope tags or known recombinant proteins or genes encoding them created by subcloning into commercial or non-commercial vectors (e.g., polyhistidine tags, flag tags, myc tag, glutatbione-S-transferase [GST] fusion protein, xylE fusion reporter construct). Furthermore, the modifications contemplated will not affect the function of the polypeptide or the way the polypeptide accomplishes that function (e.g., its secondary structure or the ultimate result of the polypeptide's activity. These products are equivalent to the salivary polypeptides of the present invention. The means for determining these parameters are well known.

The present invention provides an isolated nucleic acid, encoding a salivary polypeptide of *Phlebotomus papatasi* (*P. papatasi*). "Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to the sequence which is naturally occurring or may include alternative codons which encode the same amino acid as that which is found in the naturally occurring sequence. Furthermore, nucleic acids may include codons which represent conservative substitutions of amino acids as are well known in the art Such nucleic acids can be used as probes and primers of the present invention.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids of the organism. The isolation of nucleic acids can therefore be accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The nucleic acid of this invention can be part of a recombinant nucleic acid construct comprising any combination of restriction sites and/or functional elements as are well known in the art which facilitate molecular cloning and other recombinant DNA manipulations. Thus, the present invention further provides a recombinant nucleic acid construct comprising a nucleic acid encoding a polypeptide or fragment thereof of this invention.

Salivary polypeptide-encoding nucleic acids can be isolated from an organism in which they are normally found (e.g., *P. papatasi*), using any of the routine techniques. For example, a genomic DNA or cDNA library can be constructed and screened for the presence of the nucleic acid of interest using one of the present salivary gland protein nucleic acids as a probe. Methods of constructing and screening such libraries are well known in the art and kits for performing the construction and screening steps are commercially available (for example, Stratagene Cloning Systems, La Jolla, Calif.). Once isolated, the nucleic acid can be directly cloned into an appropriate vector, or if necessary, can be modified to facilitate the subsequent cloning steps. Such modification steps are routine, an example of which is the addition of oligonucleotide linkers which contain restriction sites to the termini of the nucleic acid. General methods are set forth in Sambrook et al.

Salivary polypeptide-encoding nucleic acids can also be synthesized. For example, a method of obtaining a DNA molecule encoding a specific salivary polypeptide is to synthesize a recombinant DNA molecule which encodes the polypeptide. For example, oligonucleotide synthesis procedures are routine in the art and oligonucleotides coding for a particular protein region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. In the Examples below, another method for isolating the nucleic acids and fragments thereof is taught.

Examples of nucleic acids of the invention include those that encode a salivary polypeptide having the N-terminal sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9.

The present invention also provides a nucleic acid encoding a salivary polypeptide of *P. papatasi*, wherein the salivary polypeptide has the amino acid sequence selected from the group consisting of SEQ ID NO:10 (PpSP12), SEQ ID NO:11 (PpSP14), SEQ ID NO:12 (PpSP15), SEQ ID NO:13 (PpSP28), SEQ ID NO:14 (PpSP30), SEQ ID NO:15 (PpSP32), SEQ ID NO:16 (PpSP36), SEQ ID NO:17 (PpSP42) and SEQ ID NO:18 (PpSP44).

A nucleic acid that encodes a salivary polypeptide of the invention includes the nucleic acid that encodes PpSP12. A specific example of a nucleic acid that encodes PpSP12 is the nucleic acid of SEQ ED NO:19. The nucleotide sequence of PpSP12 is nucleotide 21 through 443.

A nucleic acid that encodes a salivary polypeptide of the invention includes the nucleic acid that encodes PpSP14. A specific example of a nucleic acid mat encodes PpSP14 is the nucleic acid of SEQ ID NO:20. The nucleotide sequence of PpSP 14 is nucleotide 15 through 444.

A nucleic acid that encodes a salivary polypeptide of the invention includes the nucleic acid that encodes PpSP15. A specific example of a nucleic acid mat encodes PpSP15 is the nucleic acid of SEQ ID NO:21. The nucleotide sequence of PpSP15 is nucleotide 18 through 446.

A nucleic acid that encodes a salivary polypeptide of the invention includes the nucleic acid that encodes PpSP28. A specific example of a nucleic acid that encodes PpSP28 is the nucleic acid of SEQ ID NO:22. The nucleotide sequence of PpSP28 is nucleotide 19 through 783.

A nucleic acid that encodes a salivary polypeptide of the invention includes the nucleic acid that encodes PpSP30. A specific example of a nucleic acid that encodes PpSP30 is the nucleic acid of SEQ ID NO:23. The nucleotide sequence of PpSP30 is nucleotide 29 through 790.

A nucleic acid that encodes a salivary polypeptide of the invention includes the nucleic acid that encodes PpSP32. A specific example of a nucleic acid that encodes PpSP32 is the nucleic acid of SEQ ID NO:24. The nucleotide sequence of PpSP32 is nucleotide 29 through 769.

A nucleic acid that encodes a salivary polypeptide of the invention includes the nucleic acid that encodes PpSP36. A specific example of a nucleic acid that encodes PpSP36 is the nucleic acid of SEQ ID NO:25. The nucleotide sequence of PpSP36 is nucleotide 43 through 1053.

A nucleic acid that encodes a salivary polypeptide of the invention includes the nucleic acid that encodes PpSP42. A specific example of a nucleic acid that encodes PpSP42 is the nucleic acid of SEQ ED NO:26. The nucleotide sequence of PpSP42 is nucleotide 25 through 1212.

A nucleic acid that encodes a salivary polypeptide of the invention includes the nucleic acid that encodes PpSP44. A specific example of a nucleic acid that encodes PpSP44 is the nucleic acid of SEQ ID NO:27. The nucleotide sequence of PpSP44 is nucleotide 23 through 1225.

Having provided and taught how to obtain a nucleic acid that encodes a salivary polypeptide, an isolated nucleic acid that encodes a fragment of a polypeptide is also provided. The fragment can be obtained using any of the methods applicable to the full gene. The fragment can encode a protein specific fragment (i.e., found in a salivary polypeptide, but not in other proteins) and/or a species-specific fragment (e.g., found in the salivary polypeptides of *P. papatasi*, but not in the salivary polypeptides of other species). Nucleic acids encoding protein-specific and/or species-specific fragments of salivary polypeptides are themselves gene-specific, species-specific or allele-specific fragments of the genes encoding the polypeptides and fragments of the present invention.

As used herein, a "fragment of a nucleic acid" is a specific part of a nucleic acid having at least about 6 nucleotides. As used herein to describe a nucleic acid sequence, "specific" means that the nucleic acid sequence is not found identically in any other source. The determination of specificity is made routine because of the availability of computerized nucleic acid sequence databases, wherein a nucleic acid sequence of almost any length can be quickly and reliably checked for the existence of identical i sequences. If an identical sequence is not found, the nucleic acid fragment is "specific" for the recited source.

A nucleic acid fragment of the invention can be a nucleic acid that encodes a fragment of PpSP12. The fragment can encode a polypeptide fragment specific for the polypeptide having the amino acid sequence of SEQ ID NO:10. A specific example of a fragment that encodes PpSP12 is the nucleic acid comprising nucleotides 81 through 137 of SEQ ID NO:19 that encodes the amino acid sequence of SEQ ID NO:1. Further examples of nucleic acid fragments of the invention include the nucleic acids that encode fragments of the PpSP12 polypeptide defined as SEQ ID NOS:28-92.

A nucleic acid fragment of the invention can be a nucleic acid that encodes a fragment of PpSP14. The fragment can encode a polypeptide fragment specific for the polypeptide having the amino acid sequence of SEQ ID NO:11. A specific example of a fragment that encodes PpSP14 is the nucleic acid comprising nucleotides 75 through 128 of SEQ ID NO:20 that encodes the amino acid sequence of SEQ ID NO:2. Further examples of nucleic acid fragments of the invention include the nucleic acids that encode fragments of the PpSP14 polypeptide defined as SEQ ID NOS:93-142.

A nucleic acid fragment of the invention can be a nucleic acid that encodes a fragment of PpSP15. The fragment can encode a polypeptide fragment specific for the polypeptide having the amino acid sequence of SEQ ID NO:12. A specific example of a fragment that encodes PpSP15 is the nucleic acid comprising nucleotides 78 through 134 of SEQ ID NO:21 that encodes the amino acid sequence of SEQ ID NO:3. Further examples of nucleic acid fragments of the invention include the nucleic acids that encode fragments of the PpSP15 polypeptide defined as SEQ ID NOS: 143-207.

A nucleic acid fragment of the invention can be a nucleic acid that encodes a fragment of PpSP28. The fragment can encode a polypeptide fragment specific for the i polypeptide having the amino acid sequence of SEQ ED NO:13. A specific example of a fragment that encodes PpSP28 is the nucleic acid comprising nucleotides 76 through 132 of SEQ ID NO:22 that encodes the amino acid sequence of SEQ ID NO:4. Further examples of nucleic acid fragments of the invention include the nucleic acids that encode fragments of the PpSP28 polypeptide defined as SEQ ID NOS:208-310.

A nucleic acid fragment of the invention can be a nucleic acid that encodes a fragment of PpSP30. The fragment can encode a polypeptide fragment specific for the polypeptide having the amino acid sequence of SEQ ID NO:14. A specific example of a fragment that encodes PpSP30 is the nucleic acid comprising nucleotides 86 through 133 of SEQ ID NO:23 that encodes the amino acid sequence of SEQ ID NO:5. Further examples of nucleic acid fragments of the invention include the nucleic acids that encode fragments of the PpSP30 polypeptide defined as SEQ ID NOS:311-424.

A nucleic acid fragment of the invention can be a nucleic acid that encodes a fragment of PpSP32. The fragment can encode a polypeptide fragment specific for the polypeptide having the amino acid sequence of SEQ ID NO:15. A specific example of a fragment that encodes PpSP32 is the nucleic acid comprising nucleotides 98 through 139 of SEQ ID NO:24 that encodes the amino acid sequence of SEQ ID NO:6. Further examples of nucleic acid fragments of the invention include the nucleic acids that encode fragments of the PpSP32 polypeptide defined as SEQ ID NOS:425-501.

A nucleic acid fragment of the invention can be a nucleic acid that encodes a fragment of PpSP36. The fragment can encode a polypeptide fragment specific for the polypeptide having the amino acid sequence of SEQ ID NO:16. A specific example of a fragment that encodes PpSP36 is the nucleic acid comprising nucleotides 106 through 162 of SEQ ID NO:25 that encodes the amino acid sequence of SEQ ID NO:7. Further examples of nucleic acid fragments of the invention include the nucleic acids that encode fragments of the PpSP36 polypeptide defined as SEQ ID NOS:502-633.

A nucleic acid fragment of the invention can be a nucleic acid that encodes a fragment of PpSP42. The fragment can encode a polypeptide fragment specific for the polypeptide having the amino acid sequence of SEQ ID NO:17. A specific example of a fragment that encodes PpSP42 is the nucleic acid comprising nucleotides 82 through 135 of SEQ ID NO:26 that encodes the amino acid sequence of SEQ ID NO:8. Further examples of nucleic acid fragments of the invention include the nucleic acids that encode fragments of the PpSP42 polypeptide defined as SEQ ID NOS:634-759.

A nucleic acid fragment of the invention can be a nucleic acid that encodes a fragment of PpSP44. The fragment can encode a polypeptide fragment specific for the polypeptide having the amino acid sequence of SEQ ED NO:18. A specific example of a fragment that encodes PpSP44 is the nucleic acid comprising nucleotides 77 through 136 of SEQ ID NO:27 that encodes the amino acid sequence of SEQ ID NO:9. Further examples of nucleic acid fragments of the invention include the nucleic acids that encode fragments of the PpSP44 polypeptide defined as SEQ ID NOS:760-880.

The present invention provides a nucleic acid of at least 10 nucleotides that hybridizes under stringent conditions to the nucleic acids that encode the salivary polypeptides and fragments of the present invention. For example, the conditions can be polymerase chain reaction conditions and the hybridizing nucleic acid can be a primer consisting of a specific fragment of the reference sequence or a nearly identical nucleic acid that hybridizes only to the exemplified salivary polypeptide gene or a homolog thereof.

The invention provides an isolated nucleic acid that specifically hybridizes with the salivary polypeptide-encoding genes shown in the sequence set forth as SEQ ID NOS:19-27 under the conditions of about 16 hrs at about 65° C., about 5× SSC, about 0.1% SDS, about 2× Denhardt's solution, about 150 µg/ml salmon sperm DNA with washing at about 65° C., 30 min, 2×, in about 0.1× SSPE/0.1% SDS. Alternative hybridization conditions include 68° C. for about 16 hours in buffer containing about 6× SSC, 0.5% sodium dodecyl sulfate, about 5× Denhardt's solution and about 100 μg salmon sperm DNA, with washing at about 60° C. in about 0.5× SSC. For example, the hybridizing nucleic acid can be a probe that hybridizes only to the exemplified salivary polypeptide gene or a homolog thereof. Thus, the hybridizing nucleic acid can be a naturally occurring homolog of the exemplified genes. The hybridizing nucleic acid can also include insubstantial base substitutions that do not prevent hybridization under the stated conditions or affect the function of the encoded protein, the way the protein accomplishes that function (e.g., its secondary structure or the ultimate result of the protein's activity. The means for determining these parameters are well known.

As used herein to describe nucleic acids, the term "selectively hybridizes" excludes the occasional randomly hybridizing nucleic acids as well as nucleic acids that encode other known homologs of the present polypeptides. The selectively hybridizing nucleic acids of the invention can have at least 70%, 73%, 78%, 80%, 85%, 88%, 90%, 91%, 92%, 93%, 94%, 95%, 96%, 97%, 98% and 99% complementarity with the segment and strand of the sequence to which it hybridizes. The nucleic acids can be at least 10, 18,20,25, 50,100, 150, 200,300, 500, 550,750, 900, 950, or 1000 nucleotides in length, depending on whether the nucleic acid is to be used as a primer, probe or for protein expression. Thus, the nucleic acid can be an alternative coding sequence for the protein, or can be used as a probe or primer for detecting the presence of a salivary polypeptide-encoding nucleic acid or obtaining such polypeptide. If used as primers, the invention provides compositions including at least two nucleic acids which selectively hybridize with different regions so as to amplify a desired region. Depending on the length of the probe or primer, it can range between 70% complementary bases and full complementarity and still hybridize under stringent conditions. For example, for the purpose of diagnosing the presence of a salivary polypeptide-encoding nucleic acid, the degree of complementarity between the hybridizing nucleic acid (probe or primer) and the sequence to which it hybridizes (DNA from a sample) should be at least enough to exclude hybridization with a nucleic acid from a related organism. The invention provides examples of these nucleic acids so that the degree of complementarity required to distinguish selectively hybridizing from nonselectively hybridizing nucleic acids under stringent conditions can be clearly determined for each nucleic acid. It should also be clear that the hybridizing nucleic acids of the invention will not hybridize with nucleic acids encoding unrelated proteins (hybridization is selective) under stringent conditions. "Stringent conditions" refers to the washing conditions used in a hybridization protocol. In general, the washing conditions should be a combination of temperature and salt concentration chosen so that the denaturation temperature is approximately 5-20° C. below the calculated $T_m$ of the hybrid under study. The temperature and salt conditions are readily determined empirically in preliminary experiments in which samples of reference DNA immobilized on filters are hybridized to the probe or protein coding nucleic acid of interest and then washed under conditions of different stringencies. For example, MgCl2 concentrations used in PCR buffer can be altered to increase the specificity with which the primer binds to the template, but the concentration range of this compound used in hybridization reactions is narrow, and therefore, the proper stringency level is easily determined. For example, hybridizations with oligonucleotide probes 18 nucleotides in length can be done at 5-10° C. below the estimated $T_m$ in 6× SSPE, then washed at the same temperature in 2× SSPE. The $T_m$ of such an oligonucleotide can be estimated by allowing 2° C. for each A or T nucleotide, and 4° C. for each G or C. An 18 nucleotide probe of 50% G+C would, therefore, have an approximate $T_m$ of 54° C. Likewise, the starting salt concentration of an 18 nucleotide primer or probe would be about 100-200 mM. Thus, stringent conditions for such an 18 nucleotide primer or probe would be a Tm of about 54° C. and a starting salt concentration of about 150 mM and modified accordingly by preliminary experiments. $T_m$ values can also be calculated for a variety of conditions utilizing commercially available computer software (e.g., OLIGO®).

Once a nucleic acid encoding a particular polypeptide of interest, or a region of that nucleic acid, is constructed, modified, or isolated, that nucleic acid can then be cloned into an appropriate vector, which can direct the in vivo or hi vitro synthesis of that wild-type and/or modified polypeptide. The vector is contemplated to have the necessary functional elements that direct and regulate transcription of the inserted gene, or hybrid gene. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al). Thus, the nucleic acids of the present invention can be in a vector, and the vector can be in a host for expressing the nucleic acid.

The present invention provides a vector comprising at least one nucleic acid or fragment thereof encoding a polypeptide or fragment thereof of this invention. The vector can be an expression vector which contains all of the generic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, vaccinia virus, adenovirus, retrovirus and/or adeno-associated virus nucleic acid. The nucleic acid or vector of this invention can also be in a liposome or a delivery vehicle which can be taken up by a cell via receptor-mediated or other type of endocytosis.

The nucleic acid of this invention can be in a cell, which can be a cell expressing the nucleic acid whereby a polypeptide or fragment thereof of this invention is produced in the cell. In addition, the vector of this invention can be in a cell, which can be a cell expressing the nucleic acid of the vector whereby a polypeptide or fragment thereof of this invention is produced in the cell. It is also contemplated that the nucleic acids and/or vectors of this invention can be present in a host animal (e.g., a transgenic animal) which expresses the nucleic acids of this invention and produces the polypeptides or fragments thereof of this invention.

The present invention provides a composition comprising at least one vector of the present invention and a pharmaceutically acceptable carrier. By "pharmaceutically acceptable" is meant a material that is not biologically or otherwise undesirable, i.e., the material may be administered to an individual along with the selected peptide, polypeptide, nucleic acid, vector or cell without causing substantial deleterious biological effects or interacting in a deleterious manner with any of the other components of the composition in which it is contained. The present invention also provides a composition comprising a salivary polypeptide or fragment thereof and a pharmaceutically acceptable carrier. Also provided is a composition comprising at least one polypeptide or fragment, selected from the group consisting of the polypeptides having SEQ ID NOS: 10-18 and fragments having the SEQ ID NOS: 29-880.

Furthermore, any of the compositions of this invention can comprise in addition to a pharmaceutically acceptable carrier a suitable adjuvant. As used herein, "suitable adjuvant" describes an adjuvant capable of being combined with the polypeptide or fragment thereof of this invention to further enhance an immune response without deleterious effect on the subject or the cell of the subject. A suitable adjuvant can be, but is not limited to, MONTANIDE ISA51 (Seppic, Inc., Fairfield, N.J.), SYNTEX adjuvant formulation 1 (SAF-1), composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), -acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

The present invention provides a method of producing an immune response in a subject, comprising administering to the subject an effective amount of at least one composition of the present invention and a pharmaceutically acceptable carrier. In general, an "effective amount" of an agent is that amount needed to achieve the desired result or results. Detection of an immune response in the subject or in the cells of the subject can be carried out according to the methods set forth in the Examples provided herein, such as detecting the presence of delayed type hypersensitivity activated by the polypeptides or fragments thereof of this invention. As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

The present invention also provides a method of preventing Leishmaniasis in a subject, comprising administering to the subject an effective amount of at least one composition of the present invention and a pharmaceutically acceptable carrier.

In the methods in which the composition comprises a nucleic acid, delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome. The recombinant retrovirus can then be used to infect and thereby deliver to the infected cells nucleic acid encoding the peptide or polypeptide. The exact method of introducing the exogenous nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors and vaccinia viral vectors, as well as any other viral vectors now known or developed in the future. Physical transduction techniques can also be used, such as liposome delivery and receptor-mediated and other endocytosis mechanisms. This invention can be used in conjunction with any of these or other commonly used gene transfer methods. As one example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$ pfu per injection. Ideally, a subject will receive a single injection. If additional injections are necessary, they can be repeated at intervals (1-6 months) for an indefinite period and/or until the efficacy of the treatment has been established. As set forth herein, the efficacy of treatment can be determined by evaluating the clinical parameters described herein. Efficacy of treatment is measured by absence of disease in subjects exposed to the pathogen.

The exact amount of the nucleic acid or vector required will vary from subject to subject, depending on the species, age, weight and general condition of the subject, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein.

The dosage of the composition varies depending on the weight, age, sex, and method of administration. The dosage can also be adjusted by the individual physician as called for based on the particular circumstances. The compositions can be administered conventionally as vaccines containing the active composition as a predetermined quantity of active material calculated to produce the desired therapeutic or immunologic effect in association with the required pharmaceutically acceptable carrier or diluent (i.e., carrier or vehicle). For example, 50 μg of a DNA construct vaccine of the present invention can be injected intradermally three times at two week intervals to produce the desired therapeutic or immunologic effect. In another embodiment, a 1 mg/Kg dosage of a protein vaccine of the present invention can be injected intradermally three times at two week intervals to produce the desired therapeutic or immunologic effect.

Parenteral administration of the polypeptides or fragments thereof, nucleic acids and/or vectors of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous and intratracheal routes. A more recently revised approach for parenteral administration involves use of a slow release or sustained release system such that a constant dosage is maintained. See, e.g., U.S. Pat. No. 3,610,795, which is incorporated by reference herein.

The present invention is more particularly described in the following examples which are intended as illustrative only since numerous modifications and variations therein will be apparent to those skilled in the art.

EXAMPLES

Sand Flies and Preparation of SGH. *P. papatasi*, Israeli strain, were reared at the Walter Reed Army Medical Research Institute, using as larval food a mixture of fermented rabbit feces and rabbit food (20). Adult sand flies were offered a cotton swab containing 20% sucrose and were used for dissection of salivary glands at 2-7d following emergence. Salivary glands were stored in groups of 20 pairs in 20 ml NaCl (150 mM) Hepes buffer (10 mM, pH 7.4). Salivary glands were disrupted by ultrasonication within 1.5-ml conical tubes. Tubes were centrifuged at 10,000 g for 2 min and the resultant supernatant used for the studies.

Mice. C57BL/6 mice were purchased from the Division of Cancer Treatment, National Cancer Institute. $B^{-/-}$ mice were obtained from Taconic Farms. Mice were maintained in the NIAID Animal Care Facility under pathogen-free conditions.

SDS-PAGE. Tris-glycine gels (16%), 1 mm thick, were used (Invitrogen). Gels were run with Tris-glycine buffer according to the manufacturer's instructions. To estimate the mol wt of the samples, SeeBlue™ markers from Invitrogen (myosin, BSA, glutamic dehydrogenase, alcohol dehydrogenase, carbonic anhydrase, myoglobin, lysozyme, aprotinin, and insulin, chain B) were used. SGH were treated with equal parts of 2× SDS sample buffer (8% SDS in Tris-HCl buffer, 0.5M, pH 6.8, 10% glycerol and 1% bromophenol blue dye). Thirty pairs of homogenized salivary glands per lane (approximately 30 mg protein) were applied when visualization of the protein bands stained with Coomassie blue was desired. For amino terminal sequencing of the salivary proteins, 40 homogenized pairs of glands were electrophoresed and transferred to polyvinylidene difluoride (PVDF) membrane using 10 mM CAPS, pH 11, 10% methanol as the transfer buffer on a Blot-Module for the XCell II Mini-Cell (Invitrogen). The membrane was stained with Coomassie blue in the absence of acetic acid. Stained bands were cut from the PVDF membrane and subjected to Edman degradation using a Precise sequencer (Perkin-Elmer Corp.).

Figure 1A:
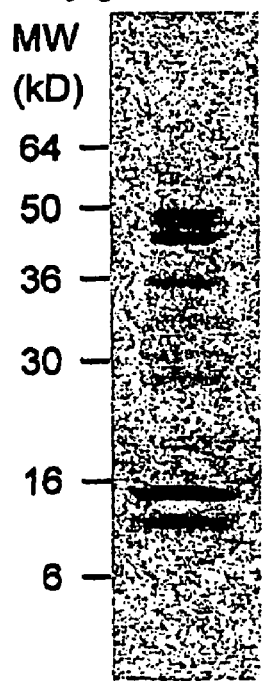
FIG. 1A shows SDS-PAGE of SGH of *P. papatasi* and Coomassie blue-stained PVDF membrane after gel transfer of 40 homogenized pairs of glands. The numbers represent the position of the mol wt markers.

The salivary gland of *P. papatasi* is a sac-like structure consisting of a unicellular epithelium layer surrounding a large lumen (28). After a blood meal, the gland total protein content decreases to half or less from its ~1 µg value (29). Accordingly, most of the protein from the fly SGH must be destined for secretion. Indeed, SDS-PAGE of SGH reveals a low complexity composition consisting of ~12 major bands varying from 10-100 kD (FIG. 1A).

Western Blot Analysis. SDS-PAGE of *P. papatasi* SGH (50 salivary gland pairs) for Western blot analysis was done on 16% Tris-glycine gel containing a single long well (Invitrogen). After electrophoresis, salivary proteins were transferred to a nitrocellulose membrane using Tris-glycine buffer with 10% methanol as the transfer buffer on a Blot-Module for the XCell II Mini-Cell. The nitrocellulose membrane was then incubated overnight at 4° C. with blocking buffer (Tris pH 8.0 plus 150 mM NaCl plus 5% non-fat milk). Following the blocking step, the membrane was placed on a Mini-protean II multi-screen apparatus (Bio-Rad) that allows testing of 16 different serum samples from a single blot. Sera from mice pre-exposed to SGH, from mice bitten by sand flies or from naive mice, were diluted 1:200 with blocking buffer and added individually to various channels on the multi screen apparatus. The membrane was incubated with the different serum samples for 2 h at room temperature. Serum samples were removed from the channels of the multi screen apparatus and washing buffer (Tris, pH 8.0 plus 150 mM NaCl plus 0.1% Tween 20) was added three times. The membrane was then removed from the multi screen device and washed again three times, 5 min per wash, with washing buffer. The membrane was then incubated with a 1:10,000 dilution of an anti-mouse IgG alkaline phosphatase-conjugated antibody for 1 h at room temperature. The membrane was washed three times with washing buffer as described above. Positive bands were visualized by adding alkaline phosphatase substrate (Promega) and the reaction stopped by washing the membrane three times with deionized water.

Figure 1B:
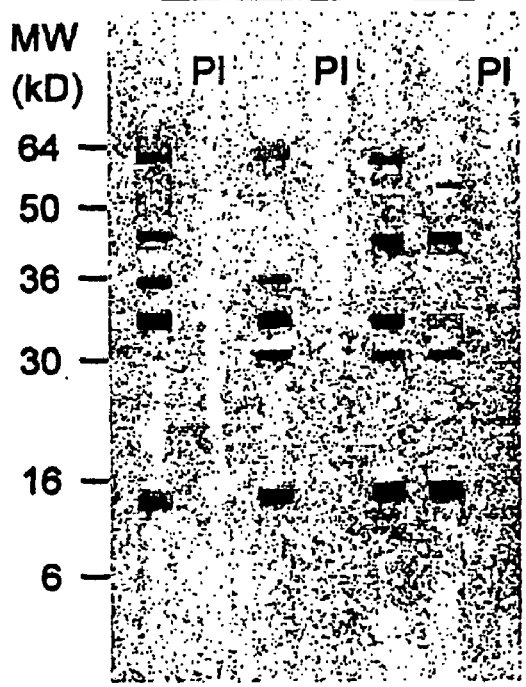
FIG. 1B shows Western blots of the gels with mouse sera obtained from mice immunized by intradermal inoculation of SGH (needle inoculation) or the bite of uninfected sand flies (sand fly bite) with their pre-immunization (PI) controls.

Sera from individual mice inoculated with SGH or exposed to sand fly bites recognized antigens that co-localized with one or more of these major bands when detected by Western blot assays (FIG. 1B). Non-exposed controls or pre-immune sera did not react to *P. papatasi* salivary antigens (FIG. 1B).

Salivary Gland cDNA Library Construction. *P. papatasi* salivary gland mRNA was isolated from eighty-five salivary gland pairs from adult females, at days 1, 2 and 3 after emergence. The Micro-FastTrack mRNA isolation kit (Invitrogen, San Diego, Calif.) was used, yielding a total of 100 ng poly (A)+ mRNA. The PCR-based cDNA library was made following the instructions for the SMART cDNA library construction kit (Clontech, Palo Alto, Calif.). One hundred nanograms of *P. papatasi* salivary gland mRNA was reverse transcribed to cDNA using Superscript II RNase H-reverse transcriptase (Gibco-BRL, Gaithersburg, Md.) and the CDS/ 3' primer (Clontech, Palo Alto, Calif.) for 1 hr at 42° C. Second strand synthesis was performed using a PCR-based protocol by using the SMART III primer (Clontech, Palo Alto, Calif.) as the sense primer and the CDS/3' primer as anti-sense primer, these two primers additionally, create at the ends of the nascent cDNA SfiI A and B sites respectively. Double strand cDNA synthesis was done on a Perkin Elmer 9700 Thermal cycler (Perkin Elmer Corp., Foster City, Calif.) and using the Advantage Klen-Taq DNA polymerase (Clontech, Palo Alto, Calif.). PCR conditions were the following: 94° C. for 2 min; 19 cycles of 94° C. for 10 sec and 68° C. for 6 min. Double strand cDNA was immediately treated with proteinase K (0.8 ng/ul) for 20 minutes at 45° C. and washed three times with water using Amicon filters with a 100 kD cut off (Millipore Corp., Bedford Mass.). The double strand cDNA was then digested with Sfi I for 2 hours at 50° C. (The Sfi I sites were inserted to the cDNA during the second strand synthesis using the SMART in and the CDS/3' primer). The cDNA was then fractionated using columns provided by the manufacturer (Clontech, Palo Alto, Calif.). Fractions containing cDNA of more than 400 bp were pooled, concentrated and washed three times with i water using an Amicon filter with a 100 kD cut-off. The cDNA was concentrated to a volume of 7 µl. The concentrated cDNA was then ligated into a lambda triplex2 vector (Clontech, Palo Alto, Calif.), and the resulting ligation reaction was packed using the Gigapack gold in from Stratagene/Biocrest (Cedar Creek, TE) following manufacturer's specifications. The obtained library was plated by infecting log phase XL1-blue cells (Clontech, Palo Alto, Calif.) and the amount of recombinants was determined by PCR using vector primers flanking the inserted cDNA and visualized on a 1.1% agarose gel with ethidium bromide (1.5 µg/ml).

Massive Sequencing of *P. papatasi* Salivary Gland cDNA Library. *P. papatasi* salivary gland cDNA library was plated to ca. 200 plaques per plate (150 mm Petri dish). The plaques were randomly picked and transferred to a 96 well polypropylene plate containing 100 µl of water per well. The plate was covered and placed on a gyrator shaker for 1 hr at room temperature. Five microliters of the phage sample was used as a template for a PCR reaction to amplify random cDNAs. The primers used for this reaction were sequences from the triplEX2 vector, the primers were named PT2F1 (5'-AAGTACTCT AGCAAT TGTGAGC-3') (SEQ ID NO:881) which is positioned upstream of the cDNA of interest (5' end), and PT2R1 (5'-CTCTTCGCTATTACGCCAGCT G-3') (SEQ ID NO:882) which is positioned downstream of the cDNA of interest (3' end). High fidelity platinum Taq polymerase (Gibco-BRL, Gaithersburg, Md.) was used for these reactions. Amplification conditions were: 1 hold of 75° C. for 3 minutes, 1 bold of 94° C. for 3 minutes and 34 cycles of 94° C. for 30 sec, 49° C. for 30 sec and 72° C. for 1 min and 20 sec. Amplified products were visualized on a 1.1% agarose gel with ethidium bromide. The concentration of double strand cDNA was measured by using the Hoechst dye 33258 on a Fluorite 1000 plate fluorometer (Dynatech Laboratories, Chantilly, Va.). Three to four microliters of PCR reaction containing between 100 to 200 ng of DNA were then treated with Exonuclease I (0.5 U/μl) and shrimp alkaline phosphatase ( 0.1 U/μl) for 15 minutes at 37° C. and 15 minutes at 80° C. on a 96-well PCR plate. This mixture was used as a template for a cycle sequencing reaction using the DTCS labeling kit from Beckman Coulter Inc. (Fullerton, Calif.). The primer used for sequencing (PT2F3) is upstream of the inserted cDNA and downstream of the primer PT2F1. Sequencing reaction was performed on a Perkin Elmer 9700 thermacycler. Conditions were 75° C. for 2 min, 94° C. for 4 min, and 30 cycles of 96° C. for 20 sec, 50° C. for 20 sec and 60° C. for 4 min. After cycle sequencing the samples, a cleaning step was done using the multi-screen 96 well plate cleaning system from Millipore (Bedford, Mass.). The 96 well multi-screening plate was prepared by adding a fixed amount (according to the manufacturer's specification) of Sephadex-50 (Amersham Pharmacia Biotech, Piscataway, N.J.) and 300 μl of deionized water. After 1 hour of incubation at room temperature, the water was removed from the multi screen plate by centrifugation at 750 g for 5 minutes. After the Sephadex in the multi-screen plate was partially dried, the whole cycle sequencing reaction was added to the center of each well, centrifuged at 750 g for 5 minutes and the clean sample was collected on a sequencing microtiter plate (Beckman Coulter, Fullerton, Calif.). The plate was then dried on Speed-Vac SC 110 model with a microtiter plate holder (Savant Instruments Inc, Holbrook, N.Y.). The dried samples were immediately resuspended with 25 μl of deionized ultrapure formamide (J. T. Baker, Phillipsburg, N.J.), and one drop of mineral oil was added to the top of each sample. Samples were sequenced immediately on a CEQ 2000 DNA sequencing instrument (Beckman Coulter Inc., Fullerton, Calif.) or stored at –30° C. The entire cDNA of selected genes was fully sequenced using custom primers using a CEQ 2000 DNA sequencing instrument (Beckman Coulter Inc., Fullerton, Calif.) as described above. The P. papatasi salivary gland cDNA library was plated to approximately 200 plaques/plate (150 mm Petri dish), and sequenced as previously described (30).

DNA Vaccine Construction and Description of the VR1020 Vector. The gene coding for SP15 (from N-terminus to stop codon) was amplified from P. papatasi SP15-specific cDNA by PCR using High-Fidelity platinum Taq polymerase (GIBCO BRL) and specific primers carrying BamHI restriction sites (Forward SP15BHF 5'-TGCGGATCCGAAAATCCATCAAAGAAG-3' (SEQ ID NO: 883); Reverse SP15BHR 5'-ATTGGATCCTTATATATTGATTGTTTT-3')(SEQ ID NO:884)). The PCR product was immediately cloned into the TOPO TA cloning vector PCRII (Invitrogen) following manufacturer's specifications. The ligation mixture was used to transform TOP 10 cells (Invitrogen) and the cells were incubated overnight at 37° C. Eight colonies were picked and mixed with 10 ml of sterile water. Five ml of each sample were transferred to Luria broth with ampicillin (100 mg/ml) and grown at 37° C. The other 5 ml were used as a template for a PCR reaction using two vector-specific primers from the PCPII vector to confirm the presence of the insert and for sequencing analysis. After visualization of the PCR product on a 1.1% agarose gel, the eight PCR products were completely sequenced as described above using a CEQ2000 DNA sequencing instrument (Beckman Coulter). A sample that contained the sequence from the N-terminus to stop codon of the SP15 gene including the incorporated BamHI sites was chosen. Cells containing the plasmid carrying the SP15 gene were grown overnight at 37° C. on Luria broth with ampicillin (100 mg/ml), and plasmid isolation was performed using the Wizard Miniprep kit (Promega). The plasmid containing the SP15 gene with incorporated BamHI sites was digested with BamHI and then ligated with the BamHI predigested VR1020 DNA plasmid vector (VICAL). The VR1020plasmid contains a kanamycin resistance gene, the human cytomegalovirus promoter, and the tissue plasminogen activator signal peptide upstream of the BamHI cloning site. The ligation reaction between the BamHI digested SP15 gene and the similarly digested VR1020 DNA vector was done overnight at 16° C. to transform TOP 10 cells (Invitrogen). Cells were incubated on a Luria broth kanamycin (30 mg/ml) plate overnight at 37° C. Thirty-two colonies were picked and mixed with 10 ml of sterile water. Five ml of each sample were transferred to Luria broth with kanamycin (100 mg/ml) and grown at 37° C. The other 5 ml were used as a template for a PCR reaction using two vector-specific primers from the VR1020 vector to confirm the presence of the insert and for sequencing analysis. After visualization of the PCR product on a 1.1% agarose gel, four PCR products were completely sequenced as described above using a CEQ2000 DNA sequencing instrument (Beckman Coulter). For the vaccine construct, a sample that contained the sequence from the N-terminus to the stop codon in the right orientation and in the correct open-reading-frame following the tissue plasminogen activator signal peptide was chosen. Cells containing the SP15 gene on VR1020 were grown overnight at 37° C. on Luria broth with kanamycin (100 mg/ml), and plasmid isolation was performed using the Wizard Miniprep kit. After plasmid isolation, the sample and control plasmids (VR1020 alone) were washed three times with ultrapure water using an Amicon-100 (Millipore). The concentrations of the samples were measured by UV absorbance, and they were stored at –70° C. before immunization experiments.

DNA and Predicted Protein Sequence Analysis. DNA data derived from the mass sequencing project were analyzed by an in-house program written in VisualBASIC (Microsoft). This program removed vector and primer sequences from the raw sequence. Stripped sequences were compared to the NCBI non-redundant protein database using the program BlastX using the BLOSUM-62 matrix (21). DNA sequences were clustered by blasting the database against itself with a preselected threshold cutoff, usually $le^{-10}$ (BlastN program) (21). Sequences from the same cluster were aligned using ClustalX (22). To find the cDNA sequences corresponding to the amino acid sequence obtained by Edman degradation of the proteins transferred to PVDF membranes from PAGE gels, a search program was written that checked these amino acid sequences against the three possible protein translations of each cDNA sequence obtained in the mass sequencing project. This was written using the same approach used in the BLOCKS (23) or Prosite (24) programs. Protein translations of i the full-length clones were further processed to identify the predicted signal peptides using the Signal P program (25), available at http://genome.cbs.dtu.dk/services/SignalP/. Predicted signal peptide cleaved sites were compared to the N-terminus sequence obtained from Edman degradation of *P. papatasi* salivary proteins. Estimation of isoelectric point and mol wt of translated protein was performed using the DNA STAR program (DNASTAR). Full-length translated protein sequence information was compared with the non-redundant protein database of NCBI using the BLAST-P program (21) and searched for motifs by submitting each sequence to http://www.morif.genome.ad.jp/.

Figure 2:
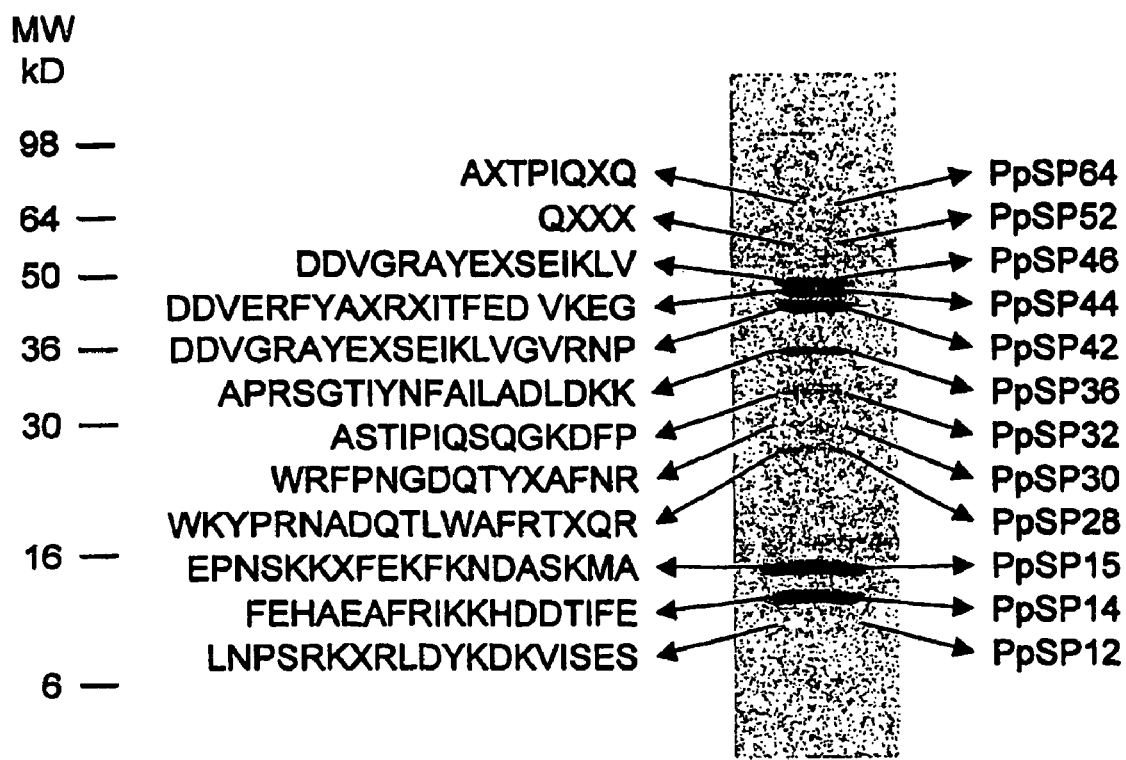
FIG. 2 shows SDS-PAGE of 20 homogenized pairs of salivary glands from *P. papatasi*. Left side of figure shows the amino terminal sequence found for each band by Edman degradation; the right side of FIG. shows the clone identification name. Numbers indicate the position of the mol wt marker in the same gel.

To characterize the primary structure of the main proteins of *P. papatasi* SGH, SDS-PAGE gels were transferred to PVDF membranes, and the amino terminal sequence of each cut band by Edman degradation were estimated. Of 12 bands, with the exception of one that is probably blocked by a pyroglutamyl residue (amino terminal sequence QXXX), 11 bands yielded information as shown in FIG. 2. The amino terminal sequences were used to screen a 3-frame translation of a cDNA database originating from ~600 DNA sequences obtained from randomly picked clones from a unidirectionally cloned salivary gland cDNA library. Matching clones were subsequently fully sequenced using custom primers. The proteins in FIG. 2 are named according to their mobility in non-reducing SDS-PAGE. A brief description of the clones is enclosed in Table I, with their NCBI accession numbers, best match to the NCBI NR. protein database, predicted mol wt, and motifs found. All proteins had a predicted signal secretory sequence (25), and their site of cleavage was confirmed by Edman degradation. All proteins were basic, with a pi ranging from 8.28 to 9.43. Note that the same amino terminal sequence for two SDS-PAGE bands was obtained, located at 32 kD and 64 kD; the heavier is presumed to be a homodimer. Additionally, the same amino terminal sequence was obtained from the SDS-PAGE bands located at 42 kD and 46 kD, the difference possibly arising from post-translation modification.

Parasite Preparation and Intradermal Inoculation. *L. major* clone VI (MHOM/IL/80/Friedlin) was cultured in 199 medium with 20% heat-inactivated fetal bovine serum (Hy-Clone), 100 U/ml penicillin, 100 mg/ml streptomycin, 2 mM L-glutamine, 40 mM Hepes, 0.1 mM adenine (in 50 mM Hepes), 5 mg/ml heroin (in 50% triethanolamine), and 1 mg/ml 6-biotin (M199/S). Infective-stage metacyclic promastigotes of *L. major* were isolated from stationary cultures (4-5 d old) by negative selection using peanut agglutinin (Vector Labs). Five hundred metacyclic promastigotes with or without 0.5 pair of SGH were inoculated intradermally into the left ear dermis using a 27-gauge needle in a volume of approximately 5 ml. The evolution of the lesion was monitored by measuring the diameter of the induration of the ear lesion with a direct-reading Vernier caliper (Thomas Scientific).

Estimation of Parasite Load. Parasite titrations were performed as previously described (16, 25).

Vaccination. SGH (30 salivary gland pairs) was separated by SDS-PAGE and stained with Coomassie blue as described above. The gel was divided into three groups (bands) containing proteins in the range of 200 to 50 kD (Fraction A, approximately 11 mg), from 49 to 20 kD (Fraction B, approximately 9 mg), and below 20 kD (Fraction C, approximately 10 mg). A control piece of acrylamide from the gel was used (Fraction E). The gel was cut and the bands transferred to a 1.5-ml tube and washed three times with sterile PBS (pH 6.8) plus 150 mM NaCl. The bands were then triturated using a plastic pestle until the preparation could be resuspended in 500 ml of sterile phosphate-saline buffer using a 27-gauge needle to give a solution of approximately 0.02 mg/ml. Immunization with SDS-PAGE fractions was carried out by the injection of 10 ml of either Fraction A, B, C, or E into the right ear of each mouse, followed by a boost 2 wk later. For genetic immunization, mice were inoculated in the right ear with 5-10 mg of the plasmid encoding for SP15 or control DNA (empty vector) suspended in 5 ml of PBS. Each group was boosted 2 wk later using the same regimen. Mice were bled and the presence of antibodies assessed for each individual mouse by Western blot as described above.

Analysis of the Inflammatory Response in the Ear Dermis. The left ears of mice vaccinated with the plasmid vector (in the right ear) or not vaccinated were exposed to the bite of sand flies as previously described (19). Twenty-four h following the sand fly exposure, seven mice per group were sacrificed and the left ear collected. Each ear was processed individually. The cells in the inflammatory ear dermis were recovered as previously described (17).

Immunolabeling for Flow Cytometry Analysis. The dermal cells were incubated with 10% normal mouse serum in PBS containing 0.1% BSA, 0.01% NaN, before being incubated with anti-Fc receptor antibody (2.4 G2, PharMingen). The double staining was done by using directly conjugated antibodies incubated simultaneously. The dermal inflammatory cells were identified by characteristic size, forward scatter (FSC) and granulosity, side scatter (SSC) combined with two-color analysis, as previously described (27).

Statistical Analysis. Statistical tests were performed with SigmaStat (Jandel Software, San Rafael, Calif.). Because most comparisons derived from data with non-homogeneous variances, Kruskal-Wallis ANOVA on ranks was performed and multiple comparisons were done by the Dunn method. Dual comparisons were made with the Mann-Whitney rank sum test. All data from parasite numbers were log-transformed prior to conducting statistical tests.

Immune Responses. To investigate which fractions from saliva produce the most effective protection when mice are subsequently challenged with parasites and SGH, SGH was separated by SDS-PAGE, and the gel was divided into three groups containing proteins in the range of 200 kD to 40 kD, from 39 kD to 20 kD, and below 20 kD. A control group receiving gel without proteins was also run, together with non-injected controls. After intradermal immunization in the ear, mice were challenged in the contralateral ear with parasites and SGH. Naive mice inoculated with SGH plus parasites had significantly increased lesion size at 5.5 weeks post inoculation, when compared with naive mice inoculated with parasites only. Mice vaccinated with the lower mol wt fractions (Fraction C), and challenged with both parasites and SGH had the best protection in this assay (FIG. 3A) ($P<0.05$). Parasite load at 4.5 wk post inoculation were also lower in fraction C-vaccinated mice ($P<0.05$) (FIG. 3 B). A strong antibody response was obtained when mice were inoculated with the smaller protein size region of the gel (FIG. 4). Within this group, a stronger reaction was mounted against an antigen identical to or co-migrating with a protein of 15 kD, here named SP15 protein (PpSP15), as identified in FIG. 2 and Table I.

To test the role of the SP15 gel region in conferring resistance to leishmaniasis in mice, mice were vaccinated with the SP15 band obtained from SDS-PAGE or with an acrylamide control injection and challenged with *L. major* in the presence and absence of SGH. Results indicated that vaccination with the SP15 band greatly affected disease manifestation as measured by lesion size, which were significantly smaller (P<0.05) than those of mice vaccinated but not receiving SGH at the time of Leishmania inoculation or of acrylamide-vaccinated mice receiving parasites plus SGH (FIG. 5A). The parasite load at 9-wk post inoculation was smaller on the SP15-vaccinated mice challenged with parasites and SGH, but only borderline so (P=0.056) when compared with the acrylamide-vaccinated controls (FIG. 5B. This may be explained by the presence of acrylamide in the preparation. Acrylamide was used as an adjuvant, and this may be the reason for these results (acrylamide confers some level of protection). When these experiments were repeated using DNA vaccination, the lesion size and the parasite number were significantly lower in the SP15 DNA-vaccinated mice as compared to control DNA-vaccinated mice.

To further confirm whether immunity against SP15 could protect mice when parasites are co-injected with SGH, a DNA vaccine was constructed using the P. papatasi salivary SP15 gene. The SP15 cDNA is 522 bp in length and codes for a protein of 142 amino acids including the signal peptide. The mature protein, as predicted by the Signal P program and confirmed by Edman degradation, has 14,494.81 dalton. Accordingly, the SP15 gene coding for the mature protein was inserted downstream and in frame with the signal peptide of tissue plasminogen activator present in the VR1020 vector. This construct is named SP15-PI. Control plasmids, i consisting of VR1020 plasmid alone, were used to immunize control mice. This control plasmid is named CTL-P1. Mice immunized with SP15-PI, but not those immunized with the CTL-P1, produced antibodies recognizing a single band in Western blots of SGH, at the position of SP15 in the gel (FIG. 6A). Additionally, to determine whether the SP15 vaccination would induce a DTH response in mice following the bite of uninfected sand flies, naïve, SP15-PI-immunized, and plasmid control-immunized mice were exposed to sand fly bites. Results indicate that mice vaccinated with SP15-PI developed an intense DTH response 24 h following exposure to sand flies (FIG. 6B). This reaction is characterized by swelling and a massive cell infiltrate consisting primarily of neutrophils, eosinophils, and macrophages (FIG. 6B). This experiment indicates that the plasmid vaccine is producing both serum and cellular immunity reactions.

The effects of immunization with SP15-PI on the development of L. major infection co-injected or not with SGH were investigated. The intradermal co-inoculation of 500 L. major with 0.5 pair of SGH had a dramatic effect on the pathology in naive mice or mice vaccinated with CTL-PI (FIG. 7). The lesions developed more rapidly and presented an ulcerative pathology compared with controls inoculated without saliva. In contrast, mice previously vaccinated with SP15-PI and challenged with parasite plus SGH developed a minor and non-ulcerative pathology. The lesions were significantly smaller not only compared with controls (naive or CTL-PI) inoculated with saliva but also compared with mice inoculated with the parasite alone. The induration in the SP15-PI-vaccinated mice resolved as early as 6 wk post challenge, while in the CTL-PI-immunized mice inoculated with saliva, the large ulcerative, necrotic lesions are maintained. Similarly, the intradermal co-inoculation of 500 L. major with 0.5 pair of SGH enhanced the parasite load in naive and CTL-PI vaccinated C57BL/6 mice compared with their respective controls, inoculated with the parasite alone (FIG. 7).

To evaluate the persistence of the immunity induced by the DNA vaccine, the animals were challenged or not with SGH 12 wk, rather than 2 wk, after the last boosting. The protection was comparable to that achieved when the challenge was performed 2 wk post vaccination, with a significant reduction of both lesion size and parasite number (FIG. 8).

Having shown that immunization with SP15-PI induces both antibody and DTH (FIG. 6) responses, the contribution of antibodies versus cellular immunity in the anti-Leishmania protective effect was evaluated. $B^{-/-}$ mice were immunized with SP15-PI and CTL-PI with the expectation that this model animal would provide only a cellular response to SP15. Indeed, similarly to the wild-type (WT) controls only $B^{-/-}$ mice vaccinated with SP15-PI developed an intense DTH response when challenged with 500 L. major promastigotes in the presence of 0.5 pairs of SGH (FIG. 9B). As expected, no antibodies from the $B^{-/-}$ mice were detected by Western blots, .(FIG. 9A), although antibodies were produced by the control WT mice (B10 mice). When challenged with parasites and SGH, vaccinated $B^{-/-}$ mice had significantly lower pathology at 5.5 wk post inoculation than did mice vaccinated with the control plasmid (P=0.008) (FIG. 10A). When compared with the CTL-PI-vaccinated mice (P<0.05), parasite loads at 5.5 wk post inoculation were significantly lower in mice vaccinated with SP15-PI and inoculated with parasites plus SGH, irrespective of whether the mice were B cell deficient (FIG. 10B). Comparisons of the parasite loads between $B^{-/-}$ and WT mice indicated that $B^{-/-}$ mice had smaller parasite loads than the WT controls (P=0.006).

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

1. Killick-Kendrick, R. 1979. Biology of Leishmania in phlebotomine sand flies. In Biology of the kinetoplastida. W. Lumsden and D. Evans, editors. Academic Press, New York. 395.
2. Ribeiro, J. M., P. A. Rossignol, and A. Spielman. 1986. Blood-finding strategy of a capillary-feeding sand fly, Lutzomyia longipalpis. Comp. Biochem. Physiol. 4:683-686.
3. Charlab, R., J. G. Valenzuela, E. D. Rowton, and J. M. Ribeiro. 1999. Toward an understanding of the biochemical and pharmacological complexity of the saliva of a hematophagous sand fly Lutzomyia longipalpis. Proc. Natl. Acad. Sci. USA. 26:15155-15160.
4. Lerner, E. A., J. M. Ribeiro, R. J. Nelson, and M. R. Lerner. 1991. Isolation of maxadilan, a potent vasodilatory peptide from the salivary glands of the sand fly Lutzomyia longipalpis. J. Biol. Chem. 17:11234-11236.
5. Qureshi, A. A., A. Asahina, M. Ohnuma, M. Tajima, R. D. Granstein, and E A. Lerner. 1996. Immunomodulatory properties of maxadilan, the vasodilator peptide from sand fly salivary gland extracts. Am. J. Trop. Med. Hyg. 6:665-671.
6. Makoul, G. T., D. R. Robinson, A. K. Bhalla, and L A. Glimcher. 1985. Prostaglandin E2 inhibits the activation of cloned T cell hybridomas. J. Immunol. 134:2645-2650.
7. Santoli, D., and R. B. Zurier. 1989. Prostaglandin E precursor fatty acids inhibit human IL-2 production by a prostaglandin E-independent mechanism. J. Immunol. 143:1303-1309.

8. Stockman, G. D., and D. M. Mumford. 1974. The effect of prostaglandins on the in vitro blastogenic response of human peripheral blood lymphocytes. *Exp. Hematol.* 2:65-72.

9. Nong, Y. H., R. G. Titus, J. M. Ribeiro, and H. G. Remold. 1989. Peptides encoded by the calcitonin gene inhibit macrophage function. *J. Immunol.* 1:45-49.

10. Ribeiro, J. M., O. Katz, L. K. Pannell, J. Waitumbi, and A. Warburg. 1999. Salivary glands of the sand fly *Phlebotomus papatasi* contain pharmacologically active amounts of adenosine and 5'-AMP. *J. Exp. Biol.* 11:1551-1559.

11. Hasko, G., C. Szabo, Z. H. Nemeth, V. Kvetan, S. M. Pastores, and E. S. Vizi. 1996. Adenosine receptor agonists differentially regulate IL-10, TNF-alpha, and nitric oxide production in RAW 264.7 macrophages and in endotoxemic mice. *J. Immunol.* 10:4634-4640.

12. Webster, H. K. 1984. Role of purines in lymphocyte function. *Asian Pac. J. Allergy Immunol.* 2:311-317.

13. Hasko, G., D. G. Kuhel, J. F. Chen, M. A. Schwarzchild, E. A. Deitch, J. G. Mabley, A. Marton, and C. Szabo. Adenosine inhibits IL-12 and TNF-alpha production via adenosine A2a receptor-dependent and -independent mechanisms. *FASEB J.* 14:2065-2074.

14. Katz, O., J. N. Waitumbi, R. Zer, and A. Warburg. 2000. Adenosine, AMP, and protein phosphatase activity in sand fly saliva. *Am. J. Trop. Med. Hyg.* 1:145-150.

15. Titus, R. G., and J. M. Ribeiro. 1988. Salivary gland lysates from the sand fly *Lutzomyia longipalpis* enhance *Leishmania* infectivity. *Science.* 239:1306-1308.

16. Theodos, C M., J. M. Ribeiro, and R. G. Titus. 1991. Analysis of enhancing effect of sand fly saliva on Leishmania infection in mice. *Infect. Immun.* 59:1592-1598.

17. Belkaid, Y., S. Kamhawi, G. Modi, J. Valenzuela, N. Noben-Trauth, E. Rowton, J. M. Ribeiro, and D. L. Sacks. 1998. Development of a natural model of cutaneous leishmaniasis: powerful effects of vector saliva and saliva pre-exposure on the long-term outcome of Leishmania major infection in the mouse ear dermis. *J. Exp. Med.* 188:1941-1953.

18. Kamhawi, S., Y. Belkaid, G. Modi, E. Rowton, and D. Sacks. 2000. Protection against cutaneous leishmaniasis resulting from bites of uninfected sand flies. *Science* 290:1351-1354.

19. Belkaid, Y., J. G. Valenzuela, S. Kamhawi, E. Rowton, D. L. Sacks, and J. M. Ribeiro. 2000. Delayed-type hypersensitivity to *Phlebotomus papatasi* sand fly bite: An adaptive response induced by the fly? *Proc. Natl. Acad. Sci. USA* 97:6704-6709.

20. Modi, G. B., and R. B. Tesh. 1983. A simple technique for mass rearing *Lutzomyia longipalpis* and *Phlebotomus papatasi* (Diptera: Psychodidae) in the laboratory. *J. Med. Ent.* 20:568-569.

21. Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. *Nucleic Acids Res.* 25:3389-3402.

22. Jeanmougin, F., J. D. Thompson, M. Gouy, D. G. Higgins, and T. J. Gibson. 1998. Multiple sequence alignment with Clustal X. *Trends Biochem. Sci.* 23:403-405.

23. Henikoff, S., J. G. Henikoff, and S. Pietrokovski. 1999. Blocks+: a non-redundant database of protein alignment blocks derived from multiple compilations. *Bioinformatics* 15:471-479.

24. Bairoch, A. 1991. PROSITE: a dictionary of sites and patterns in proteins. Nucleic Acids Res. 19(Suppl.):2241-2245.

25. Nielsen, H., J. Engelbrecht, S. Brunak, and G. von Heijne. 1997. Identification of prokaryotic and eukaryotic signal peptides and prediction of their cleavage sites. *Protein Eng.* 10:1-6.

26. Titus, R. G., M. Marchand, T. Boon, and J. A. Louis. 1985. A limiting dilution assay for quantifying *Leishmania major* in tissues of infected mice. *Parasite Immunol.* 7:545-555.

27. Belkaid, Y., H. Jouin, and G. Milon. 1996. A method to recover, enumerate and identify lymphomyeloid cells present in an inflammatory dermal site: a study in laboratory mice. *J. Immunol. Methods.* 199:5-25.

28. Adler, S., and O. Theodor. 1926. The mouthparts, alimentary tract and salivary apparatus of the female *Phlebotomus papatasi*. Ann. Trop. Med. Parasitol. 20:109.

29. Ribeiro, J. M. C., G. B. Modi, and R. B. Tesh. 1989. Salivary apyrase activity of some Old World phlebotomine sand flies. *Insect Biochem.* 19:409-412.

30. Valenzuela, J. G., Y. Belkaid, E. Rowton, and J. M. Ribeiro. 2001. The salivary apyrase of the blood-sucking sand fly *Phlebotomus papatasi* belongs to the novel Cimex family of apyrases. *J. Exp. Biol.* 204:229-237.

31. Robertson, H. M., R. Martos, C. R. Sears, E. Z. Todres, K. K. Walden, and J. B. Nardi. 1999. Diversity of odourant binding proteins revealed by an expressed sequence tag project on male Manduca sexta moth antennae. *Insect Mol. Biol.* 8:501-518.

32. Paesen, G. C., P. L. Adams, K. Harlos, P. A. Nuttall, and D. I. Stuart 1999. Tick histamine-binding proteins: isolation, cloning, and three-dimensional structure. *Mol. Cell.* 3:661-671.

33. Francischetti, I. M., J. M. Ribeiro, D. Champagne, and J. Andersen. 2000. Purification, cloning, expression, and mechanism of action of a novel platelet aggregation inhibitor from the salivary gland of the blood-sucking bug, *Rhodnius prolixus. J. Biol. Chem.* 275:12639-12650.

34. Ribeiro, J. M. C., and F. A. Walker. 1994. High affinity histamine-binding and antihistamimc activity of the salivary nitric oxide-carrying heme protein (nitrophorin) of *Rhodnius prolixus. J. Exp. Med.* 180:2251-2257.

35. Smelt, S. C., S. E. Cotterell, C. R. Engwerda, and P. M. Kaye. 2000. B cell-deficient mice are highly resistant to Leishmania donovani infection, but develop neutrophil-mediated tissue pathology. *J. Immunol.* 164:3681-3688.

36. Guy, R A., and M. Belosevic. 1993. Comparison of receptors required for entry of *Leishmania major* amastigotes into macrophages. *Infect Immun.* 61:1553-1558.

37. Belkaid, Y., S. Mendez, R Lira, N. Kadambi, G. Milon, and D. Sacks. 2000. A natural model of *Leishmania major* infection reveals a prolonged "silent" phase of parasite amplification in the skin before the onset of lesion formation and immunity. *J. Immunol.* 165:969-977.

38. Franco, R., A. Valenzuela, C. Lluis, and J. Blanco. 1998. Enzymatic and extraenzymatic role of ecto-adenosine deaminase in lymphocytes. *Immunol. Rev.* 161:27-42.

39. Hasko, G., D. G. Kuhel, Z. H. Nemeth, J. G. Mabley, R. F. Stachlewitz, L. Virag, Z. Lohinai, G. J. Southan, A. L. Salzman, and C. Szabo. 2000. Inosine inhibits inflammatory cytokine production by a post transcriptional mechanism and protects against endotoxin-induced shock. *J. Immunol.* 164:1013-1019.

40. Xu, D., and F. Y. Liew. 1995. Protection against leishmaniasis by injection of DNA encoding a major surface glycoprotein, gp63, of *L. major. Immunology.* 84:173-176.

41. Gurunathan, S., D. L. Sacks, D. R. Brown, S. L. Reiner, H. Charest, N. Glaichenhaus, and R. A. Seder. 1997. Vaccination with DNA encoding the immunodominant LACK parasite antigen confers protective immunity to mice infected with *Leishmania major. J. Exp. Med.* 186:1137-1147.
42. Gurunathan, S., C. Prussin, D. L. Sacks, and R. A. Seder. 1998. Vaccine requirements for sustained cellular immunity to an intracellular parasitic infection. *Nat. Med.* 4:1409-1415.
43. Sjolander, A., T. M. Baldwin, J. M. Curtis, and E. Handman. 1998. Induction of a Th1 immune response and simultaneous lack of activation of a Th2 response are required for generation of immunity to leishmaniasis. *J. Immunol.* 160:3949-3957.
44. Mendez, S., S. Gurunathan, S. Kamhawi, Y. Belkaid, M. A. Moga, Y. A. W. Skeiky, A. Campos-Neto, S. Reed, R. A. Seder, and D. Sacks. 2001. The potency and durability of DNA- and protein-based vaccines against *Leishmania major* evaluated using low dose, intradermal challenge. *J. Immunol.* In press.
45. Barral, A., E. Honda, A. Caldas, J. Costa, V. Vinhas, E. D. Rowton, J. G. Valenzuela, R. Charlab, and J. M. C. Ribeiro. 2001. Human immune response to sand fly salivary gland antigens: A useful epidemiological marker? *Am. J. Trop. Med. Hyg.*

What is claimed is:

1. An isolated nucleic acid encoding a salivary polypeptide of *Phlebotomus papatasi* comprising the amino acid sequence set forth as SEQ ID NO:12.

2. An isolated nucleic acid encoding a salivary polypeptide of *Phlebotomus papatasi*, comprising nucleic acid residues 18-446 of SEQ ID NO: 21.

3. An isolated nucleic acid encoding a salivary polypeptide of *Phlebotomus papatasi* consisting of the nucleic acid sequence set forth as nucleic acid residues 78-134 of SEQ ID NO: 21.

4. The isolated nucleic acid of claim 3, wherein the isolated nucleic acid encodes an antigenic or immunogenic polypeptide.

5. An in vivo expression vector comprising the isolated nucleic acid of claim 1.

6. An in vivo expression vector comprising the isolated nucleic acid of claim 2.

7. A pharmaceutical composition comprising an effective amount of the vector of claim 5 and a pharmaceutically acceptable carrier.

8. A pharmaceutical composition comprising an effective amount of the vector of claim 6 and a pharmaceutically acceptable carrier.

9. The isolated nucleic acid of claim 2, comprising the nucleotide sequence set forth as SEQ ID NO: 21.

10. The isolated nucleic acid of claim 1, wherein the nucleic acid encodes the *Phlebotomus papatasi* salivary polypeptide consisting of the amino acid sequence set forth as SEQ ID NO: 12.

11. The isolated nucleic acid of claim 2, consisting of the nucleic acid sequence set forth as residues 18-446 of SEQ ID NO: 21.

12. The isolated nucleic acid of claim 9, consisting of the nucleotide sequence set forth as SEQ ID NO: 21.

13. A method of producing an immune response in a subject, comprising administering to the subject an effective amount of the composition of claim 7 thereby producing an immune response.

14. A method of producing an immune response in a subject, comprising administering to the subject an effective amount of the composition of claim 8, thereby producing an immune response.

* * * * *

UNITED STATES PATENT AND TRADEMARK OFFICE
CERTIFICATE OF CORRECTION

PATENT NO. : 7,964,576 B2
APPLICATION NO. : 12/082369
DATED : June 21, 2011
INVENTOR(S) : Valenzuela et al.

Page 1 of 4

It is certified that error appears in the above-identified patent and that said Letters Patent is hereby corrected as shown below:

In the Figures:

FIG. 10A, "wt CT1-P1" should read --wt CTL-P1--.

In the Specification:

Column 1, line 66, "not exist Thus," should read --not exist. Thus,--.

Column 2, line 11, "polypeptide *Phlebotomus*" should read --polypeptide of *Phlebotomus*--.

Column 3, line 8, "duration in mm ± SB" should read --duration in mm ± SE--.

Column 3, line 37, "sequence (SP15-PI)." should read --sequence (SP15-P1).--.

Column 3, line 39, "the SP15-PI or" should read --the SP15-P1 or--.

Column 3, line 43, "sequence (SP15-PI)." should read --sequence (SP15-P1).--.

Column 3, line 44, "with SP15-PI." should read --with SP15-P1.--.

Column 3, line 45, "with SP15-PI, or." should read --with SP15-P1, or--.

Column 3, line 46, "of 10sand flies" should read --of 10 sand flies--.

Column 3, line 52, "with SP1S-" should read --with SP15- --.

Column 3, line 54, "with 500*L. major*" should read --500 *L. major*--.

Column 3, line 65, "with SP15-PI on" should read --with SP15-P1 on--.

Column 4, line 2, "with SP15-PI (□,■) or CTL-PI (Δ,▲) were" should read --with SP15-P1 (□,■) or CTL-P1 (Δ,▲) were--.

Column 4, line 7, "with SP 15-PI on" should read --with SP15-P1 on--.

Column 4, line 12, "reaction oh" should read --reaction on--.

Column 4, line 13, "with SP15-PI." should read --with SP15-P1.--.

Column 4, line 14, "not mice" should read --not $B^{-/-}$ mice--.

Column 4, line 18, "C57BL/10mice" should read --C57BL/10 mice--.

Signed and Sealed this
Twenty-third Day of October, 2012

David J. Kappos
*Director of the United States Patent and Trademark Office*

CERTIFICATE OF CORRECTION (continued)
U.S. Pat. No. 7,964,576 B2

Column 4, line 19, "with SP15-PI." should read --with SP15-P1.--.

Column 4, line 20, "of SP15-PI or" should read --of SP15-P1 or--.

Column 4, line 30, "Bounce (Δ, ▲)" should read --B$^{-/-}$ mice (Δ, ▲)--.

Column 4, line 38, "with SP15-PI on" should read --with SP15-P1 on--.

Column 4, line 42, "SP15-PI group" should read --SP15-P1 group--.

Column 5, line 3, "30amino" should read --30 amino--.

Column 5, line 33, "PpSP12polypeptide." should read --PpSP12 polypeptide.--.

Column 5, line 40, "PpSP12polypeptide" should read --PpSP12 polypeptide--.

Column 5, line 56, "PpSP14 polypeptide, is" should read --PpSP14 polypeptide is--.

Column 6, line 34, "of P. papatasi having" should read --of *P. papatasi* having--.

Column 6, line 47, "of P. papatasi having" should read --of *P. papatasi* having--.

Column 7, line 5, "the PpSP44polypeptide." should read --the PpSP44 polypeptide.--.

Column 8, line 1, "SEQ ED" should read --SEQ ID--.

Column 8, line 60, "glutatbione-S-transferase" should read --glutathione-S-transferase--.

Column 8, line 65, "polypeptide's activity." should read --polypeptide's activity).--.

Column 9, line 13, "art Such" should read --art. Such--.

Column 10, line 28, "SEQ ED NO:19." should read --SEQ ID NO:19.--.

Column 10, line 32, "acid mat encodes" should read --acid that encodes--.

Column 10, line 37, "acid mat encodes" should read --acid that encodes--.

Column 10, line 63, "SEQ ED NO:26." should read --SEQ ID NO:26.--.

Column 11, line 25, "of identical i sequences." should read --of identical sequences.--.

Column 11, line 60, "for the i polypeptide" should read --for the polypeptide--.

Column 12, line 44, "SEQ ED NO:18." should read --SEQ ID NO:18.--.

Column 13, line 12, "structure or" should read --structure) or--.

Column 13, line 21, "it hybridizes" should read --they hybridize--.

Column 13, lines 22-23, "18,20,25, 50,100, 150,200,300, 500, 550,750," should read --18, 20, 25, 50, 100, 150, 200, 300, 500, 550, 750,--.

Column 13, line 59, "MgC12" should read --MgCl$_2$--.

Column 14, line 6, "a Tm of" should read --a T$_m$ of--.

Column 14, line 14, "or hi vitro" should read --or in vitro--.

Column 14, line 35, "the generic" should read --the genetic--.

Column 18, line 25, "*P. paptasi*salivary gland" should read --*P. papatasi* salivary gland--.

Column 18, line 33, "cDNA SfiI A" should read --cDNA Sfi I A--.

Column 18, line 40, "K (0.8 ng/ul)" should read --K (0.8 μg/μl)--.

CERTIFICATE OF CORRECTION (continued)

Column 18, line 45, "SMART in and the CDs/3' primer)." should read --SMART III and the CDs/3' primer.)--.

Column 18, lines 49-50, "with i water" should read --with water--.

Column 18, line 54, "gold in from" should read --gold III from--.

Column 18, line 55, "(Cedar Creek, TE)" should read --(Cedar Creek, TX)--.

Column 18, line 62, "*P. paptasi*salivary gland" should read --*P. papatasi* salivary gland--.

Column 19, line 11, "minutes, 1 bold of" should read --minutes, 1 hold of--.

Column 19, line 59, "*P. papatasi*SP15-" should read --*P.papatasi* SP15- --.

Column 20, line 1, "transform TOP 10 cells" should read --transform TOP10 cells--.

Column 20, line 7, "PCP II vector" should read --PCRII vector--.

Column 20, line 21, "The VR1020plasmid" should read --The VR1020 plasmid--.

Column 20, line 27, "transform TOP 10 cells" should read --transform TOP10 cells--.

Column 21, lines 3-4, "of i the full-length" should read --of the full-length--.

Column 21, line 9, "*papatasi*salivary proteins." should read --*papatasi* salivary proteins.--.

Column 21, line 15, "www.morif.genome.ad.jp/." should read --www.motif.genome.ad.jp/.--.

Column 21, line 19, "degradation were estimated." should read --degradation was estimated--.

Column 21, line 31, "NCBI NR. protein" should read --NCBI NR protein--.

Column 21, line 35, "pi ranging" should read --pI ranging--.

Column 21, line 47, "heroin" should read --hemin--.

Column 22, line 25, "NaN," should read --NaN$_3$,--.

Column 23, line 9, "(FIG 5B." should read --(FIG 5B).--.

Column 23, line 19, "P. papatasi" should read --*P. papatasi*--.

Column 23, lines 27-28, "named SP15-PI. Control plasmids, i consisting of" should read --named SP15-P1. Control plasmids, consisting of--.

Column 23, line 30, "with SP15-PI," should read --with SP15-P1,--.

Column 23, line 35, "SP15-PI-immunized" should read --SP15-P1-immunized--.

Column 23, line 37, "with SP15-PI" should read --with SP15-P1--.

Column 23, line 44, "with SP15-PI on" should read --with SP15-P1 on--.

Column 23, line 45, "L. major infection" should read --*L. major* infection--.

Column 23, line 48, "CTL-PI" should read --CTL-P1--.

Column 23, line 51, "with SP15-PI" should read --with SP15-P1--.

Column 23, line 54, "CTL-PI" should read --CTL-P1--.

CERTIFICATE OF CORRECTION (continued)
U.S. Pat. No. 7,964,576 B2

Column 23, line 56, "the SP15-PI-" should read --the SP15-P1--.

Column 23, line 58, "CTL-PI" should read --CTL-P1--.

Column 23, line 61, "CTL-PI" should read --CTL-P1--.

Column 24, line 3, "SP15-PI" should read --SP15-P1--.

Column 24, line 7, "SP15-PI and CTL-PI" should read --SP15-P1 and CTL-P1--.

Column 24, line 10, "SP15-PI" should read --SP15-P1--.

Column 24, line 15, "blots, . (FIG. 9A)" should read --blots (FIG. 9A)--.

Column 24, line 20, "CTL-PI" should read --CTL-P1--.

Column 24, line 22, "SP15-PI" should read --SP15-P1--.

Column 26, line 38, "and antihistamimc activity" should read --and antihistaminic activity--.

SEQUENCE LISTING

```
<160> NUMBER OF SEQ ID NOS: 884

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct
<220> FEATURE:
<221> NAME/KEY: VARIANT
<222> LOCATION: 7
<223> OTHER INFORMATION: Xaa = can be any amino acid except Lys

<400> SEQUENCE: 1

Leu Asn Pro Ser Arg Lys Xaa Arg Leu Asp Tyr Lys Asp Lys Val Ile
 1               5                  10                  15

Ser Glu Ser

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 2

Phe Glu His Ala Glu Ala Phe Arg Ile Lys Lys His Asp Asp Thr Ile
 1               5                  10                  15

Phe Glu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct
<220> FEATURE:
<221> NAME/KEY: VARIANT
<222> LOCATION: 7
<223> OTHER INFORMATION: Xaa = can be any amino acid except Lys

<400> SEQUENCE: 3

Glu Pro Asn Ser Lys Lys Xaa Phe Glu Lys Phe Lys Asn Asp Ala Ser
 1               5                  10                  15

Lys Met Ala

<210> SEQ ID NO 4
<211> LENGTH: 19
<212> TYPE: PRT
```

```
<213> ORGANISM: Artificial Sequence
<220> FEATURE:
<223> OTHER INFORMATION: Description of Artificial Sequence; NOTE =
      Synthetic Construct
<220> FEATURE:
<221> NAME/KEY: VARIANT
<222> LOCATION: 17
<223> OTHER INFORMATION: Xaa = can be any amino acid except Lys

<400> SEQUENCE: 4

Trp Lys Tyr Pro Arg Asn Ala Asp Gln Thr Leu Trp Ala Phe Arg Thr
 1               5                  10                  15

Xaa Gln Arg

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct
<220> FEATURE:
<221> NAME/KEY: VARIANT
<222> LOCATION: 11
<223> OTHER INFORMATION: Xaa = can be any amino acid except Lys

<400> SEQUENCE: 5

Trp Arg Phe Pro Asn Gly Asp Gln Thr Tyr Xaa Ala Phe Asn Arg
 1               5                  10                  15

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 6

Ala Ser Thr Ile Pro Ile Gln Ser Gln Gly Lys Asp Phe Pro
 1               5                  10

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 7

Ala Pro Arg Ser Gly Thr Ile Tyr Asn Phe Ala Ile Ile Ala Asp Leu
 1               5                  10                  15

Asp Lys Lys

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct
<220> FEATURE:
<221> NAME/KEY: VARIANT
<222> LOCATION: 9
<223> OTHER INFORMATION: Xaa = can be any amino acid except Lys

<400> SEQUENCE: 8

Asp Asp Val Gly Arg Ala Tyr Glu Xaa Ser Glu Ile Lys Leu Val Gly
```

Val Arg Asn Pro
         20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct
<220> FEATURE:
<221> NAME/KEY: VARIANT
<222> LOCATION: 9, 11
<223> OTHER INFORMATION: Xaa = can be any amino acid except Lys

<400> SEQUENCE: 9

Asp Asp Val Glu Arg Phe Tyr Ala Xaa Arg Xaa Ile Thr Phe Glu Asp
 1               5                  10                  15

Val Lys Glu Gly
         20

<210> SEQ ID NO 10
<211> LENGTH: 140
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 10

Met Lys Tyr Phe Val Val Ala Leu Ile Ser Ala Val Phe Phe Ile Gly
 1               5                  10                  15

Ile Cys Gln Ala Leu Asn Pro Ser Arg Lys Cys Arg Leu Asp Tyr Lys
             20                  25                  30

Asp Lys Val Ile Ser Glu Ser Cys Ile Leu His Cys Glu Tyr Lys Ala
         35                  40                  45

Tyr Gly Phe Ala Asn Asp Lys Tyr Asp Ile Lys Arg Lys Gln Ile Asp
     50                  55                  60

Gln Phe Val Asp Val Leu Ile Asn Gly Lys Ala Val Ala Ser Asp Lys
65                  70                  75                  80

Arg Gln Lys Leu Glu Asn Leu Leu Arg Gly Cys Ala Asn Lys Ala Arg
                 85                  90                  95

Gly Lys Asn Pro Lys Leu Gly Cys His Thr Ser Ile Asp Tyr Tyr Arg
            100                 105                 110

Cys Ile Val Ala Asp Gln Lys Leu Ile Asn Tyr Ser Lys Phe Val Gly
        115                 120                 125

Ala Ile Ile Ala Tyr Asp Lys Lys Ile Asn Leu Asn
    130                 135                 140

<210> SEQ ID NO 11
<211> LENGTH: 142
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 11

Met Lys Tyr Leu Phe Ala Phe Val Ile Ile Pro Leu Leu Tyr Ala Glu
 1               5                  10                  15

Ile Ala Phe Gly Phe Glu His Pro Glu Ala Phe Cys Ile Lys Lys His
             20                  25                  30

```
Lys Asp Thr Asp Phe Glu Cys Ile Leu His Cys Lys Phe Lys Tyr Tyr
             35                  40                  45

Asn Phe Val Asp Asp Lys Tyr Asn Ile Lys Asp Tyr His Ile Arg Asn
 50                  55                  60

Leu Ala Asp Phe Leu Ile Asn Tyr Asn Val Val Pro Ala Asn Lys Arg
 65                  70                  75                  80

Arg Asn Val Glu Ala His Leu Arg Ser Cys Val Ala Lys Ser Ile Lys
                 85                  90                  95

Lys His Arg Thr Pro Ser Cys Asp Ser Ile Phe Ser Tyr Tyr Thr Cys
             100                 105                 110

Ile Thr Asp Glu Lys Leu Ile Tyr Phe Asn Asp Tyr Asp Asn Ala Ile
             115                 120                 125

Arg Arg Tyr Asp Gln Thr Leu Thr Val Val Thr Arg Lys Asn
130                 135                 140

<210> SEQ ID NO 12
<211> LENGTH: 142
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 12

Met Lys Tyr Leu Gly Leu Ala Leu Ile Ser Ala Val Phe Leu Ile Gly
 1               5                  10                  15

Thr Cys Gln Ala Glu Asn Pro Ser Lys Lys Cys Glu Glu Lys Phe Lys
                 20                  25                  30

Asn Asp Ala Ser Lys Met Ala Cys Ile Pro His Cys Lys Tyr Gln Tyr
             35                  40                  45

Tyr Gly Phe Val Ala Met Asp Asn Asn Ile Ala Lys Pro Glu Ile Arg
 50                  55                  60

Thr Phe Ser Asn Val Leu Ile Lys Tyr Asn Val Val Asp Lys Ser Leu
 65                  70                  75                  80

Lys Ala Asp Ile Arg Lys Ile Met His Glu Cys Ala Lys Lys Val Lys
                 85                  90                  95

Lys Gln Ala Arg Glu Asp Ser His Trp Leu Asn Cys Arg Thr Thr Ile
             100                 105                 110

Asn Tyr Tyr Arg Cys Ile Leu Thr Asp Lys Arg Ile Gly Pro Gln Arg
             115                 120                 125

Phe Asp Arg Ala Ile Gln Glu Tyr Asp Lys Thr Ile Asn Ile
130                 135                 140

<210> SEQ ID NO 13
<211> LENGTH: 254
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 13

Met Asn Ala Val Ile Thr Ser Leu Val Phe Leu Ser Leu Val Gly Leu
 1               5                  10                  15

Gly Tyr Ser Trp Lys Tyr Pro Arg Asn Ala Asp Gln Thr Leu Trp Ala
                 20                  25                  30

Phe Arg Thr Cys Gln Arg Arg Glu Ser Asp Asn Ile Leu Lys Lys
             35                  40                  45
```

```
Trp Tyr Thr Trp Glu Leu Pro Asn Asp Glu Lys Thr His Cys Tyr Val
    50                  55                  60

Lys Cys Val Trp Ile His Leu Gly Leu Tyr Ser Lys Asn Thr Lys Ser
 65                  70                  75                  80

Leu Arg Val Asn Lys Ile Glu Lys Gln Phe Thr Ser Arg Gly Val Ala
                 85                  90                  95

Ile Pro Ser Asp Leu Lys Ser Met Glu Gly Glu Thr Asp Gly Ser Cys
                100                 105                 110

Lys Ala Ile Tyr Asp Lys Thr Ile Ser Phe Phe Asn Asn Asn Val Ala
                115                 120                 125

Asp Leu Arg Thr Ala Phe Tyr Gly Thr Ile Glu Ser Asn Lys Trp
    130                 135                 140

Tyr Ala Gln Asn Pro Asp Val Lys Pro Lys Gly Thr Lys Ile Ser Lys
145                 150                 155                 160

Phe Cys Lys Ala Lys Asn Arg Glu Gln Gly Glu Ser Asn Cys Lys His
                165                 170                 175

Ala Cys Ser Ala Tyr Tyr Tyr Arg Leu Val Asp Glu Asp Phe Glu Pro
                180                 185                 190

Ile His Phe Arg Leu Leu Glu Ile Lys Gly Phe Ser Asn Glu Asp Ile
    195                 200                 205

Asp Glu Cys Thr Lys Gln Thr Ser Gly Gly Gln Gly Cys Gln Arg Ser
    210                 215                 220

Asp Ala Leu Tyr Asp Cys Leu Lys Asn Lys Lys Ser Ala Ala Leu Glu
225                 230                 235                 240

Ala Ala Leu Gln Ile Leu Asp Asp Gln Ser Ala Arg Thr Tyr
                245                 250

<210> SEQ ID NO 14
<211> LENGTH: 253
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 14

Met Lys Arg Val Val Gln Cys Leu Val Phe Phe Ser Ile Leu Gly Leu
  1               5                  10                  15

Gly Tyr Ser Trp Arg Phe Pro Arg Asn Gly Asp Gln Thr Tyr Trp Ala
                 20                  25                  30

Phe Asn Thr Cys Gln Arg Gln Thr Thr Asp Ile Glu Ser Val Lys Leu
                 35                  40                  45

Trp Asp Gln Trp Leu Leu Pro Asn Asn Ala Ala Thr His Cys Tyr Ile
    50                  55                  60

Lys Cys Val Phe Ile His Leu Gly Phe Tyr Asn Glu Gln Glu Lys Ala
 65                  70                  75                  80

Ile Asn Ile Asp Ala Val Lys Lys Gln Phe Lys Ser Arg Gly Leu Glu
                 85                  90                  95

Ile Pro Lys Asp Ile Lys Ser Leu Ser Gly Arg Thr Asp Gly Ser Cys
                100                 105                 110

Lys Ala Leu Tyr Glu Lys Thr Ile Pro Phe Phe Lys Asn Asn Phe Gln
                115                 120                 125

Asn Leu Arg Ile Ala Phe Tyr Gly Thr Arg Glu Glu Ser Asp Lys Trp
    130                 135                 140

Phe Ala Lys His Pro Glu Val Lys Pro Lys Arg Thr Arg Val Ser Glu
145                 150                 155                 160
```

```
Phe Cys Thr Ala Glu Lys Glu Lys Gly Glu Thr Lys Asn Cys Arg Arg
            165                 170                 175

Ala Cys Ser Leu Tyr Tyr Arg Phe Val Asp Glu Asp Tyr Gln Pro
            180                 185                 190

Ile Tyr Phe Arg Lys Leu Asp Ile Ala Gly Ile Thr Asp Lys Gln Ile
            195                 200                 205

Asn Asp Cys Arg Asp Lys Ala Arg Glu Lys Lys Gly Cys Lys Val Gly
            210                 215                 220

Asp Ala Leu Tyr Arg Cys Leu Arg Leu Ile Asn Lys Gln Gly Leu Ile
225                 230                 235                 240

Ala Thr Met Glu Arg Leu Asp Ile Glu Ser Trp Lys Tyr
            245                 250

<210> SEQ ID NO 15
<211> LENGTH: 246
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 15

Met Ser Gly His Ile Leu Thr Val Gly Leu Ile Val Val Ala His
 1               5                  10                  15

Cys Ala Thr Leu Ser Ser Ser Ala Ser Thr Ile Pro Ile Gln Ser Gln
            20                  25                  30

Gly Lys Asp Phe Pro Val Pro Phe Val Ser Glu Gln Thr Asp Asp Phe
            35                  40                  45

Tyr Asp Asp Lys Phe Tyr Pro Asp Ile Ser Asp Asn Ile Asn Glu
 50                  55                  60

Val Val Arg Asp Asn Gly Arg Lys Gly Gly Asp Arg Gly Ser Lys Ser
65                  70                  75                  80

Thr Pro Ser Gly Lys Glu Ser His Pro Thr Ala Thr Gln Thr Ser Gly
            85                  90                  95

Arg Arg Pro Ser Gln Ser Pro Cys Gly Glu Ser Arg Pro Ser Gly Ser
            100                 105                 110

Ala Thr Ser Gly Arg Arg Pro Ser Gln Ser Pro Arg Gly Glu Ser Leu
            115                 120                 125

Pro Pro Ala Thr Leu Ala Gly Arg Gln Asn Ser Arg Gln Gln Asp Arg
            130                 135                 140

Arg Gln Asn Lys Lys Gln Pro Asp Leu Ser Lys Tyr Lys Asn Ser Pro
145                 150                 155                 160

Ala Lys Tyr Ile Phe Thr Thr Gly Asn Val Asp Ser Gly Lys Thr Pro
            165                 170                 175

Asp Glu Glu Arg Ile Phe Arg Thr Asn Arg Ala Glu Tyr Val Leu Ala
            180                 185                 190

Thr Gly Gly Pro Tyr Asp Asn Tyr Val Val Glu Ile Ile Asp Gly Pro
            195                 200                 205

Asn Pro Asn Asp Ile Ser Leu Lys Gln Ser Thr Thr Met Gly Gly Asp
            210                 215                 220

Ser Lys Leu Ile Leu Asp Asn Pro Asn Arg Asn Thr Ile Val Gly Arg
225                 230                 235                 240

Ile Lys Thr Phe Lys Ala
            245

<210> SEQ ID NO 16
<211> LENGTH: 336
```

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 16

Met Phe Leu Lys Phe Cys Ile Val Ala Phe Ala Ile Cys Leu Ser Ile
 1               5                  10                  15

Asn Leu Ser Glu Gly Ala Pro Arg Ser Gly Thr Ile Tyr Asn Phe Ala
             20                  25                  30

Ile Ile Ala Asp Leu Asp Lys Lys Ser Ile Ser Pro Lys Asn Asp Asn
         35                  40                  45

Asn Tyr Lys Ser Ile Val Lys Val Gly Glu Leu Ile Glu Val Gly Asp
 50                  55                  60

Lys Tyr Ser Val Lys Met Lys Lys Glu Asp His Glu Ile Phe Thr Lys
 65                  70                  75                  80

Tyr Ala Tyr Lys Gly Arg Gly Ala Glu Leu Ser Glu Phe Leu Ile Tyr
                 85                  90                  95

Lys Trp Lys Leu Tyr Thr Phe Asp Asp Lys Ser Gly Ile Val Phe Arg
                100                 105                 110

Leu Lys Thr Asn Ala Asp Leu Ile Pro Trp Val Thr Leu Ala Asn Gly
            115                 120                 125

Asn Gly Asp Gln Thr Asp Gly Phe Lys Ala Glu Trp Ala Thr Thr Lys
130                 135                 140

Gly Asp Lys Met Tyr Val Gly Ser Thr Gly Ile Ser Phe Thr Asp Lys
145                 150                 155                 160

Thr Gly Lys Leu Asn Ser Asn Ser Leu Trp Ile Lys Glu Ile Asp Gln
                165                 170                 175

Asp Gly Lys Val Gln Ser Leu Asp Trp Lys Glu Gln Tyr Asp Lys Ile
            180                 185                 190

Lys Ser Ala Met Lys Ile Pro Asn Gly Phe Ile Trp His Glu Ala Val
        195                 200                 205

Asn Trp Ser Lys Leu Lys Asn Gln Trp Val Phe Leu Pro Arg Lys Cys
210                 215                 220

Ser Glu Arg Pro Phe Asp Thr Lys Thr Glu Glu Thr Ile Gly Cys Asn
225                 230                 235                 240

Lys Ile Ile Ile Ala Ser Glu Asn Phe Glu Ile Ile Lys Ser Ile Gln
                245                 250                 255

Ile Lys Gly Lys Ser Ile Asn Arg Ala Ala Gly Phe Ser Ser Phe Lys
            260                 265                 270

Phe Leu Pro Asp Ser Asp Gln Ile Leu Leu Ala Leu Lys Thr Ile
        275                 280                 285

Glu Lys Asp Asp Lys Thr Ala Thr Tyr Ile Thr Val Ile Asp Ile Thr
290                 295                 300

Gly Arg Val Leu Met Pro Glu Met Gln Ile Asn Ser Asp Lys Tyr Glu
305                 310                 315                 320

Gly Ile Val Leu Leu Lys Ser Thr Glu Gly Phe Leu Lys Arg Ser Gln
                325                 330                 335

<210> SEQ ID NO 17
<211> LENGTH: 394
<212> TYPE: PRT
<213> ORGANISM: Artificial Sequence
<220> FEATURE:
<223> OTHER INFORMATION: Description of Artificial Sequence; NOTE =
      Synthetic Construct
```

<400> SEQUENCE: 17

| | | | | | | | | | | | | | | |
|---|---|---|---|---|---|---|---|---|---|---|---|---|---|---|
|Met|Lys|Leu|Ile|Leu|Cys|Val|Leu|Ser|Phe|Leu|Ser|Leu|Gln|Val|Ala|
|1| | | |5| | | | |10| | | | |15| |

Leu Ser Asp Asp Val Gly Arg Ala Tyr Glu Trp Ser Glu Ile Lys Leu
                20                  25                  30

Val Gly Val Arg Pro Asn Ala Tyr Asp Ser Gly Asn Ile Val Pro Thr
            35                  40                  45

Gly Val Ala Tyr Asp Ala Ala Ser Lys Met Leu Phe Phe Gly Ile Pro
        50                  55                  60

Arg Ile Tyr Ser Arg Val Pro Ile Thr Phe Ala Gln Leu Ser Thr Arg
65                  70                  75                  80

Ser Tyr Asn Ser Ala Glu Ile Pro Asn Pro Pro Leu Asp Lys Phe Ser
                85                  90                  95

Gly Lys Ser Lys Gln Pro Leu Thr Ser Val Tyr Gln Pro Val Ile Asp
                100                 105                 110

Asp Cys Arg Arg Leu Trp Val Leu Asp Val Gly Ile Val Glu Asn Glu
            115                 120                 125

Ala Glu Arg Lys Thr Tyr Pro Ile Lys Lys Pro Ser Leu Ile Ala Phe
        130                 135                 140

Asp Leu Thr Lys Ser Asn Tyr Pro Glu Ile His Arg Tyr Glu Leu Thr
145                 150                 155                 160

Gly Glu Ala Gly Lys Asn Pro Leu Gly Tyr Gly Phe Ala Val Asp
                165                 170                 175

Val Val Asn Pro Lys Arg Cys Ser Asp Lys Asn Glu Lys Thr Tyr Ile
            180                 185                 190

Tyr Ile Ala Asn Phe Asp Glu Asn Ser Leu Ile Val Tyr Asp Lys Lys
        195                 200                 205

Lys Gly Glu Ala Trp Ser Leu Lys Asp Asp Ser Phe Lys Pro Glu Gly
        210                 215                 220

Val Thr Thr Phe Thr Leu Asn Gly Lys Glu His Lys Phe Lys Ala Gly
225                 230                 235                 240

Ile Phe Gly Ile Ala Leu Gly Asp Arg Asn Lys Glu Gly Asn Arg Pro
            245                 250                 255

Ala Tyr Tyr Leu Ala Gly Ser Ser Thr Lys Leu Tyr Arg Leu Asp Thr
        260                 265                 270

Lys Leu Leu Lys Lys Gly Ser Lys Leu Glu Pro Lys Leu Ile Gly
            275                 280                 285

Asp Arg Gly Phe Lys Thr Glu Ala Ile Ala Leu Ala Tyr Asp Pro Glu
        290                 295                 300

Thr Lys Val Leu Phe Phe Ala Glu Ala Asp Ser Arg Gln Val Ser Cys
305                 310                 315                 320

Trp Asn Ile Lys His Glu Leu Lys Pro Glu Asn Val Gly Val Ile Tyr
            325                 330                 335

Ala Asn Pro Asn Phe Asn Phe Gly Thr Asp Ile Met Val Asp Ser Lys
        340                 345                 350

Gly Phe Leu Trp Phe Met Ser Asn Gly Gln Pro Pro Ile Asp Glu Lys
        355                 360                 365

Met Glu Tyr Asp Val Pro Gln Ile Arg Leu Met Lys Val Lys Thr Lys
        370                 375                 380

Arg Ala Ile Lys Gly Glu Lys Cys Gln Gly
385                 390

<210> SEQ ID NO 18
<211> LENGTH: 400

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 18

Met Lys Phe Phe Leu Ser Val Ile Ala Leu Ala Ser Phe Gln Tyr Val
 1               5                  10                  15

Phe Cys Asp Asp Val Glu Arg Phe Tyr Ala Trp Arg Asn Ile Thr Phe
                20                  25                  30

Glu Asp Val Lys Glu Gly Thr Tyr Lys Pro Gly Asp Val Ile Pro Thr
            35                  40                  45

Gly Val Thr His Asp Ala Lys Thr Lys Lys Leu Tyr Phe Gly Val Pro
50                  55                  60

Arg Arg Tyr Ser Asn Ile Pro Tyr Thr Leu Ala Glu Ile Asp Thr Arg
65                  70                  75                  80

Asn Tyr Asn Arg Ser Glu Ile Arg Ser Pro Pro Phe Ser Lys Phe Asn
                85                  90                  95

Ser Gln Ser Gly Lys Glu Phe Thr Ser Ile Tyr Gln Pro Val Ile Asp
            100                 105                 110

Asp Cys Arg Arg Leu Trp Val Leu Asp Val Gly Gln Val Asp Tyr Lys
        115                 120                 125

Lys His Gly Asn Glu Tyr Pro Thr Lys Asn Pro Glu Ile Ile Ala Phe
130                 135                 140

Asp Leu Asn Gln Glu Gly Asn Pro Glu Val His Arg Tyr Lys Leu Glu
145                 150                 155                 160

Gly Asp Val Ala Arg Ser Pro Leu Gly Phe Gly Gly Phe Ala Val Asp
                165                 170                 175

Val Ile Asn Pro Asn Gly Asn Cys Ala Lys Ser Asp Glu Thr Tyr Leu
            180                 185                 190

Tyr Ile Thr Asn Phe Ile Asp Asn Ala Leu Ile Val Tyr Asp Met Lys
        195                 200                 205

Asn Lys Asn Ala Trp Lys Phe Asn Asp Asp Ser Phe Lys Pro Glu Pro
210                 215                 220

Gly Lys Ser Val Phe Asn His Lys Gly Glu Gln Tyr Ser Tyr Ile Ala
225                 230                 235                 240

Gly Ile Phe Gly Ile Thr Leu Gly Asp Arg Asn Lys Asp Gly His Arg
                245                 250                 255

Pro Ala Tyr Tyr Ile Ala Gly Ser Ser Thr Lys Val Tyr Ser Val Asn
            260                 265                 270

Thr Ala Ser Leu Lys Glu Lys Gly Ala Ser Leu Lys Pro Arg Leu Leu
        275                 280                 285

Gly Glu Arg Gly Phe Lys Thr Glu Ala Ile Ala Leu Ala Tyr Asp Pro
290                 295                 300

Lys Thr Lys Val Ile Phe Phe Val Glu Ser Asp Ser Arg Gln Val Ser
305                 310                 315                 320

Ala Trp Asn Ile Gln Lys Glu Leu Ile Pro Lys Asn Val Gly Val Ile
                325                 330                 335

Tyr Thr Asn Ala Tyr Phe Val Phe Gly Thr Asp Ile Met Val Asp Ala
            340                 345                 350

Asp Ser Thr Leu Trp Phe Met Ser Asn Ala His Pro Pro Thr Glu Leu
        355                 360                 365

Pro Lys Leu Asp Phe Asp Lys Arg Gln Ile Arg Leu Met Tyr Val Pro
370                 375                 380
```

Thr His Arg Ala Ile Arg Asn Leu Pro Cys Glu Val Arg Lys Pro Lys
385                 390                 395                 400

<210> SEQ ID NO 19
<211> LENGTH: 546
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 19

| | | | | | |
|---|---|---|---|---|---|
| aattcacttt | aaatctaatc | atgaaatact | tcgttgttgc | tttgatttct | gcagtattct | 60 |
| ttattggaat | ctgccaagct | ctcaatcctt | ctaggaaatg | taggttagac | tacaaagata | 120 |
| aggtcatatc | tgaatcatgc | atccttcact | gtgagtacaa | agcttacgga | tttgccaatg | 180 |
| ataaatacga | catcaagagg | aaacaaatcg | accaattcgt | tgatgttcta | attaatggaa | 240 |
| aagccgtggc | cagtgataag | aggcaaaaat | tggagaatct | tttaaggaga | tgcgcaaaca | 300 |
| aagcaagagg | caagaatccc | aaacttggat | gccatacaag | tattgactat | tacagatgca | 360 |
| ttgttgctga | tcaaaaattg | atcaactaca | gcaaatttgt | aggtgctatt | attgcctatg | 420 |
| acaaaaaaat | caatttaaac | taatgtacta | aatgtacaaa | aaatctaatt | gcttctgaaa | 480 |
| atctctcaat | aaaataaata | gaaaagctta | aaaaaaaaa | aaaaaaaaa | aaaaaaaaa | 540 |
| aaaaaa | | | | | | 546 |

<210> SEQ ID NO 20
<211> LENGTH: 512
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 20

| | | | | | |
|---|---|---|---|---|---|
| ggagttcaat | caatatgaag | tacttgttcg | cttttgtaat | aataccatta | ctctacgcag | 60 |
| aaattgcgtt | tgggtttgaa | catcccgaag | ccttctgcat | aaagaagcat | aaggatactg | 120 |
| attttgagtg | cattctccat | tgtaaattca | agtactacaa | ctttgttgat | gataagtaca | 180 |
| acattaagga | ctatcacatt | cggaatttag | ctgacttctt | gattaattac | aatgtggttc | 240 |
| ctgctaacaa | aaggagaaat | gtggaggcac | atcttagatc | ctgtgtggcc | aaatcaatta | 300 |
| aaaagcatag | aacaccgagt | tgtgatagta | ttttcagtta | ttatacgtgc | ataactgatg | 360 |
| aaaagttgat | ctactttaat | gactacgata | acgcaattag | gcgttacgac | caaacgctta | 420 |
| ctgttgtaac | tagaaagaac | tagaagttga | aatataataa | catttgcaaa | ctttgaactt | 480 |
| taaaaaaaaa | aaaaaaaaa | aaaaaaaaa | aa | | | 512 |

<210> SEQ ID NO 21
<211> LENGTH: 522
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 21

| | | | | | |
|---|---|---|---|---|---|
| gagttttaat | tacgaccatg | aagtacttag | gacttgcttt | aatttccgca | gtgttcttaa | 60 |
| ttggaacctg | ccaagctgaa | aatccatcaa | agaagtgcga | ggaaaaattt | aagaatgatg | 120 |
| cttcgaaaat | ggcttgcatt | ccccattgca | aatatcagta | ttacggattt | gtagctatgg | 180 |

```
ataataacat cgctaaacca gagattagaa cattttctaa tgttctaatc aaatataatg      240
ttgtggacaa aagcctgaaa gcagacatta ggaaaattat gcacgaatgt gctaaaaaag      300
ttaagaaaca agctagagaa gactctcatt ggttgaattg tcgtacaact attaattatt      360
atagatgtat tttgaccgac aaacgaattg gacctcaaag atttgacaga gccattcaag      420
aatatgataa acaatcaat atataaccac aaaatttata cttaaataaa gcttgaaagc       480
actgaagttg ctttcccaaa aaaaaaaaaa aaaaaaaaaa aa                         522
```

<210> SEQ ID NO 22
<211> LENGTH: 878
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 22

```
ggcagtgcga ttgtgaaaat gaatgctgtg attacaagtt tggtttttct aagccttgtt       60
ggactagggt attcttggaa gtaccctagg aatgccgatc aaactctttg gcttttaga       120 acttgtcaaa ggcgggaatc tgataataat atacttaaaa aatggtatac atgggaatta      180
ccaaatgatg agaaaaccca ctgctacgtc aaatgtgttt ggattcatct gggactttac      240
agtaaaaata caaagtcact cagggttaac aagattgaga agcaattcac cagtcgtggg      300
gttgcgattc cttcggattt aaaaagtatg gaaggtgaaa cagatggatc gtgtaaagct      360
atatacgata aaaccattag cttctttaat aataatgtgg cagacttacg cactgccttc      420
tatggtacaa tagaggaatc gaataagtgg tatgcgcaaa accctgatgt caaaccgaaa      480
ggaaccaaga tttcgaaatt ctgtaaagct aaaaatagag aacaaggaga agcaattgc       540 aagcatgcat gtagtgctta ttattatcgc ttggttgatg aggacttcga acctatacac      600
tttagactat tggaaataaa gggttttca aatgaagaca ttgacgaatg cacaaagcag       660
acaagtggag gtcaaggatg ccaaaggtct gatgcgttgt atgattgctt gaaaaataaa      720
aaatcagcag ctttagaagc agctttacag attctcgatg accaatccgc aagaacgtac     780
taggaaaaat gtacaataag ataccataat tttttgatgt cttgtttcgg aaataaagaa     840
attaaaagcg aaaaaaaaaa aaaaaaaaaa aaaaaaaa                              878
```

<210> SEQ ID NO 23
<211> LENGTH: 858
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 23

```
gccggggaaa tcagtttcat cttgcaaaat gaagagagtg gttcaatgtt tggttttctt       60
cagtattctt ggattaggat attcttggcg atttcctagg aatggagacc aaacttattg      120
ggcttttaat acttgtcaaa gacaaactac ggacattgag tctgttaaat tgtgggatca      180
atggttatta ccaaacaatg ccgcaacaca ttgttacatc aaatgtgttt ttattcatct      240
gggattctat aatgaacagg agaaagctat taacattgat gctgtcaaaa agcaattaa       300 gagtcgtggc ttagaaattc ctaaggatat aaaaagtttg tctggtcgaa cagatggatc     360
ttgtaaagcg ttgtatgaaa agactatacc attcttcaaa aacaattttc aaaatttgag     420
gattgccttc tatggaacaa gagaagagtc agataagtgg ttcgcgaaac atcctgaagt     480
```

```
taaaccaaag cgaacaaggg tttcggaatt ttgtactgcc gaaaaagaaa aaggagaaac    540
taagaattgc agacgtgcat gtagtcttta ctattaccgt tttgttgacg aagactatca    600
accaatatac tttaggaaat tggatattgc tggtatcaca gataaacaaa ttaacgattg    660
cagagataag gcgagagaaa aaaaaggatg caaagtgggt gacgcgttgt atagatgctt    720
aaggcttatt aataagcagg gtttaatagc aactatggaa agacttgata ttgaatcttg    780
gaaatactaa ttttttttgta aacaagtttc atttgagaac tatatgaaat acaatgtgtt    840
ggaaagccaa aaaaaaaa                                                   858

<210> SEQ ID NO 24
<211> LENGTH: 862
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 24
acagcatttt gtggaaaatc taggaaaaat gtcaggacat attttaacag tgggtctaat     60
tgtggtagtg gcacattgtg ctactttatc tagttccgca agcacaattc ccattcagag    120
tcaaggaaaa gattttcctg ttccgtttgt ttccgaacaa actgatgatt tttacgacga    180
taaattttat cccgatatca gtgatgataa cataaatgaa gtagtaagag ataacgggcg    240
taaaggtggt gatcggggta gcaaatcgac accttcaggg aaagaatccc atcctacagc    300
cactcaaact agtggtagga gaccatcgca atctccatgc ggagaatcgc gtccttcggg    360
atctgcaact agtggcagaa gaccatcgca atctccaagg ggagaatcgc ttcctccagc    420
cactttagct ggtaggcaaa attctaggca gcaagacaga aggcagaata aaaagcaacc    480
agatctatca aaatataaga attctcctgc taaatatata ttcacaacag gaaatgtcga    540
ttctggcaaa actcctgatg aggaaagaat ttcagaact aatagggcag aatatgtcct    600
tgcaacaggt ggcccctatg ataactatgt ggtggagata attgacggtc caaatccaaa    660
tgatatcagt ttgaagcaat caacaacaat gggtggtgat agcaaattaa tcctcgataa    720
tccaaatcgt aacacaattg ttggacgtat caaaactttc aaggcttgag aaaagaggaa    780
attaagcatg aggttattct ttttttctgt ttacttaaaa cttccaataa ataaaaaaaa    840
aaaaaaaaaa aaaaaaaaaa aa                                              862

<210> SEQ ID NO 25
<211> LENGTH: 1065
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 25
gccggggatt ctgttgtggg aaatctcttg aacattttca aaatgtttct caaattttgt     60
attgttgctt ttgccatttg cctctcaata aatctctcag aaggagctcc aagaagtgga    120
acaatctata attttgccat tatagctgat ttggataaaa aatctatcag cccaaagaat    180
gataataatt acaaaagtat cgtgaaagtg ggtgaattga ttgaagtagg agataagtac    240
agtgtcaaaa tgaagaaaga agatcatgaa atattcacta aatatgcata caaaggacga    300
ggagctgaat tatctgaatt cttaatttat aaatggaaac tttacacttt tgatgacaaa    360
agtggaattg tctttagact gaaaaccaat gcagacctca ttccttgggt aactctcgca    420
```

```
aatggcaatg gagatcaaac tgatggcttt aaggcagaat gggcaacaac taaaggtgac      480
aaaatgtacg ttggatcaac tggaatttct tttactgaca aaacaggcaa attaaatagc      540
aactccctct ggatcaaaga aatcgatcaa gacggaaagg ttcagagttt agattggaaa      600
gaacaatacg acaaaataaa aagtgctatg aaaatcccta atggattyat ttggcacgaa      660
gctgttaatt ggtcaaaact caaaaaccaa tgggtctttc taccaagaaa atgctcagaa      720
cgtccatttg ataccaaaac tgaagagact attggatgta acaagataat cattgccagt      780
gaaaatttcg aaataatcaa atctattcag atcaaaggaa atctattaa tcgtgccgca      840 ggattttctt cattcaaatt cctccccgat agtgatgacc aaatccttct tgcattgaag      900
actatcgaaa aggacgacaa aactgctaca tacattacag taattgatat cactggaaga      960
gttttaatgc cagaaatgca gatcaatagc gataaatacg aaggaattgt gcttttgaaa     1020
agcaccgaag gattttgaa acgcagtcaa taataaaaaa aaaaa                      1065
```

<210> SEQ ID NO 26
<211> LENGTH: 1330
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 26

```
agtcagttgt gttgtgacgg atttatgatg aagttgattt tgtgtgttct atcctttcta       60
tctctccaag tggctctttc cgatgatgtt ggaagggctt atgaatggag tgaaattaaa      120
ttagtgggag ttaggccaaa tgcttacgat tcaggaaata ttgtaccaac tggagtagct      180
tatgatgcag ctagcaaaat gcttttcttc ggaataccaa gaatatattc gagagtacca      240
attacttttg ctcaacttag tacacgtagt tacaattcag ctgaatacct aaccctccac      300
ttgataaatt cagtggaaag agtaaacagc cattgcatc agtctatcaa cctgtgatcg      360
atgattgccg tagactttgg gttctcgatg ttggaatagt ggaaaacgag gctgaacgaa      420
agacatatcc catcaaaaaa ccatcactta tcgcctttga cctaacaaaa tcaaactatc      480
cagaaattca ccgttacgaa ttgactggtg aagctggaaa gaatcctcta ggatacggag      540
gatttgctgt tgacgttgtc aatcccaaac gttgtagcga caaaaatgaa aaaacatata      600
tctacattgc aaactttgat gaaaattcct taattgtgta tgataaaaag aaaggcgagg      660
cctggagctt gaaagatgac tcatttaaac ctgaaggtgt cactacattt acacttaacg      720
gcaaggaaca taagtttaaa gctggaatat tcggaatagc cctgggtgac aggaataaag      780
aaggaaaccg tccagcttac tatttggcag gatccagcac aaagctatac agactcgata      840
ctaagttact caagaagaag ggttcaaaat tagaacctaa acttatagga gatcgtggtt      900
ttaaaaccga agccattgcc ttggcttatg atcctgaaac taaggttctc ttctttgctg      960
aagcagactc tagacaggtt tcatgctgga atattaagca cgaacttaag cctgagaacg     1020
ttggtgtaat ttacgccaat cctaacttca attttggcac agacattatg gttgacagta     1080
aaggattcct ttggttcatg tcaaatggtc agccaccaat tgacgagaaa atggagtatg     1140
atgtacctca aattcgtttg atgaaggtga aaactaaaag agcaattaaa ggagaaaagt     1200
gtcaagggta taagaaagc tatatatctg tctatctaaa tatctgatgg gatatcagct     1260
ttgagttatc aataaattga aaacgaaat gattattcta aaaaaaaaa aaaaaaaaaa     1320 aaaaaaaaaa                                                             1330
```

```
<210> SEQ ID NO 27
<211> LENGTH: 1313
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 27
agttcattcc gacgactcta taatgaagtt cttttttgagt gttattgctt tagcatcttt      60
tcaatatgtt ttctgtgacg atgttgaaag attttacgca tggagaaata aacttttga     120 agacgtaaaa gaaggtacct ataagccagg agatgtcata ccaactggag ttactcatga     180
tgcgaaaacc aagaaacttt actttggagt tccaagacga tattccaata ttccatacac     240
acttgctgaa attgacactc gcaactataa tcgatctgaa atacgttctc ctccgttcag     300
taaattcaat agtcaaagtg gtaaagaatt cacatcgatt tatcaaccag tgattgatga     360
ttgtcgtaga ctttgggttc tcgatgttgg acaagtggac tataaaaaac atggaaatga     420
atatccaacg aaaaaccccg aaattatcgc tttcgatctt aatcaagaag gaaatccgga     480
agtacatcga tataaattag aaggtgatgt tgcacgatct ccactaggtt ttggaggatt     540
tgccgttgat gtaataaacc caaatggaaa ttgtgccaaa tccgatgaaa cttatcttta     600
tattacgaat tttattgata cgctcttat tgtgtatgac atgaagaata agaatgcatg     660
gaaatttaat gacgattcgt tcaagccaga accagggaag tccgtattta atcataaagg     720
cgaacaatat tcctatatcg caggaatatt tggtataact ctgggagata ggaacaagga     780
cggacaccga ccagcttatt atatagcagg atcgagcaca aaggtctaca gtgtcaatac     840
cgcatctcta aaggaaaagg gtgcatctct taaaccaaga ttactaggag aacgtggttt     900
taaaacagaa gccattgcac ttgcttacga tccaaagact aaagtcatct tcttcgttga    960
atctgatagc agacaagtgt ctgcctggaa tatacaaaag gaattaatac ctaaaaatgt    1020
tggcgttatt tatacaaatg cctatttttgt gtttggaaca gatataatgg ttgatgctga    1080
ttccactctg tggtttatgt ctaatgctca tcccccaaca gaactaccca aattggactt    1140
cgataagcgc caaattcgtt taatgtacgt accaacacac cgcgcaattc gtaatctacc    1200
gtgtgaagtg agaaaaccta aataaaaagc tctgcttaag aattagtgca tacaaatcaa    1260
tatgtacttt ataagtcaa gaaaataaaa gcattttcaa aaaaaaaaa aaa            1313

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 28

Arg Gly Lys Asn Pro Lys Leu
  1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 29

Arg Gly Cys Ala Asn Lys Ala
```

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 30

Lys Ala Val Ala Ser Asp Lys Arg
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 31

Lys Lys Ile Asn Leu Asn
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 32

Lys Tyr Asp Ile Lys Arg Lys
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 33

Lys Leu Ile Asn Tyr Ser Lys Phe
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 34

Lys Ala Val Ala Ser Asp Lys Arg Gln
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

```
<400> SEQUENCE: 35

Lys Leu Glu Asn Leu Leu Arg Gly
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 36

Lys Ala Arg Gly Lys Asn Pro Lys Leu
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 37

Arg Leu Asp Tyr Lys Asp Lys Val
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 38

Arg Gly Cys Ala Asn Lys Ala Arg Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 39

Lys Tyr Asp Ile Lys Arg Lys Gln
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 40

Arg Cys Ile Val Ala Asp Gln Lys Leu
1               5

<210> SEQ ID NO 41
<211> LENGTH: 8
<212> TYPE: PRT
```

```
<213> ORGANISM: Artificial Sequence
<220> FEATURE:
<223> OTHER INFORMATION: Description of Artificial Sequence; NOTE =
      Synthetic Construct

<400> SEQUENCE: 41

Lys Cys Arg Leu Asp Tyr Lys Asp
1               5

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 42

Lys Ala Tyr Gly Phe Ala Asn Asp Lys Tyr
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 43

Arg Gly Cys Ala Asn Lys Ala Arg Gly Lys Asn
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 44

Arg Lys Cys Arg Leu Asp Tyr Lys Asp
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 45

Arg Gln Lys Leu Glu Asn Leu Leu Arg Gly
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 46

Lys Ala Val Ala Ser Asp Lys Arg Gln Lys Leu
1               5                   10
```

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 47

Arg Gln Lys Leu Glu Asn Leu Leu Arg Gly
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 48

Lys Phe Val Gly Ala Ile Ile Ala Tyr Asp Lys Lys
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 49

Lys Cys Arg Leu Asp Tyr Lys Asp Lys Val
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 50

Lys Arg Gln Lys Leu Glu Asn Leu Leu Arg Gly
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 51

Lys Phe Val Gly Ala Ile Ile Ala Tyr Asp Lys Lys Ile
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 52

```
Lys Leu Glu Asn Leu Leu Arg Gly Cys Ala Asn Lys Ala
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 53

Lys Leu Gly Cys His Thr Ser Ile Asp Tyr Tyr Arg Cys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 54

Lys Ala Tyr Gly Phe Ala Asn Asp Lys Tyr Asp Ile Lys Arg
1               5                   10

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 55

Lys Gln Ile Asp Gln Phe Val Asp Val Leu Ile Asn Gly Lys Ala
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 56

Lys Gln Ile Asp Gln Phe Val Asp Val Leu Ile Asn Gly Lys Ala
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 57

Lys Leu Glu Asn Leu Leu Arg Gly Cys Ala Asn Lys Ala Arg Gly
1               5                   10                  15

<210> SEQ ID NO 58
<211> LENGTH: 15
<212> TYPE: PRT
<213> ORGANISM: Artificial Sequence
<220> FEATURE:
```

<223> OTHER INFORMATION: Description of Artificial Sequence; NOTE =
      Synthetic Construct

<400> SEQUENCE: 58

Arg Gln Lys Leu Glu Asn Leu Leu Arg Gly Cys Ala Asn Lys Ala
 1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 59

Arg Gln Lys Leu Glu Asn Leu Leu Arg Gly Cys Ala Asn Lys Ala
 1               5                  10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 60

Lys Ala Tyr Gly Phe Ala Asn Asp Lys Tyr Asp Ile Lys Arg Lys
 1               5                  10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 61

Arg Cys Ile Val Ala Asp Gln Lys Leu Ile Asn Tyr Ser Lys Phe
 1               5                  10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 62

Arg Lys Gln Ile Asp Gln Phe Val Asp Val Leu Ile Asn Gly Lys Ala
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 63

Lys Val Ile Ser Glu Ser Cys Ile Leu His Cys Glu Tyr Lys Ala
 1               5                  10                  15

<210> SEQ ID NO 64

```
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 64

Lys Phe Val Gly Ala Ile Ile Ala Tyr Asp Lys Lys Ile Asn Leu Asn
 1               5                  10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 65

Lys Asn Pro Lys Leu Gly Cys His Thr Ser Ile Asp Tyr Tyr Arg Cys
 1               5                  10                  15

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 66

Lys Arg Lys Gln Ile Asp Gln Phe Val Asp Val Leu Ile Asn Gly Lys
 1               5                  10                  15

Ala

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 67

Lys Leu Ile Asn Tyr Ser Lys Phe Val Gly Ala Ile Ile Ala Tyr Asp
 1               5                  10                  15

Lys Lys

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 68

Lys Asp Lys Val Ile Ser Glu Ser Cys Ile Leu His Cys Glu Tyr Lys
 1               5                  10                  15

Ala

<210> SEQ ID NO 69
<211> LENGTH: 18
<212> TYPE: PRT
<213> ORGANISM: Artificial Sequence
<220> FEATURE:
```

-continued

```
<223> OTHER INFORMATION: Description of Artificial Sequence; NOTE =
      Synthetic Construct

<400> SEQUENCE: 69

Arg Gly Lys Asn Pro Lys Leu Gly Cys His Thr Ser Ile Asp Tyr Tyr
1               5                   10                  15

Arg Cys

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 70

Lys Leu Ile Asn Tyr Ser Lys Phe Val Gly Ala Ile Ile Ala Tyr Asp
1               5                   10                  15

Lys Lys Ile

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 71

Lys Gln Ile Asp Gln Phe Val Asp Val Leu Ile Asn Gly Lys Ala Val
1               5                   10                  15

Ala Ser Asp Lys Arg
            20

<210> SEQ ID NO 72
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 72

Lys Gln Ile Asp Gln Phe Val Asp Val Leu Ile Asn Gly Lys Ala Val
1               5                   10                  15

Ala Ser Asp Lys Arg
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 73

Arg Lys Gln Ile Asp Gln Phe Val Asp Val Leu Ile Asn Gly Lys Ala
1               5                   10                  15

Val Ala Ser Asp Lys Arg
            20

<210> SEQ ID NO 74
<211> LENGTH: 22
```

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 74

Lys Gln Ile Asp Gln Phe Val Asp Val Leu Ile Asn Gly Lys Ala Val
1               5                   10                  15

Ala Ser Asp Lys Arg Gln
            20

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 75

Lys Gln Ile Asp Gln Phe Val Asp Val Leu Ile Asn Gly Lys Ala Val
1               5                   10                  15

Ala Ser Asp Lys Arg Gln
            20

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 76

Lys Leu Gly Cys His Thr Ser Ile Asp Tyr Tyr Arg Cys Ile Val Ala
1               5                   10                  15

Asp Gln Lys Leu
            20

<210> SEQ ID NO 77
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 77

Arg Leu Asp Tyr Lys Asp Lys Val Ile Ser Glu Ser Cys Ile Leu His
1               5                   10                  15

Cys Glu Tyr Lys Ala
            20

<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 78

Lys Val Ile Ser Glu Ser Cys Ile Leu His Cys Glu Tyr Lys Ala Tyr
1               5                   10                  15

Gly Phe Ala Asn Asp Lys Tyr
```

-continued

```
                    20

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 79

Lys Asn Pro Lys Leu Gly Cys His Thr Ser Ile Asp Tyr Tyr Arg Cys
1               5                   10                  15

Ile Val Ala Asp Gln Lys Leu
            20

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 80

Lys Tyr Phe Val Val Ala Leu Ile Ser Ala Val Phe Phe Ile Gly Ile
1               5                   10                  15

Cys Gln Ala Leu Asn Pro Ser Arg Lys
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 81

Arg Cys Ile Val Ala Asp Gln Lys Leu Ile Asn Tyr Ser Lys Phe Val
1               5                   10                  15

Gly Ala Ile Ile Ala Tyr Asp Lys Lys
            20                  25

<210> SEQ ID NO 82
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 82

Lys Tyr Phe Val Val Ala Leu Ile Ser Ala Val Phe Phe Ile Gly Ile
1               5                   10                  15

Cys Gln Ala Leu Asn Pro Ser Arg Lys Cys
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 83
```

```
Lys Tyr Phe Val Val Ala Leu Ile Ser Ala Val Phe Phe Ile Gly Ile
1               5                   10                  15

Cys Gln Ala Leu Asn Pro Ser Arg Lys
            20                  25
```

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 84

```
Lys Asp Lys Val Ile Ser Glu Ser Cys Ile Leu His Cys Glu Tyr Lys
1               5                   10                  15

Ala Tyr Gly Phe Ala Asn Asp Lys Tyr
            20                  25
```

<210> SEQ ID NO 85
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 85

```
Met Lys Tyr Phe Val Val Ala Leu Ile Ser Ala Val Phe Phe Ile Gly
1               5                   10                  15

Ile Cys Gln Ala Leu Asn Pro Ser Arg Lys
            20                  25
```

<210> SEQ ID NO 86
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 86

```
Met Lys Tyr Phe Val Val Ala Leu Ile Ser Ala Val Phe Phe Ile Gly
1               5                   10                  15

Ile Cys Gln Ala Leu Asn Pro Ser Arg Lys
            20                  25
```

<210> SEQ ID NO 87
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 87

```
Lys Tyr Phe Val Val Ala Leu Ile Ser Ala Val Phe Phe Ile Gly Ile
1               5                   10                  15

Cys Gln Ala Leu Asn Pro Ser Arg Lys Cys
            20                  25
```

<210> SEQ ID NO 88
<211> LENGTH: 26
<212> TYPE: PRT
<213> ORGANISM: Artificial Sequence

```
<220> FEATURE:
<223> OTHER INFORMATION: Description of Artificial Sequence; NOTE =
      Synthetic Construct

<400> SEQUENCE: 88

Lys Leu Gly Cys His Thr Ser Ile Asp Tyr Tyr Arg Cys Ile Val Ala
 1               5                  10                  15

Asp Gln Lys Leu Ile Asn Tyr Ser Lys Phe
            20                  25

<210> SEQ ID NO 89
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 89

Met Lys Tyr Phe Val Val Ala Leu Ile Ser Ala Val Phe Phe Ile Gly
 1               5                  10                  15

Ile Cys Gln Ala Leu Asn Pro Ser Arg Lys Cys
            20                  25

<210> SEQ ID NO 90
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 90

Met Lys Tyr Phe Val Val Ala Leu Ile Ser Ala Val Phe Phe Ile Gly
 1               5                  10                  15

Ile Cys Gln Ala Leu Asn Pro Ser Arg Lys Cys
            20                  25

<210> SEQ ID NO 91
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 91

Lys Val Ile Ser Glu Ser Cys Ile Leu His Cys Glu Tyr Lys Ala Tyr
 1               5                  10                  15

Gly Phe Ala Asn Asp Lys Tyr Asp Ile Lys Arg
            20                  25

<210> SEQ ID NO 92
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 92

Lys Tyr Phe Val Val Ala Leu Ile Ser Ala Val Phe Phe Ile Gly Ile
 1               5                  10                  15

Cys Gln Ala Leu Asn Pro Ser Arg Lys Cys Arg Leu
            20                  25
```

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 93

Arg Ser Cys Val Ala Lys Ser
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 94

Lys Asp Tyr His Ile Arg Asn
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 95

Lys Ser Ile Lys Lys His Arg Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 96

Arg Asn Val Glu Ala His Leu Arg Ser
1               5

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 97

Arg Ser Cys Val Ala Lys Ser Ile Lys Lys
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 98

Arg Arg Asn Val Glu Ala His Leu Arg Ser
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 99

Arg Ser Cys Val Ala Lys Ser Ile Lys Lys His
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 100

Lys Tyr Tyr Asn Phe Val Asp Asp Lys Tyr
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 101

Lys Arg Arg Asn Val Glu Ala His Leu Arg Ser
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 102

Arg Tyr Asp Gln Thr Leu Thr Val Val Thr Arg Lys
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 103

Lys Tyr Asn Ile Lys Asp Tyr His Ile Arg Asn
1               5                   10

<210> SEQ ID NO 104
<211> LENGTH: 13
<212> TYPE: PRT
<213> ORGANISM: Artificial Sequence
<220> FEATURE:

```
<223> OTHER INFORMATION: Description of Artificial Sequence; NOTE =
      Synthetic Construct

<400> SEQUENCE: 104

Arg Tyr Asp Gln Thr Leu Thr Val Val Thr Arg Lys Asn
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 105

Lys Phe Lys Tyr Tyr Asn Phe Val Asp Asp Lys Tyr
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 106

Arg Arg Tyr Asp Gln Thr Leu Thr Val Val Thr Arg Lys
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 107

Arg Asn Val Glu Ala His Leu Arg Ser Cys Val Ala Lys Ser
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 108

Arg Tyr Asp Gln Thr Leu Thr Val Val Thr Arg Lys Asn
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 109

Lys Asp Thr Asp Phe Glu Cys Ile Leu His Cys Lys Phe
1               5                   10

<210> SEQ ID NO 110
```

```
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 110

Arg Arg Tyr Asp Gln Thr Leu Thr Val Val Thr Arg Lys Asn
 1               5                  10

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 111

Lys Leu Ile Tyr Phe Asn Asp Tyr Asp Asn Ala Ile Arg Arg
 1               5                  10

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 112

Arg Arg Asn Val Glu Ala His Leu Arg Ser Cys Val Ala Lys Ser
 1               5                  10                  15

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 113

Lys Tyr Tyr Asn Phe Val Asp Asp Lys Tyr Asn Ile Lys Asp
 1               5                  10

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 114

Lys Leu Ile Tyr Phe Asn Asp Tyr Asp Asn Ala Ile Arg Arg Tyr
 1               5                  10                  15

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 115

Arg Asn Val Glu Ala His Leu Arg Ser Cys Val Ala Lys Ser Ile Lys
 1               5                  10                  15
```

```
                 1               5                  10                  15
Lys

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 116

Lys His Lys Asp Thr Asp Phe Glu Cys Ile Leu His Cys Lys Phe
 1               5                  10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 117

Lys Asp Thr Asp Phe Glu Cys Ile Leu His Cys Lys Phe Lys Tyr
 1               5                  10                  15

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 118

Arg Asn Leu Ala Asp Phe Leu Ile Asn Tyr Asn Val Val Pro Ala Asn
 1               5                  10                  15

Lys Arg

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 119

Lys Phe Lys Tyr Tyr Asn Phe Val Asp Asp Lys Tyr Asn Ile Lys Asp
 1               5                  10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 120

Lys Lys His Lys Asp Thr Asp Phe Glu Cys Ile Leu His Cys Lys Phe
 1               5                  10                  15

<210> SEQ ID NO 121
<211> LENGTH: 19
<212> TYPE: PRT
```

```
<213> ORGANISM: Artificial Sequence
<220> FEATURE:
<223> OTHER INFORMATION: Description of Artificial Sequence; NOTE =
      Synthetic Construct

<400> SEQUENCE: 121

Arg Asn Leu Ala Asp Phe Leu Ile Asn Tyr Asn Val Val Pro Ala Asn
 1               5                  10                  15

Lys Arg Arg

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 122

Lys His Lys Asp Thr Asp Phe Glu Cys Ile Leu His Cys Lys Phe Lys
 1               5                  10                  15

Tyr

<210> SEQ ID NO 123
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 123

Arg Asn Leu Ala Asp Phe Leu Ile Asn Tyr Asn Val Val Pro Ala Asn
 1               5                  10                  15

Lys Arg Arg Asn
            20

<210> SEQ ID NO 124
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 124

Arg Thr Pro Ser Cys Asp Ser Ile Phe Ser Tyr Tyr Thr Cys Ile Thr
 1               5                  10                  15

Asp Glu Lys Leu
            20

<210> SEQ ID NO 125
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 125

Lys Tyr Tyr Asn Phe Val Asp Asp Lys Tyr Asn Ile Lys Asp Tyr His
 1               5                  10                  15

Ile Arg Asn

<210> SEQ ID NO 126
```

```
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 126

Lys Asp Tyr His Ile Arg Asn Leu Ala Asp Phe Leu Ile Asn Tyr Asn
1               5                   10                  15

Val Val Pro Ala Asn Lys Arg
            20

<210> SEQ ID NO 127
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 127

Lys His Arg Thr Pro Ser Cys Asp Ser Ile Phe Ser Tyr Tyr Thr Cys
1               5                   10                  15

Ile Thr Asp Glu Lys Leu
            20

<210> SEQ ID NO 128
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 128

Lys Lys His Arg Thr Pro Ser Cys Asp Ser Ile Phe Ser Tyr Tyr Thr
1               5                   10                  15

Cys Ile Thr Asp Glu Lys Leu
            20

<210> SEQ ID NO 129
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 129

Lys Asp Tyr His Ile Arg Asn Leu Ala Asp Phe Leu Ile Asn Tyr Asn
1               5                   10                  15

Val Val Pro Ala Asn Lys Arg Arg
            20

<210> SEQ ID NO 130
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 130

Lys Asp Thr Asp Phe Glu Cys Ile Leu His Cys Lys Phe Lys Tyr Tyr
1               5                   10                  15
```

```
Asn Phe Val Asp Asp Lys Tyr
            20
```

<210> SEQ ID NO 131
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 131

```
Lys Leu Ile Tyr Phe Asn Asp Tyr Asp Asn Ala Ile Arg Arg Tyr Asp
 1               5                  10                  15

Gln Thr Leu Thr Val Val Thr Arg Lys
            20                  25
```

<210> SEQ ID NO 132
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 132

```
Lys Tyr Asn Ile Lys Asp Tyr His Ile Arg Asn Leu Ala Asp Phe Leu
 1               5                  10                  15

Ile Asn Tyr Asn Val Val Pro Ala Asn Lys Arg
            20                  25
```

<210> SEQ ID NO 133
<211> LENGTH: 30
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 133

```
Lys Tyr Leu Phe Ala Phe Val Ile Ile Pro Leu Leu Tyr Ala Glu Ile
 1               5                  10                  15

Ala Phe Gly Phe Glu His Pro Glu Ala Phe Cys Ile Lys Lys
            20                  25                  30
```

<210> SEQ ID NO 134
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 134

```
Lys Tyr Leu Phe Ala Phe Val Ile Ile Pro Leu Leu Tyr Ala Glu Ile
 1               5                  10                  15

Ala Phe Gly Phe Glu His Pro Glu Ala Phe Cys Ile Lys Lys His
            20                  25                  30
```

<210> SEQ ID NO 135
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 135

Met Lys Tyr Leu Phe Ala Phe Val Ile Ile Pro Leu Leu Tyr Ala Glu
1               5                   10                  15

Ile Ala Phe Gly Phe Glu His Pro Glu Ala Phe Cys Ile Lys Lys
            20                  25                  30

<210> SEQ ID NO 136
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 136

Lys Tyr Leu Phe Ala Phe Val Ile Ile Pro Leu Leu Tyr Ala Glu Ile
1               5                   10                  15

Ala Phe Gly Phe Glu His Pro Glu Ala Phe Cys Ile Lys Lys His
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 137

Arg Thr Pro Ser Cys Asp Ser Ile Phe Ser Tyr Tyr Thr Cys Ile Thr
1               5                   10                  15

Asp Glu Lys Leu Ile Tyr Phe Asn Asp Tyr Asp Asn Ala Ile Arg Arg
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 138

Met Lys Tyr Leu Phe Ala Phe Val Ile Ile Pro Leu Leu Tyr Ala Glu
1               5                   10                  15

Ile Ala Phe Gly Phe Glu His Pro Glu Ala Phe Cys Ile Lys Lys His
            20                  25                  30

<210> SEQ ID NO 139
<211> LENGTH: 33
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 139

Lys Tyr Leu Phe Ala Phe Val Ile Ile Pro Leu Leu Tyr Ala Glu Ile
1               5                   10                  15

Ala Phe Gly Phe Glu His Pro Glu Ala Phe Cys Ile Lys Lys His Lys
            20                  25                  30

Asp

<210> SEQ ID NO 140

```
<211> LENGTH: 32
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 140

Met Lys Tyr Leu Phe Ala Phe Val Ile Ile Pro Leu Leu Tyr Ala Glu
1               5                   10                  15

Ile Ala Phe Gly Phe Glu His Pro Glu Ala Phe Cys Ile Lys Lys His
            20                  25                  30

<210> SEQ ID NO 141
<211> LENGTH: 33
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 141

Arg Thr Pro Ser Cys Asp Ser Ile Phe Ser Tyr Tyr Thr Cys Ile Thr
1               5                   10                  15

Asp Glu Lys Leu Ile Tyr Phe Asn Asp Tyr Asp Asn Ala Ile Arg Arg
            20                  25                  30

Tyr

<210> SEQ ID NO 142
<211> LENGTH: 34
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 142

Lys His Arg Thr Pro Ser Cys Asp Ser Ile Phe Ser Tyr Tyr Thr Cys
1               5                   10                  15

Ile Thr Asp Glu Lys Leu Ile Tyr Phe Asn Asp Tyr Asp Asn Ala Ile
            20                  25                  30

Arg Arg

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 143

Lys Asn Asp Ala Ser Lys Met
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 144

Arg Ile Gly Pro Gln Arg Phe
1               5
```

```
<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 145

Lys Ala Asp Ile Arg Lys Ile
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 146

Lys Lys Cys Glu Glu Lys Phe
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 147

Lys Arg Ile Gly Pro Gln Arg Phe
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 148

Lys Val Lys Lys Gln Ala Arg Glu
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 149

Lys Tyr Asn Val Val Asp Lys Ser
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct
```

-continued

```
<400> SEQUENCE: 150

Arg Cys Ile Leu Thr Asp Lys Arg
 1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 151

Lys Ser Leu Lys Ala Asp Ile Arg Lys
 1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 152

Lys Phe Lys Asn Asp Ala Ser Lys Met
 1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 153

Lys Cys Glu Glu Lys Phe Lys Asn
 1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 154

Arg Ala Ile Gln Glu Tyr Asp Lys Thr
 1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 155

Lys Ile Met His Glu Cys Ala Lys Lys
 1               5

<210> SEQ ID NO 156
<211> LENGTH: 9
<212> TYPE: PRT
<213> ORGANISM: Artificial Sequence
```

```
<220> FEATURE:
<223> OTHER INFORMATION: Description of Artificial Sequence; NOTE =
      Synthetic Construct

<400> SEQUENCE: 156

Arg Cys Ile Leu Thr Asp Lys Arg Ile
1               5

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 157

Arg Thr Phe Ser Asn Val Leu Ile Lys Tyr
1               5                   10

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 158

Arg Thr Thr Ile Asn Tyr Tyr Arg Cys
1               5

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 159

Lys Ser Leu Lys Ala Asp Ile Arg Lys Ile
1               5                   10

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 160

Lys Lys Cys Glu Glu Lys Phe Lys Asn
1               5

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 161

Arg Ile Gly Pro Gln Arg Phe Asp Arg Ala
1               5                   10
```

```
<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 162

Lys Ile Met His Glu Cys Ala Lys Lys Val
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 163

Arg Lys Ile Met His Glu Cys Ala Lys Lys
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 164

Lys Met Ala Cys Ile Pro His Cys Lys Tyr
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 165

Lys Ile Met His Glu Cys Ala Lys Lys Val
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 166

Arg Lys Ile Met His Glu Cys Ala Lys Lys
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 167
```

```
Lys Met Ala Cys Ile Pro His Cys Lys Tyr
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 168

Lys Tyr Asn Val Val Asp Lys Ser Leu Lys Ala
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 169

Lys Arg Ile Gly Pro Gln Arg Phe Asp Arg Ala
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 170

Arg Lys Ile Met His Glu Cys Ala Lys Lys Val
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 171

Arg Glu Asp Ser His Trp Leu Asn Cys Arg Thr
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 172

Lys Ile Met His Glu Cys Ala Lys Lys Val Lys Lys
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence; NOTE =
```

-continued

Synthetic Construct

<400> SEQUENCE: 173

Arg Phe Asp Arg Ala Ile Gln Glu Tyr Asp Lys Thr
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 174

Arg Ala Ile Gln Glu Tyr Asp Lys Thr Ile Asn Ile
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 175

Lys Cys Glu Glu Lys Phe Lys Asn Asp Ala Ser Lys Met
1               5                   10

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 176

Arg Cys Ile Leu Thr Asp Lys Arg Ile Gly Pro Gln Arg Phe
1               5                   10

<210> SEQ ID NO 177
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 177

Lys Ala Asp Ile Arg Lys Ile Met His Glu Cys Ala Lys Lys
1               5                   10

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 178

Lys Tyr Asn Val Val Asp Lys Ser Leu Lys Ala Asp Ile Arg Lys
1               5                   10                  15

<210> SEQ ID NO 179
<211> LENGTH: 15

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 179

Lys Asn Asp Ala Ser Lys Met Ala Cys Ile Pro His Cys Lys Tyr
1               5                   10                  15

<210> SEQ ID NO 180
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 180

Lys Gln Ala Arg Glu Asp Ser His Trp Leu Asn Cys Arg Thr
1               5                   10

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 181

Lys Asn Asp Ala Ser Lys Met Ala Cys Ile Pro His Cys Lys Tyr
1               5                   10                  15

<210> SEQ ID NO 182
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 182

Lys Gln Ala Arg Glu Asp Ser His Trp Leu Asn Cys Arg Thr
1               5                   10

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 183

Arg Thr Phe Ser Asn Val Leu Ile Lys Tyr Asn Val Val Asp Lys Ser
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 184

Arg Thr Thr Ile Asn Tyr Tyr Arg Cys Ile Leu Thr Asp Lys Arg
1               5                   10                  15
```

```
<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 185

Lys Lys Gln Ala Arg Glu Asp Ser His Trp Leu Asn Cys Arg Thr
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 186

Arg Phe Asp Arg Ala Ile Gln Glu Tyr Asp Lys Thr Ile Asn Ile
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 187

Arg Thr Thr Ile Asn Tyr Tyr Arg Cys Ile Leu Thr Asp Lys Arg Ile
1               5                   10                  15

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 188

Lys Phe Lys Asn Asp Ala Ser Lys Met Ala Cys Ile Pro His Cys Lys
1               5                   10                  15
Tyr

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 189

Arg Ile Gly Pro Gln Arg Phe Asp Arg Ala Ile Gln Glu Tyr Asp Lys
1               5                   10                  15
Thr

<210> SEQ ID NO 190
<211> LENGTH: 17
<212> TYPE: PRT
<213> ORGANISM: Artificial Sequence
```

```
<220> FEATURE:
<223> OTHER INFORMATION: Description of Artificial Sequence; NOTE =
      Synthetic Construct

<400> SEQUENCE: 190

Lys Phe Lys Asn Asp Ala Ser Lys Met Ala Cys Ile Pro His Cys Lys
1               5                   10                  15

Tyr

<210> SEQ ID NO 191
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 191

Arg Thr Phe Ser Asn Val Leu Ile Lys Tyr Asn Val Val Asp Lys Ser
1               5                   10                  15

Leu Lys Ala

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 192

Arg Glu Asp Ser His Trp Leu Asn Cys Arg Thr Thr Ile Asn Tyr Tyr
1               5                   10                  15

Arg Cys

<210> SEQ ID NO 193
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 193

Lys Tyr Gln Tyr Tyr Gly Phe Val Ala Met Asp Asn Asn Ile Ala Lys
1               5                   10                  15

Pro Glu Ile Arg Thr
                20

<210> SEQ ID NO 194
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 194

Lys Tyr Leu Gly Leu Ala Leu Ile Ser Ala Val Phe Leu Ile Gly Thr
1               5                   10                  15

Cys Gln Ala Glu Asn Pro Ser Lys Lys
            20                  25

<210> SEQ ID NO 195
<211> LENGTH: 21
```

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 195

Lys Gln Ala Arg Glu Asp Ser His Trp Leu Asn Cys Arg Thr Thr Ile
1               5                   10                  15

Asn Tyr Tyr Arg Cys
            20

<210> SEQ ID NO 196
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 196

Lys Tyr Leu Gly Leu Ala Leu Ile Ser Ala Val Phe Leu Ile Gly Thr
1               5                   10                  15

Cys Gln Ala Glu Asn Pro Ser Lys Lys Cys
            20                  25

<210> SEQ ID NO 197
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 197

Lys Tyr Leu Gly Leu Ala Leu Ile Ser Ala Val Phe Leu Ile Gly Thr
1               5                   10                  15

Cys Gln Ala Glu Asn Pro Ser Lys Lys
            20                  25

<210> SEQ ID NO 198
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 198

Met Lys Tyr Leu Gly Leu Ala Leu Ile Ser Ala Val Phe Leu Ile Gly
1               5                   10                  15

Thr Cys Gln Ala Glu Asn Pro Ser Lys Lys
            20                  25

<210> SEQ ID NO 199
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 199

Lys Tyr Leu Gly Leu Ala Leu Ile Ser Ala Val Phe Leu Ile Gly Thr
1               5                   10                  15

Cys Gln Ala Glu Asn Pro Ser Lys Lys Cys
```

<210> SEQ ID NO 200
<211> LENGTH: 27
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 200

Met Lys Tyr Leu Gly Leu Ala Leu Ile Ser Ala Val Phe Leu Ile Gly
1               5                   10                  15

Thr Cys Gln Ala Glu Asn Pro Ser Lys Lys Cys
            20                  25

<210> SEQ ID NO 201
<211> LENGTH: 24
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 201

Arg Glu Asp Ser His Trp Leu Asn Cys Arg Thr Thr Ile Asn Tyr Tyr
1               5                   10                  15

Arg Cys Ile Leu Thr Asp Lys Arg
            20

<210> SEQ ID NO 202
<211> LENGTH: 30
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 202

Lys Tyr Leu Gly Leu Ala Leu Ile Ser Ala Val Phe Leu Ile Gly Thr
1               5                   10                  15

Cys Gln Ala Glu Asn Pro Ser Lys Lys Cys Glu Glu Lys Phe
            20                  25                  30

<210> SEQ ID NO 203
<211> LENGTH: 29
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 203

Lys Tyr Gln Tyr Tyr Gly Phe Val Ala Met Asp Asn Asn Ile Ala Lys
1               5                   10                  15

Pro Glu Ile Arg Thr Phe Ser Asn Val Leu Ile Lys Tyr
            20                  25

<210> SEQ ID NO 204
<211> LENGTH: 29
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 204

Lys Met Ala Cys Ile Pro His Cys Lys Tyr Gln Tyr Tyr Gly Phe Val
1               5                   10                  15

Ala Met Asp Asn Asn Ile Ala Lys Pro Glu Ile Arg Thr
            20                  25

<210> SEQ ID NO 205
<211> LENGTH: 34
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 205

Lys Asn Asp Ala Ser Lys Met Ala Cys Ile Pro His Cys Lys Tyr Gln
1               5                   10                  15

Tyr Tyr Gly Phe Val Ala Met Asp Asn Asn Ile Ala Lys Pro Glu Ile
            20                  25                  30

Arg Thr

<210> SEQ ID NO 206
<211> LENGTH: 35
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 206

Lys Tyr Gln Tyr Tyr Gly Phe Val Ala Met Asp Asn Asn Ile Ala Lys
1               5                   10                  15

Pro Glu Ile Arg Thr Phe Ser Asn Val Leu Ile Lys Tyr Asn Val Val
            20                  25                  30

Asp Lys Ser
        35

<210> SEQ ID NO 207
<211> LENGTH: 37
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 207

Lys Met Ala Cys Ile Pro His Cys Lys Tyr Gln Tyr Tyr Gly Phe Val
1               5                   10                  15

Ala Met Asp Asn Asn Ile Ala Lys Pro Glu Ile Arg Thr Phe Ser Asn
            20                  25                  30

Val Leu Ile Lys Tyr
        35

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 208

Lys Ala Ile Tyr Asp Lys Thr
1               5

```
<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 209

Arg Leu Leu Glu Ile Lys Gly
 1               5

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 210

Lys Gln Phe Thr Ser Arg Gly
 1               5

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 211

Lys Gly Thr Lys Ile Ser Lys Phe
 1               5

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 212

Lys Phe Cys Lys Ala Lys Asn
 1               5

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 213

Lys Ser Leu Arg Val Asn Lys Ile
 1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 214
```

```
Lys Asn Thr Lys Ser Leu Arg Val
1               5

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 215

Arg Val Asn Lys Ile Glu Lys Gln
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 216

Arg Thr Cys Gln Arg Arg Glu
1               5

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 217

Lys Ile Ser Lys Phe Cys Lys Ala
1               5

<210> SEQ ID NO 218
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 218

Lys Thr His Cys Tyr Val Lys Cys
1               5

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 219

Arg Gly Val Ala Ile Pro Ser Asp Leu Lys Ser
1               5                   10

<210> SEQ ID NO 220
<211> LENGTH: 10
<212> TYPE: PRT
<213> ORGANISM: Artificial Sequence
<220> FEATURE:
```

```
<223> OTHER INFORMATION: Description of Artificial Sequence; NOTE =
      Synthetic Construct

<400> SEQUENCE: 220

Arg Glu Ser Asp Asn Asn Ile Leu Lys Lys
1               5                   10

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 221

Lys Phe Cys Lys Ala Lys Asn Arg Glu
1               5

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 222

Arg Glu Gln Gly Glu Ser Asn Cys Lys His
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 223

Lys Ile Ser Lys Phe Cys Lys Ala Lys Asn
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 224

Lys Ile Glu Lys Gln Phe Thr Ser Arg Gly
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 225

Lys Asn Thr Lys Ser Leu Arg Val Asn Lys Ile
1               5                   10

<210> SEQ ID NO 226
```

```
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 226

Arg Glu Ser Asp Asn Asn Ile Leu Lys Lys Trp
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 227

Lys Gln Thr Ser Gly Gly Gln Gly Cys Gln Arg Ser
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 228

Lys Gly Thr Lys Ile Ser Lys Phe Cys Lys Ala
1               5                   10

<210> SEQ ID NO 229
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 229

Lys Ser Leu Arg Val Asn Lys Ile Glu Lys Gln
1               5                   10

<210> SEQ ID NO 230
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 230

Arg Arg Glu Ser Asp Asn Asn Ile Leu Lys Lys
1               5                   10

<210> SEQ ID NO 231
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 231

Lys Gln Thr Ser Gly Gly Gln Gly Cys Gln Arg Ser
```

```
1               5                   10
```

<210> SEQ ID NO 232
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 232

```
Arg Ser Asp Ala Leu Tyr Asp Cys Leu Lys Asn
1               5                   10
```

<210> SEQ ID NO 233
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 233

```
Lys His Ala Cys Ser Ala Tyr Tyr Tyr Arg Leu
1               5                   10
```

<210> SEQ ID NO 234
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 234

```
Lys Ser Met Glu Gly Glu Thr Asp Gly Ser Cys Lys Ala
1               5                   10
```

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 235

```
Arg Arg Glu Ser Asp Asn Asn Ile Leu Lys Lys Trp
1               5                   10
```

<210> SEQ ID NO 236
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 236

```
Arg Asn Ala Asp Gln Thr Leu Trp Ala Phe Arg Thr
1               5                   10
```

<210> SEQ ID NO 237
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

```
<400> SEQUENCE: 237

Lys Ser Met Glu Gly Glu Thr Asp Gly Ser Cys Lys Ala
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 238

Lys Asn Arg Glu Gln Gly Glu Ser Asn Cys Lys His
1               5                   10

<210> SEQ ID NO 239
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 239

Arg Ser Asp Ala Leu Tyr Asp Cys Leu Lys Asn Lys Lys
1               5                   10

<210> SEQ ID NO 240
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 240

Lys Trp Tyr Ala Gln Asn Pro Asp Val Lys Pro Lys Gly
1               5                   10

<210> SEQ ID NO 241
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 241

Arg Val Asn Lys Ile Glu Lys Gln Phe Thr Ser Arg Gly
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 242

Arg Thr Ala Phe Tyr Gly Thr Ile Glu Glu Ser Asn Lys Trp
1               5                   10

<210> SEQ ID NO 243
<211> LENGTH: 13
<212> TYPE: PRT
```

```
<213> ORGANISM: Artificial Sequence
<220> FEATURE:
<223> OTHER INFORMATION: Description of Artificial Sequence; NOTE =
      Synthetic Construct

<400> SEQUENCE: 243

Lys Cys Val Trp Ile His Leu Gly Leu Tyr Ser Lys Asn
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 244

Lys Gly Phe Ser Asn Glu Asp Ile Asp Glu Cys Thr Lys Gln
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 245

Lys Ala Lys Asn Arg Glu Gln Gly Glu Ser Asn Cys Lys His
1               5                   10

<210> SEQ ID NO 246
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 246

Arg Ser Asp Ala Leu Tyr Asp Cys Leu Lys Asn Lys Lys Ser
1               5                   10

<210> SEQ ID NO 247
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 247

Lys Trp Tyr Thr Trp Glu Leu Pro Asn Asp Glu Lys Thr
1               5                   10

<210> SEQ ID NO 248
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 248

Lys Gln Phe Thr Ser Arg Gly Val Ala Ile Pro Ser Asp Leu Lys Ser
1               5                   10                  15
```

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 249

Lys Thr Ile Ser Phe Phe Asn Asn Asn Val Ala Asp Leu Arg Thr
1               5                   10                  15

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 250

Arg Leu Val Asp Glu Asp Phe Glu Pro Ile His Phe Arg Leu
1               5                   10

<210> SEQ ID NO 251
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 251

Lys Gln Phe Thr Ser Arg Gly Val Ala Ile Pro Ser Asp Leu Lys Ser
1               5                   10                  15

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 252

Lys Lys Trp Tyr Thr Trp Glu Leu Pro Asn Asp Glu Lys Thr
1               5                   10

<210> SEQ ID NO 253
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 253

Lys Trp Tyr Ala Gln Asn Pro Asp Val Lys Pro Lys Gly Thr Lys Ile
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 254

```
Lys Tyr Pro Arg Asn Ala Asp Gln Thr Leu Trp Ala Phe Arg Thr
1               5                   10                  15
```

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 255

```
Arg Thr Cys Gln Arg Arg Glu Ser Asp Asn Asn Ile Leu Lys Lys
1               5                   10                  15
```

<210> SEQ ID NO 256
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 256

```
Lys Cys Val Trp Ile His Leu Gly Leu Tyr Ser Lys Asn Thr Lys Ser
1               5                   10                  15
```

<210> SEQ ID NO 257
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 257

```
Lys Ser Ala Ala Leu Glu Ala Ala Leu Gln Ile Leu Asp Asp Gln Ser
1               5                   10                  15

Ala Arg Thr
```

<210> SEQ ID NO 258
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 258

```
Arg Asn Ala Asp Gln Thr Leu Trp Ala Phe Arg Thr Cys Gln Arg Arg
1               5                   10                  15
```

<210> SEQ ID NO 259
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 259

```
Lys Ser Met Glu Gly Glu Thr Asp Gly Ser Cys Lys Ala Ile Tyr Asp
1               5                   10                  15

Lys Thr
```

<210> SEQ ID NO 260

```
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 260

Lys Ser Met Glu Gly Glu Thr Asp Gly Ser Cys Lys Ala Ile Tyr Asp
1               5                   10                  15

Lys Thr

<210> SEQ ID NO 261
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 261

Lys Ile Glu Lys Gln Phe Thr Ser Arg Gly Val Ala Ile Pro Ser Asp
1               5                   10                  15

Leu Lys Ser

<210> SEQ ID NO 262
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 262

Lys Lys Ser Ala Ala Leu Glu Ala Ala Leu Gln Ile Leu Asp Asp Gln
1               5                   10                  15

Ser Ala Arg Thr
            20

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 263

Arg Asn Ala Asp Gln Thr Leu Trp Ala Phe Arg Thr Cys Gln Arg Arg
1               5                   10                  15

Glu

<210> SEQ ID NO 264
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 264

Lys Trp Tyr Ala Gln Asn Pro Asp Val Lys Pro Lys Gly Thr Lys Ile
1               5                   10                  15

Ser Lys Phe
```

```
<210> SEQ ID NO 265
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 265

Arg Leu Leu Glu Ile Lys Gly Phe Ser Asn Glu Asp Ile Asp Glu Cys
  1               5                  10                  15

Thr Lys Gln

<210> SEQ ID NO 266
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 266

Lys Ser Ala Ala Leu Glu Ala Ala Leu Gln Ile Leu Asp Asp Gln Ser
  1               5                  10                  15

Ala Arg Thr Tyr
            20

<210> SEQ ID NO 267
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 267

Lys Cys Val Trp Ile His Leu Gly Leu Tyr Ser Lys Asn Thr Lys Ser
  1               5                  10                  15

Leu Arg Val

<210> SEQ ID NO 268
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 268

Arg Gly Val Ala Ile Pro Ser Asp Leu Lys Ser Met Glu Gly Glu Thr
  1               5                  10                  15

Asp Gly Ser Cys Lys Ala
            20

<210> SEQ ID NO 269
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 269

Lys Ala Ile Tyr Asp Lys Thr Ile Ser Phe Phe Asn Asn Asn Val Ala
  1               5                  10                  15

Asp Leu Arg Thr
```

20

<210> SEQ ID NO 270
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 270

Arg Gly Val Ala Ile Pro Ser Asp Leu Lys Ser Met Glu Gly Glu Thr
1               5                   10                  15

Asp Gly Ser Cys Lys Ala
            20

<210> SEQ ID NO 271
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 271

Arg Leu Val Asp Glu Asp Phe Glu Pro Ile His Phe Arg Leu Leu Glu
1               5                   10                  15

Ile Lys Gly

<210> SEQ ID NO 272
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 272

Lys Asn Lys Lys Ser Ala Ala Leu Glu Ala Ala Leu Gln Ile Leu Asp
1               5                   10                  15

Asp Gln Ser Ala Arg Thr
            20

<210> SEQ ID NO 273
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 273

Arg Glu Gln Gly Glu Ser Asn Cys Lys His Ala Cys Ser Ala Tyr Tyr
1               5                   10                  15

Tyr Arg Leu

<210> SEQ ID NO 274
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 274

Lys Gln Thr Ser Gly Gly Gln Gly Cys Gln Arg Ser Asp Ala Leu Tyr

```
                1               5              10              15
Asp Cys Leu Lys Asn
            20

<210> SEQ ID NO 275
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 275

Lys Lys Ser Ala Ala Leu Glu Ala Ala Leu Gln Ile Leu Asp Asp Gln
1               5                  10                  15

Ser Ala Arg Thr Tyr
            20

<210> SEQ ID NO 276
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 276

Lys Gln Thr Ser Gly Gly Gln Gly Cys Gln Arg Ser Asp Ala Leu Tyr
1               5                  10                  15

Asp Cys Leu Lys Asn
            20

<210> SEQ ID NO 277
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 277

Lys Thr His Cys Tyr Val Lys Cys Val Trp Ile His Leu Gly Leu Tyr
1               5                  10                  15

Ser Lys Asn

<210> SEQ ID NO 278
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 278

Lys Tyr Pro Arg Asn Ala Asp Gln Thr Leu Trp Ala Phe Arg Thr Cys
1               5                  10                  15

Gln Arg Arg

<210> SEQ ID NO 279
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct
```

```
<400> SEQUENCE: 279

Asn Ala Val Ile Thr Ser Leu Val Phe Leu Ser Leu Val Gly Leu Gly
1               5                   10                  15

Tyr Ser Trp Lys Tyr
            20

<210> SEQ ID NO 280
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 280

Lys Trp Tyr Thr Trp Glu Leu Pro Asn Asp Glu Lys Thr His Cys Tyr
1               5                   10                  15

Val Lys Cys

<210> SEQ ID NO 281
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 281

Met Asn Ala Val Ile Thr Ser Leu Val Phe Leu Ser Leu Val Gly Leu
1               5                   10                  15

Gly Tyr Ser Trp Lys Tyr
            20

<210> SEQ ID NO 282
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 282

Lys Gln Thr Ser Gly Gly Gln Gly Cys Gln Arg Ser Asp Ala Leu Tyr
1               5                   10                  15

Asp Cys Leu Lys Asn Lys Lys
            20

<210> SEQ ID NO 283
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 283

Lys Lys Trp Tyr Thr Trp Glu Leu Pro Asn Asp Glu Lys Thr His Cys
1               5                   10                  15

Tyr Val Lys Cys
            20

<210> SEQ ID NO 284
<211> LENGTH: 21
<212> TYPE: PRT
<213> ORGANISM: Artificial Sequence
```

```
<220> FEATURE:
<223> OTHER INFORMATION: Description of Artificial Sequence; NOTE =
      Synthetic Construct

<400> SEQUENCE: 284

Lys Asn Arg Glu Gln Gly Glu Ser Asn Cys Lys His Ala Cys Ser Ala
 1               5                  10                  15

Tyr Tyr Tyr Arg Leu
             20

<210> SEQ ID NO 285
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 285

Lys Gly Phe Ser Asn Glu Asp Ile Asp Glu Cys Thr Lys Gln Thr Ser
 1               5                  10                  15

Gly Gly Gln Gly Cys Gln Arg Ser
             20

<210> SEQ ID NO 286
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 286

Arg Glu Ser Asp Asn Asn Ile Leu Lys Lys Trp Tyr Thr Trp Glu Leu
 1               5                  10                  15

Pro Asn Asp Glu Lys Thr
             20

<210> SEQ ID NO 287
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 287

Lys Thr His Cys Tyr Val Lys Cys Val Trp Ile His Leu Gly Leu Tyr
 1               5                  10                  15

Ser Lys Asn Thr Lys Ser
             20

<210> SEQ ID NO 288
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 288

Asn Ala Val Ile Thr Ser Leu Val Phe Leu Ser Leu Val Gly Leu Gly
 1               5                  10                  15

Tyr Ser Trp Lys Tyr Pro Arg Asn
             20
```

<210> SEQ ID NO 289
<211> LENGTH: 27
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 289

Arg Gly Val Ala Ile Pro Ser Asp Leu Lys Ser Met Glu Gly Glu Thr
 1               5                  10                  15
Asp Gly Ser Cys Lys Ala Ile Tyr Asp Lys Thr
            20                  25

<210> SEQ ID NO 290
<211> LENGTH: 25
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 290

Arg Thr Ala Phe Tyr Gly Thr Ile Glu Glu Ser Asn Lys Trp Tyr Ala
 1               5                  10                  15
Gln Asn Pro Asp Val Lys Pro Lys Gly
            20                  25

<210> SEQ ID NO 291
<211> LENGTH: 27
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 291

Lys Gln Phe Thr Ser Arg Gly Val Ala Ile Pro Ser Asp Leu Lys Ser
 1               5                  10                  15
Met Glu Gly Glu Thr Asp Gly Ser Cys Lys Ala
            20                  25

<210> SEQ ID NO 292
<211> LENGTH: 27
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 292

Arg Gly Val Ala Ile Pro Ser Asp Leu Lys Ser Met Glu Gly Glu Thr
 1               5                  10                  15
Asp Gly Ser Cys Lys Ala Ile Tyr Asp Lys Thr
            20                  25

<210> SEQ ID NO 293
<211> LENGTH: 23
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 293

Lys His Ala Cys Ser Ala Tyr Tyr Tyr Arg Leu Val Asp Glu Asp Phe

Glu Pro Ile His Phe Arg Leu
            20

<210> SEQ ID NO 294
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 294

Lys Gln Phe Thr Ser Arg Gly Val Ala Ile Pro Ser Asp Leu Lys Ser
1               5                   10                  15

Met Glu Gly Glu Thr Asp Gly Ser Cys Lys Ala
            20                  25

<210> SEQ ID NO 295
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 295

Met Asn Ala Val Ile Thr Ser Leu Val Phe Leu Ser Leu Val Gly Leu
1               5                   10                  15

Gly Tyr Ser Trp Lys Tyr Pro Arg Asn
            20                  25

<210> SEQ ID NO 296
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 296

Lys Gln Phe Thr Ser Arg Gly Val Ala Ile Pro Ser Asp Leu Lys Ser
1               5                   10                  15

Met Glu Gly Glu Thr Asp Gly Ser Cys Lys Ala
            20                  25

<210> SEQ ID NO 297
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 297

Met Asn Ala Val Ile Thr Ser Leu Val Phe Leu Ser Leu Val Gly Leu
1               5                   10                  15

Gly Tyr Ser Trp Lys Tyr Pro Arg Asn
            20                  25

<210> SEQ ID NO 298
<211> LENGTH: 27
<212> TYPE: PRT
<213> ORGANISM: Artificial Sequence
<220> FEATURE:
<223> OTHER INFORMATION: Description of Artificial Sequence; NOTE =

Synthetic Construct

<400> SEQUENCE: 298

Lys Thr Ile Ser Phe Phe Asn Asn Asn Val Ala Asp Leu Arg Thr Ala
1               5                   10                  15

Phe Tyr Gly Thr Ile Glu Glu Ser Asn Lys Trp
            20                  25

<210> SEQ ID NO 299
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 299

Arg Thr Ala Phe Tyr Gly Thr Ile Glu Glu Ser Asn Lys Trp Tyr Ala
1               5                   10                  15

Gln Asn Pro Asp Val Lys Pro Lys Gly Thr Lys Ile
            20                  25

<210> SEQ ID NO 300
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 300

Arg Leu Leu Glu Ile Lys Gly Phe Ser Asn Glu Asp Ile Asp Glu Cys
1               5                   10                  15

Thr Lys Gln Thr Ser Gly Gly Gln Gly Cys Gln Arg Ser
            20                  25

<210> SEQ ID NO 301
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 301

Lys Ser Met Glu Gly Glu Thr Asp Gly Ser Cys Lys Ala Ile Tyr Asp
1               5                   10                  15

Lys Thr Ile Ser Phe Phe Asn Asn Asn Val Ala Asp Leu Arg Thr
            20                  25                  30

<210> SEQ ID NO 302
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 302

Lys His Ala Cys Ser Ala Tyr Tyr Tyr Arg Leu Val Asp Glu Asp Phe
1               5                   10                  15

Glu Pro Ile His Phe Arg Leu Leu Glu Ile Lys Gly
            20                  25

<210> SEQ ID NO 303

<211> LENGTH: 32
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 303

Lys Ala Ile Tyr Asp Lys Thr Ile Ser Phe Phe Asn Asn Val Ala
1               5                   10                  15

Asp Leu Arg Thr Ala Phe Tyr Gly Thr Ile Glu Glu Ser Asn Lys Trp
            20                  25                  30

<210> SEQ ID NO 304
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 304

Arg Leu Val Asp Glu Asp Phe Glu Pro Ile His Phe Arg Leu Leu Glu
1               5                   10                  15

Ile Lys Gly Phe Ser Asn Glu Asp Ile Asp Glu Cys Thr Lys Gln
            20                  25                  30

<210> SEQ ID NO 305
<211> LENGTH: 33
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 305

Lys Gly Phe Ser Asn Glu Asp Ile Asp Glu Cys Thr Lys Gln Thr Ser
1               5                   10                  15

Gly Gly Gln Gly Cys Gln Arg Ser Asp Ala Leu Tyr Asp Cys Leu Lys
            20                  25                  30

Asn

<210> SEQ ID NO 306
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 306

Arg Glu Gln Gly Glu Ser Asn Cys Lys His Ala Cys Ser Ala Tyr Tyr
1               5                   10                  15

Tyr Arg Leu Val Asp Glu Asp Phe Glu Pro Ile His Phe Arg Leu
            20                  25                  30

<210> SEQ ID NO 307
<211> LENGTH: 30
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 307

Lys Trp Tyr Thr Trp Glu Leu Pro Asn Asp Glu Lys Thr His Cys Tyr

```
                1               5                  10                 15
Val Lys Cys Val Trp Ile His Leu Gly Leu Tyr Ser Lys Asn
            20                  25                 30

<210> SEQ ID NO 308
<211> LENGTH: 34
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 308

Asn Ala Val Ile Thr Ser Leu Val Phe Leu Ser Leu Val Gly Leu Gly
1               5                   10                  15

Tyr Ser Trp Lys Tyr Pro Arg Asn Ala Asp Gln Thr Leu Trp Ala Phe
            20                  25                  30

Arg Thr

<210> SEQ ID NO 309
<211> LENGTH: 35
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 309

Met Asn Ala Val Ile Thr Ser Leu Val Phe Leu Ser Leu Val Gly Leu
1               5                   10                  15

Gly Tyr Ser Trp Lys Tyr Pro Arg Asn Ala Asp Gln Thr Leu Trp Ala
            20                  25                  30

Phe Arg Thr
        35

<210> SEQ ID NO 310
<211> LENGTH: 37
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 310

Thr Ile Ser Phe Phe Asn Asn Asn Val Ala Asp Leu Arg Thr Ala Phe
1               5                   10                  15

Tyr Gly Thr Ile Glu Glu Ser Asn Lys Trp Tyr Ala Gln Asn Pro Asp
            20                  25                  30

Val Lys Pro Lys Gly
        35

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 311

Lys Ser Leu Ser Gly Arg Thr
1               5

<210> SEQ ID NO 312
```

```
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 312

Arg Glu Glu Ser Asp Lys Trp
1               5

<210> SEQ ID NO 313
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 313

Lys Ala Leu Tyr Glu Lys Thr
1               5

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 314

Lys Ala Arg Glu Lys Lys Gly
1               5

<210> SEQ ID NO 315
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 315

Lys Gln Phe Lys Ser Arg Gly
1               5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 316

Arg Gly Leu Glu Ile Pro Lys Asp
1               5

<210> SEQ ID NO 317
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 317

Lys Gln Phe Lys Ser Arg Gly
```

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 318

Arg Thr Asp Gly Ser Cys Lys Ala
1               5

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 319

Lys Glu Lys Gly Glu Thr Lys Asn
1               5

<210> SEQ ID NO 320
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 320

Arg Asp Lys Ala Arg Glu Lys Lys
1               5

<210> SEQ ID NO 321
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 321

Lys Thr Ile Pro Phe Phe Lys Asn
1               5

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 322

Arg Glu Lys Lys Gly Cys Lys Val
1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

```
<400> SEQUENCE: 323

Lys Val Gly Asp Ala Leu Tyr Arg Cys
 1               5

<210> SEQ ID NO 324
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 324

Lys Lys Gln Phe Lys Ser Arg Gly
 1               5

<210> SEQ ID NO 325
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 325

Lys Gln Ile Asn Asp Cys Arg Asp
 1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 326

Arg Ile Ala Phe Tyr Gly Thr Arg Glu
 1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 327

Lys His Pro Glu Val Lys Pro Lys Arg
 1               5

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 328

Lys Ala Ile Asn Ile Asp Ala Val Lys Lys
 1               5                   10

<210> SEQ ID NO 329
<211> LENGTH: 10
<212> TYPE: PRT
```

```
<213> ORGANISM: Artificial Sequence
<220> FEATURE:
<223> OTHER INFORMATION: Description of Artificial Sequence; NOTE =
      Synthetic Construct

<400> SEQUENCE: 329

Lys Asp Ile Lys Ser Leu Ser Gly Arg Thr
1               5                   10

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 330

Lys Gly Glu Thr Lys Asn Cys Arg Arg
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 331

Arg Leu Asp Ile Glu Ser Trp Lys Tyr
1               5

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 332

Lys Ser Arg Gly Leu Glu Ile Pro Lys Asp
1               5                   10

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 333

Lys Asn Asn Phe Gln Asn Leu Arg Ile
1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 334

Arg Cys Leu Arg Leu Ile Asn Lys Gln
1               5
```

```
<210> SEQ ID NO 335
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 335

Lys Leu Asp Ile Ala Gly Ile Thr Asp Lys Gln
1               5                   10

<210> SEQ ID NO 336
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 336

Lys Ala Ile Asn Ile Asp Ala Val Lys Lys Gln
1               5                   10

<210> SEQ ID NO 337
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 337

Lys His Pro Glu Val Lys Pro Lys Arg Thr
1               5                   10

<210> SEQ ID NO 338
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 338

Lys Gln Gly Leu Ile Ala Thr Met Glu Arg Leu
1               5                   10

<210> SEQ ID NO 339
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 339

Arg Gln Thr Thr Asp Ile Glu Ser Val Lys Leu
1               5                   10

<210> SEQ ID NO 340
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 340
```

-continued

Arg Gly Leu Glu Ile Pro Lys Asp Ile Lys Ser
1               5                   10

<210> SEQ ID NO 341
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 341

Lys Gln Gly Leu Ile Ala Thr Met Glu Arg Leu
1               5                   10

<210> SEQ ID NO 342
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 342

Arg Gln Thr Thr Asp Ile Glu Ser Val Lys Leu
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 343

Lys Gly Glu Thr Lys Asn Cys Arg Arg Ala
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 344

Lys Gln Gly Leu Ile Ala Thr Met Glu Arg Leu
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 345

Lys Gln Ile Asn Asp Cys Arg Asp Lys Ala
1               5                   10

<210> SEQ ID NO 346
<211> LENGTH: 9
<212> TYPE: PRT
<213> ORGANISM: Artificial Sequence
<220> FEATURE:

```
<223> OTHER INFORMATION: Description of Artificial Sequence; NOTE =
      Synthetic Construct

<400> SEQUENCE: 346

Arg Leu Asp Ile Glu Ser Trp Lys Tyr
1               5

<210> SEQ ID NO 347
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 347

Lys Gln Ile Asn Asp Cys Arg Asp Lys Ala
1               5                   10

<210> SEQ ID NO 348
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 348

Arg Lys Leu Asp Ile Ala Gly Ile Thr Asp Lys Gln
1               5                   10

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 349

Arg Val Ser Glu Phe Cys Thr Ala Glu Lys Glu
1               5                   10

<210> SEQ ID NO 350
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 350

Arg Ala Cys Ser Leu Tyr Tyr Tyr Arg Phe
1               5                   10

<210> SEQ ID NO 351
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 351

Lys Glu Lys Gly Glu Thr Lys Asn Cys Arg Arg
1               5                   10

<210> SEQ ID NO 352
```

```
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 352

Arg Glu Glu Ser Asp Lys Trp Phe Ala Lys His
1               5                   10

<210> SEQ ID NO 353
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 353

Lys Gly Cys Lys Val Gly Asp Ala Leu Tyr Arg Cys
1               5                   10

<210> SEQ ID NO 354
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 354

Lys Ser Leu Ser Gly Arg Thr Asp Gly Ser Cys Lys Ala
1               5                   10

<210> SEQ ID NO 355
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 355

Lys Val Gly Asp Ala Leu Tyr Arg Cys Leu Arg Leu
1               5                   10

<210> SEQ ID NO 356
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 356

Lys His Pro Glu Val Lys Pro Lys Arg Thr Arg Val
1               5                   10

<210> SEQ ID NO 357
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 357

Lys Ser Arg Gly Leu Glu Ile Pro Lys Asp Ile Lys Ser
```

```
                1               5                   10
```

<210> SEQ ID NO 358
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 358

```
Arg Arg Ala Cys Ser Leu Tyr Tyr Tyr Arg Phe
1               5                   10
```

<210> SEQ ID NO 359
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 359

```
Lys Gln Ile Asn Asp Cys Arg Asp Lys Ala Arg Glu
1               5                   10
```

<210> SEQ ID NO 360
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 360

```
Lys Lys Gly Cys Lys Val Gly Asp Ala Leu Tyr Arg Cys
1               5                   10
```

<210> SEQ ID NO 361
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 361

```
Arg Thr Asp Gly Ser Cys Lys Ala Leu Tyr Glu Lys Thr
1               5                   10
```

<210> SEQ ID NO 362
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 362

```
Lys Gln Phe Lys Ser Arg Gly Leu Glu Ile Pro Lys Asp
1               5                   10
```

<210> SEQ ID NO 363
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct -continued

<400> SEQUENCE: 363

Lys Gln Ile Asn Asp Cys Arg Asp Lys Ala Arg Glu
1               5                   10

<210> SEQ ID NO 364
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 364

Lys Gln Phe Lys Ser Arg Gly Leu Glu Ile Pro Lys Asp
1               5                   10

<210> SEQ ID NO 365
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 365

Arg Val Ser Glu Phe Cys Thr Ala Glu Lys Glu Lys Gly
1               5                   10

<210> SEQ ID NO 366
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 366

Arg Thr Arg Val Ser Glu Phe Cys Thr Ala Glu Lys Glu
1               5                   10

<210> SEQ ID NO 367
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 367

Lys Ala Leu Tyr Glu Lys Thr Ile Pro Phe Phe Lys Asn
1               5                   10

<210> SEQ ID NO 368
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 368

Lys Trp Phe Ala Lys His Pro Glu Val Lys Pro Lys Arg
1               5                   10

<210> SEQ ID NO 369
<211> LENGTH: 14
<212> TYPE: PRT

```
<213> ORGANISM: Artificial Sequence
<220> FEATURE:
<223> OTHER INFORMATION: Description of Artificial Sequence; NOTE =
      Synthetic Construct

<400> SEQUENCE: 369

Lys Ala Ile Asn Ile Asp Ala Val Lys Lys Gln Phe Lys Ser
1               5                   10

<210> SEQ ID NO 370
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 370

Arg Ile Ala Phe Tyr Gly Thr Arg Glu Glu Ser Asp Lys Trp
1               5                   10

<210> SEQ ID NO 371
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 371

Arg Leu Ile Asn Lys Gln Gly Leu Ile Ala Thr Met Glu Arg Leu
1               5                   10                  15

<210> SEQ ID NO 372
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 372

Lys Arg Thr Arg Val Ser Glu Phe Cys Thr Ala Glu Lys Glu
1               5                   10

<210> SEQ ID NO 373
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 373

Arg Leu Ile Asn Lys Gln Gly Leu Ile Ala Thr Met Glu Arg Leu
1               5                   10                  15

<210> SEQ ID NO 374
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 374

Arg Gly Leu Glu Ile Pro Lys Asp Ile Lys Ser Leu Ser Gly Arg Thr
1               5                   10                  15
```

<210> SEQ ID NO 375
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 375

Lys Trp Phe Ala Lys His Pro Glu Val Lys Pro Lys Arg Thr
1               5                   10

<210> SEQ ID NO 376
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 376

Lys Asp Ile Lys Ser Leu Ser Gly Arg Thr Asp Gly Ser Cys Lys Ala
1               5                   10                  15

<210> SEQ ID NO 377
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 377

Arg Phe Val Asp Glu Asp Tyr Gln Pro Ile Tyr Phe Arg Lys
1               5                   10

<210> SEQ ID NO 378
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 378

Lys Gly Cys Lys Val Gly Asp Ala Leu Tyr Arg Cys Leu Arg Leu
1               5                   10                  15

<210> SEQ ID NO 379
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 379

Arg Thr Arg Val Ser Glu Phe Cys Thr Ala Glu Lys Glu Lys Gly
1               5                   10                  15

<210> SEQ ID NO 380
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 380

```
Lys Thr Ile Pro Phe Phe Lys Asn Asn Phe Gln Asn Leu Arg Ile
 1               5                   10                  15

<210> SEQ ID NO 381
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 381

Lys Val Gly Asp Ala Leu Tyr Arg Cys Leu Arg Leu Ile Asn Lys Gln
 1               5                   10                  15

<210> SEQ ID NO 382
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 382

Lys Asn Cys Arg Arg Ala Cys Ser Leu Tyr Tyr Tyr Arg Phe
 1               5                   10

<210> SEQ ID NO 383
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 383

Lys Asn Asn Phe Gln Asn Leu Arg Ile Ala Phe Tyr Gly Thr Arg Glu
 1               5                   10                  15

<210> SEQ ID NO 384
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 384

Arg Phe Val Asp Glu Asp Tyr Gln Pro Ile Tyr Phe Arg Lys Leu
 1               5                   10                  15

<210> SEQ ID NO 385
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 385

Lys Leu Asp Ile Ala Gly Ile Thr Asp Lys Gln Ile Asn Asp Cys Arg
 1               5                   10                  15
Asp

<210> SEQ ID NO 386
<211> LENGTH: 17
<212> TYPE: PRT
```

```
<213> ORGANISM: Artificial Sequence
<220> FEATURE:
<223> OTHER INFORMATION: Description of Artificial Sequence; NOTE =
      Synthetic Construct

<400> SEQUENCE: 386

Arg Val Ser Glu Phe Cys Thr Ala Glu Lys Glu Lys Gly Glu Thr Lys
  1               5                  10                  15

Asn

<210> SEQ ID NO 387
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 387

Arg Asn Gly Asp Gln Thr Tyr Trp Ala Phe Asn Thr Cys Gln Arg Gln
  1               5                  10                  15

<210> SEQ ID NO 388
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 388

Lys Ser Leu Ser Gly Arg Thr Asp Gly Ser Cys Lys Ala Leu Tyr Glu
  1               5                  10                  15

Lys Thr

<210> SEQ ID NO 389
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 389

Lys Cys Val Phe Ile His Leu Gly Phe Tyr Asn Glu Gln Glu Lys Ala
  1               5                  10                  15

<210> SEQ ID NO 390
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 390

Lys Gln Gly Leu Ile Ala Thr Met Glu Arg Leu Asp Ile Glu Ser Trp
  1               5                  10                  15

Lys Tyr

<210> SEQ ID NO 391
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct
```

<400> SEQUENCE: 391

Arg Lys Leu Asp Ile Ala Gly Ile Thr Asp Lys Gln Ile Asn Asp Cys
1               5                   10                  15

Arg Asp

<210> SEQ ID NO 392
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 392

Lys Gln Gly Leu Ile Ala Thr Met Glu Arg Leu Asp Ile Glu Ser Trp
1               5                   10                  15

Lys Tyr

<210> SEQ ID NO 393
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 393

Arg Cys Leu Arg Leu Ile Asn Lys Gln Gly Leu Ile Ala Thr Met Glu
1               5                   10                  15

Arg Leu

<210> SEQ ID NO 394
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 394

Arg Ile Ala Phe Tyr Gly Thr Arg Glu Glu Ser Asp Lys Trp Phe Ala
1               5                   10                  15

Lys His

<210> SEQ ID NO 395
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 395

Arg Glu Glu Ser Asp Lys Trp Phe Ala Lys His Pro Glu Val Lys Pro
1               5                   10                  15

Lys Arg

<210> SEQ ID NO 396
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 396

Lys Leu Asp Ile Ala Gly Ile Thr Asp Lys Gln Ile Asn Asp Cys Arg
1               5                   10                  15

Asp Lys Ala

<210> SEQ ID NO 397
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 397

Arg Thr Asp Gly Ser Cys Lys Ala Leu Tyr Glu Lys Thr Ile Pro Phe
1               5                   10                  15

Phe Lys Asn

<210> SEQ ID NO 398
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 398

Lys Gln Gly Leu Ile Ala Thr Met Glu Arg Leu Asp Ile Glu Ser Trp
1               5                   10                  15

Lys Tyr

<210> SEQ ID NO 399
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 399

Arg Val Val Gln Cys Leu Val Phe Phe Ser Ile Leu Gly Leu Gly Tyr
1               5                   10                  15

Ser Trp Arg Phe
            20

<210> SEQ ID NO 400
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 400

Arg Phe Pro Arg Asn Gly Asp Gln Thr Tyr Trp Ala Phe Asn Thr Cys
1               5                   10                  15

Gln Arg Gln

<210> SEQ ID NO 401
<211> LENGTH: 20
<212> TYPE: PRT
<213> ORGANISM: Artificial Sequence
<220> FEATURE:
<223> OTHER INFORMATION: Description of Artificial Sequence; NOTE =

-continued

```
      Synthetic Construct

<400> SEQUENCE: 401

Lys Ala Leu Tyr Glu Lys Thr Ile Pro Phe Phe Lys Asn Asn Phe Gln
1               5                   10                  15

Asn Leu Arg Ile
            20

<210> SEQ ID NO 402
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 402

Lys Leu Trp Asp Gln Trp Leu Leu Pro Asn Asn Ala Ala Thr His Cys
1               5                   10                  15

Tyr Ile Lys Cys
            20

<210> SEQ ID NO 403
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 403

Lys Asn Asn Phe Gln Asn Leu Arg Ile Ala Phe Tyr Gly Thr Arg Glu
1               5                   10                  15

Glu Ser Asp Lys Trp
            20

<210> SEQ ID NO 404
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 404

Lys Arg Val Val Gln Cys Leu Val Phe Phe Ser Ile Leu Gly Leu Gly
1               5                   10                  15

Tyr Ser Trp Arg Phe
            20

<210> SEQ ID NO 405
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 405

Arg Leu Ile Asn Lys Gln Gly Leu Ile Ala Thr Met Glu Arg Leu Asp
1               5                   10                  15

Ile Glu Ser Trp Lys Tyr
            20

<210> SEQ ID NO 406
```

```
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 406

Lys Thr Ile Pro Phe Phe Lys Asn Asn Phe Gln Asn Leu Arg Ile Ala
1               5                   10                  15

Phe Tyr Gly Thr Arg Glu
            20

<210> SEQ ID NO 407
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 407

Lys Arg Val Val Gln Cys Leu Val Phe Phe Ser Ile Leu Gly Leu Gly
1               5                   10                  15

Tyr Ser Trp Arg Phe
            20

<210> SEQ ID NO 408
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 408

Arg Val Val Gln Cys Leu Val Phe Phe Ser Ile Leu Gly Leu Gly Tyr
1               5                   10                  15

Ser Trp Arg Phe Pro Arg Asn
            20

<210> SEQ ID NO 409
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 409

Met Lys Arg Val Val Gln Cys Leu Val Phe Phe Ser Ile Leu Gly Leu
1               5                   10                  15

Gly Tyr Ser Trp Arg Phe
            20

<210> SEQ ID NO 410
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 410

Lys Cys Val Phe Ile His Leu Gly Phe Tyr Asn Glu Gln Glu Lys Ala
1               5                   10                  15
```

```
Ile Asn Ile Asp Ala Val Lys Lys
            20
```

```
<210> SEQ ID NO 411
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 411

Arg Phe Val Asp Glu Asp Tyr Gln Pro Ile Tyr Phe Arg Lys Leu Asp
 1               5                  10                  15

Ile Ala Gly Ile Thr Asp Lys Gln
            20
```

```
<210> SEQ ID NO 412
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 412

Arg Ala Cys Ser Leu Tyr Tyr Tyr Arg Phe Val Asp Glu Asp Tyr Gln
 1               5                  10                  15

Pro Ile Tyr Phe Arg Lys
            20
```

```
<210> SEQ ID NO 413
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 413

Lys Arg Val Val Gln Cys Leu Val Phe Phe Ser Ile Leu Gly Leu Gly
 1               5                  10                  15

Tyr Ser Trp Arg Phe Pro Arg Asn
            20
```

```
<210> SEQ ID NO 414
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 414

Lys Cys Val Phe Ile His Leu Gly Phe Tyr Asn Glu Gln Glu Lys Ala
 1               5                  10                  15

Ile Asn Ile Asp Ala Val Lys Lys Gln
            20                  25
```

```
<210> SEQ ID NO 415
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct
```

```
<400> SEQUENCE: 415

Arg Asn Gly Asp Gln Thr Tyr Trp Ala Phe Asn Thr Cys Gln Arg Gln
1               5                   10                  15

Thr Thr Asp Ile Glu Ser Val Lys Leu
            20                  25

<210> SEQ ID NO 416
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 416

Arg Ala Cys Ser Leu Tyr Tyr Tyr Arg Phe Val Asp Glu Asp Tyr Gln
1               5                   10                  15

Pro Ile Tyr Phe Arg Lys Leu
            20

<210> SEQ ID NO 417
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 417

Arg Arg Ala Cys Ser Leu Tyr Tyr Tyr Arg Phe Val Asp Glu Asp Tyr
1               5                   10                  15

Gln Pro Ile Tyr Phe Arg Lys
            20

<210> SEQ ID NO 418
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 418

Arg Phe Pro Arg Asn Gly Asp Gln Thr Tyr Trp Ala Phe Asn Thr Cys
1               5                   10                  15

Gln Arg Gln Thr Thr Asp Ile Glu Ser Val Lys Leu
            20                  25

<210> SEQ ID NO 419
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 419

Arg Gln Thr Thr Asp Ile Glu Ser Val Lys Leu Trp Asp Gln Trp Leu
1               5                   10                  15

Leu Pro Asn Asn Ala Ala Thr His Cys Tyr Ile Lys Cys
            20                  25

<210> SEQ ID NO 420
<211> LENGTH: 34
<212> TYPE: PRT
```

```
<213> ORGANISM: Artificial Sequence
<220> FEATURE:
<223> OTHER INFORMATION: Description of Artificial Sequence; NOTE =
      Synthetic Construct

<400> SEQUENCE: 420

Lys Leu Trp Asp Gln Trp Leu Leu Pro Asn Asn Ala Ala Thr His Cys
 1               5                  10                  15

Tyr Ile Lys Cys Val Phe Ile His Leu Gly Phe Tyr Asn Glu Gln Glu
            20                  25                  30

Lys Ala

<210> SEQ ID NO 421
<211> LENGTH: 37
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 421

Arg Val Val Gln Cys Leu Val Phe Phe Ser Ile Leu Gly Leu Gly Tyr
 1               5                  10                  15

Ser Trp Arg Phe Pro Arg Asn Gly Asp Gln Thr Tyr Trp Ala Phe Asn
            20                  25                  30

Thr Cys Gln Arg Gln
        35

<210> SEQ ID NO 422
<211> LENGTH: 42
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 422

Lys Leu Trp Asp Gln Trp Leu Leu Pro Asn Asn Ala Ala Thr His Cys
 1               5                  10                  15

Tyr Ile Lys Cys Val Phe Ile His Leu Gly Phe Tyr Asn Glu Gln Glu
            20                  25                  30

Lys Ala Ile Asn Ile Asp Ala Val Lys Lys
        35                  40

<210> SEQ ID NO 423
<211> LENGTH: 43
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 423

Arg Asn Gly Asp Gln Thr Tyr Trp Ala Phe Asn Thr Cys Gln Arg Gln
 1               5                  10                  15

Thr Thr Asp Ile Glu Ser Val Lys Leu Trp Asp Gln Trp Leu Leu Pro
            20                  25                  30

Asn Asn Ala Ala Thr His Cys Tyr Ile Lys Cys
        35                  40

<210> SEQ ID NO 424
<211> LENGTH: 43
<212> TYPE: PRT
<213> ORGANISM: Artificial Sequence
```

```
<220> FEATURE:
<223> OTHER INFORMATION: Description of Artificial Sequence; NOTE =
      Synthetic Construct

<400> SEQUENCE: 424

Arg Gln Thr Thr Asp Ile Glu Ser Val Lys Leu Trp Asp Gln Trp Leu
1               5                   10                  15

Leu Pro Asn Asn Ala Ala Thr His Cys Tyr Ile Lys Cys Val Phe Ile
            20                  25                  30

His Leu Gly Phe Tyr Asn Glu Gln Glu Lys Ala
            35                  40

<210> SEQ ID NO 425
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 425

Lys Asn Ser Pro Ala Lys Tyr
1               5

<210> SEQ ID NO 426
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 426

Arg Lys Gly Gly Asp Arg Gly
1               5

<210> SEQ ID NO 427
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 427

Lys Ser Thr Pro Ser Gly Lys Glu
1               5

<210> SEQ ID NO 428
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 428

Arg Asp Asn Gly Arg Lys Gly
1               5

<210> SEQ ID NO 429
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct
```

```
<400> SEQUENCE: 429

Arg Ile Lys Thr Phe Lys Ala
1               5

<210> SEQ ID NO 430
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 430

Arg Asn Thr Ile Val Gly Arg Ile
1               5

<210> SEQ ID NO 431
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 431

Lys Gln Pro Asp Leu Ser Lys Tyr
1               5

<210> SEQ ID NO 432
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 432

Arg Arg Gln Asn Lys Lys Gln
1               5

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 433

Lys Gly Gly Asp Arg Gly Ser Lys Ser
1               5

<210> SEQ ID NO 434
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 434

Arg Gln Gln Asp Arg Arg Gln
1               5

<210> SEQ ID NO 435
<211> LENGTH: 8
<212> TYPE: PRT
<213> ORGANISM: Artificial Sequence
```

```
<220> FEATURE:
<223> OTHER INFORMATION: Description of Artificial Sequence; NOTE =
      Synthetic Construct

<400> SEQUENCE: 435

Lys Gln Pro Asp Leu Ser Lys Tyr
1               5

<210> SEQ ID NO 436
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 436

Arg Ile Lys Thr Phe Lys Ala
1               5

<210> SEQ ID NO 437
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 437

Lys Thr Pro Asp Glu Glu Arg Ile
1               5

<210> SEQ ID NO 438
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 438

Arg Lys Gly Gly Asp Arg Gly Ser Lys Ser
1               5                   10

<210> SEQ ID NO 439
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 439

Arg Ile Phe Arg Thr Asn Arg Ala
1               5

<210> SEQ ID NO 440
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 440

Lys Tyr Lys Asn Ser Pro Ala Lys Tyr
1               5
```

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 441

Lys Lys Gln Pro Asp Leu Ser Lys Tyr
 1               5

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 442

Arg Arg Pro Ser Gln Ser Pro Arg Gly
 1               5

<210> SEQ ID NO 443
<211> LENGTH: 11
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 443

Arg Gly Ser Lys Ser Thr Pro Ser Gly Lys Glu
 1               5                   10

<210> SEQ ID NO 444
<211> LENGTH: 10
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 444

Arg Asn Thr Ile Val Gly Arg Ile Lys Thr
 1               5                   10

<210> SEQ ID NO 445
<211> LENGTH: 10
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 445

Lys Leu Ile Leu Asp Asn Pro Asn Arg Asn
 1               5                   10

<210> SEQ ID NO 446
<211> LENGTH: 10
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 446

Lys Gln Pro Asp Leu Ser Lys Tyr Lys Asn
1               5                   10

<210> SEQ ID NO 447
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 447

Arg Asp Asn Gly Arg Lys Gly Gly Asp Arg Gly
1               5                   10

<210> SEQ ID NO 448
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 448

Lys Gln Pro Asp Leu Ser Lys Tyr Lys Asn
1               5                   10

<210> SEQ ID NO 449
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 449

Lys Gln Ser Thr Thr Met Gly Gly Asp Ser Lys Leu
1               5                   10

<210> SEQ ID NO 450
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 450

Arg Gln Asn Ser Arg Gln Gln Asp Arg Arg
1               5                   10

<210> SEQ ID NO 451
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 451

Lys Gln Ser Thr Thr Met Gly Gly Asp Ser Lys Leu
1               5                   10

<210> SEQ ID NO 452
<211> LENGTH: 10
<212> TYPE: PRT
<213> ORGANISM: Artificial Sequence
<220> FEATURE:
<223> OTHER INFORMATION: Description of Artificial Sequence; NOTE =

Synthetic Construct

<400> SEQUENCE: 452

Arg Gln Gln Asp Arg Arg Gln Asn Lys Lys
1               5                   10

<210> SEQ ID NO 453
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 453

Lys Lys Gln Pro Asp Leu Ser Lys Tyr Lys Asn
1               5                   10

<210> SEQ ID NO 454
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 454

Lys Thr Pro Asp Glu Glu Arg Ile Phe Arg Thr
1               5                   10

<210> SEQ ID NO 455
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 455

Arg Gly Glu Ser Leu Pro Pro Ala Thr Leu Ala Gly Arg Gln
1               5                   10

<210> SEQ ID NO 456
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 456

Arg Gln Asn Lys Lys Gln Pro Asp Leu Ser Lys Tyr
1               5                   10

<210> SEQ ID NO 457
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 457

Arg Gln Asn Ser Arg Gln Gln Asp Arg Arg Gln
1               5                   10

<210> SEQ ID NO 458
<211> LENGTH: 15

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 458

Lys Gly Gly Asp Arg Gly Ser Lys Ser Thr Pro Ser Gly Lys Glu
1               5                   10                  15

<210> SEQ ID NO 459
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 459

Lys Glu Ser His Pro Thr Ala Thr Gln Thr Ser Gly Arg Arg
1               5                   10

<210> SEQ ID NO 460
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 460

Lys Tyr Ile Phe Thr Thr Gly Asn Val Asp Ser Gly Lys Thr
1               5                   10

<210> SEQ ID NO 461
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 461

Lys Gln Pro Asp Leu Ser Lys Tyr Lys Asn Ser Pro Ala Lys Tyr
1               5                   10                  15

<210> SEQ ID NO 462
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 462

Lys Thr Pro Asp Glu Glu Arg Ile Phe Arg Thr Asn Arg Ala
1               5                   10

<210> SEQ ID NO 463
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 463

Lys Leu Ile Leu Asp Asn Pro Asn Arg Asn Thr Ile Val Gly Arg Ile
1               5                   10                  15
```

<210> SEQ ID NO 464
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 464

Arg Gly Glu Ser Leu Pro Pro Ala Thr Leu Ala Gly Arg Gln Asn Ser
1               5                   10                  15

Arg Gln

<210> SEQ ID NO 465
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 465

Lys Phe Tyr Pro Asp Ile Ser Asp Asp Asn Ile Asn Glu Val Val Arg
1               5                   10                  15

Asp

<210> SEQ ID NO 466
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 466

Lys Asn Ser Pro Ala Lys Tyr Ile Phe Thr Thr Gly Asn Val Asp Ser
1               5                   10                  15

Gly Lys Thr

<210> SEQ ID NO 467
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 467

Lys Ser Thr Pro Ser Gly Lys Glu Ser His Pro Thr Ala Thr Gln Thr
1               5                   10                  15

Ser Gly Arg Arg
            20

<210> SEQ ID NO 468
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 468

Lys Leu Ile Leu Asp Asn Pro Asn Arg Asn Thr Ile Val Gly Arg Ile
1               5                   10                  15

Lys Thr

<210> SEQ ID NO 469
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 469

Lys Gln Ser Thr Thr Met Gly Gly Asp Ser Lys Leu Ile Leu Asp Asn
1               5                   10                  15

Pro Asn Arg Asn
            20

<210> SEQ ID NO 470
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 470

Arg Arg Pro Ser Gln Ser Pro Arg Gly Glu Ser Leu Pro Pro Ala Thr
1               5                   10                  15

Leu Ala Gly Arg Gln
            20

<210> SEQ ID NO 471
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 471

Lys Tyr Ile Phe Thr Thr Gly Asn Val Asp Ser Gly Lys Thr Pro Asp
1               5                   10                  15

Glu Glu Arg Ile
            20

<210> SEQ ID NO 472
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 472

Arg Arg Pro Ser Gln Ser Pro Cys Gly Glu Ser Arg Pro Ser Gly Ser
1               5                   10                  15

Ala Thr Ser Gly Arg Arg
            20

<210> SEQ ID NO 473
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 473

Lys Tyr Lys Asn Ser Pro Ala Lys Tyr Ile Phe Thr Thr Gly Asn Val
1               5                   10                  15

Asp Ser Gly Lys Thr
            20

<210> SEQ ID NO 474
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 474

Arg Gly Ser Lys Ser Thr Pro Ser Gly Lys Glu Ser His Pro Thr Ala
1               5                   10                  15

Thr Gln Thr Ser Gly Arg Arg
            20

<210> SEQ ID NO 475
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 475

Lys Asp Phe Pro Val Pro Phe Val Ser Glu Gln Thr Asp Asp Phe Tyr
1               5                   10                  15

Asp Asp Lys Phe
            20

<210> SEQ ID NO 476
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 476

Arg Gly Glu Ser Leu Pro Pro Ala Thr Leu Ala Gly Arg Gln Asn Ser
1               5                   10                  15

Arg Gln Gln Asp Arg Arg
            20

<210> SEQ ID NO 477
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 477

Lys Phe Tyr Pro Asp Ile Ser Asp Asp Asn Ile Asn Glu Val Val Arg
1               5                   10                  15

Asp Asn Gly Arg Lys
            20

<210> SEQ ID NO 478
<211> LENGTH: 22
<212> TYPE: PRT
<213> ORGANISM: Artificial Sequence

```
<220> FEATURE:
<223> OTHER INFORMATION: Description of Artificial Sequence; NOTE =
      Synthetic Construct

<400> SEQUENCE: 478

Lys Phe Tyr Pro Asp Ile Ser Asp Asp Asn Ile Asn Glu Val Val Arg
1               5                   10                  15

Asp Asn Gly Arg Lys Gly
            20

<210> SEQ ID NO 479
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 479

Lys Tyr Ile Phe Thr Thr Gly Asn Val Asp Ser Gly Lys Thr Pro Asp
1               5                   10                  15

Glu Glu Arg Ile Phe Arg Thr
            20

<210> SEQ ID NO 480
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 480

Arg Arg Pro Ser Gln Ser Pro Arg Gly Glu Ser Leu Pro Pro Ala Thr
1               5                   10                  15

Leu Ala Gly Arg Gln Asn Ser Arg Gln
            20                  25

<210> SEQ ID NO 481
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 481

Lys Asn Ser Pro Ala Lys Tyr Ile Phe Thr Thr Gly Asn Val Asp Ser
1               5                   10                  15

Gly Lys Thr Pro Asp Glu Glu Arg Ile
            20                  25

<210> SEQ ID NO 482
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 482

Lys Gln Ser Thr Thr Met Gly Gly Asp Ser Lys Leu Ile Leu Asp Asn
1               5                   10                  15

Pro Asn Arg Asn Thr Ile Val Gly Arg Ile
            20                  25
```

```
<210> SEQ ID NO 483
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 483

Arg Arg Pro Ser Gln Ser Pro Cys Gly Glu Ser Arg Pro Ser Gly Ser
 1               5                  10                  15

Ala Thr Ser Gly Arg Arg Pro Ser Gln Ser Pro Arg Gly
            20                  25

<210> SEQ ID NO 484
<211> LENGTH: 32
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 484

Arg Ala Glu Tyr Val Leu Ala Thr Gly Gly Pro Tyr Asp Asn Tyr Val
 1               5                  10                  15

Val Glu Ile Ile Asp Gly Pro Asn Pro Asn Asp Ile Ser Leu Lys Gln
            20                  25                  30

<210> SEQ ID NO 485
<211> LENGTH: 34
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 485

Lys Glu Ser His Pro Thr Ala Thr Gln Thr Ser Gly Arg Arg Pro Ser
 1               5                  10                  15

Gln Ser Pro Cys Gly Glu Ser Arg Pro Ser Gly Ser Ala Thr Ser Gly
            20                  25                  30

Arg Arg

<210> SEQ ID NO 486
<211> LENGTH: 34
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 486

Ser Gly His Ile Leu Thr Val Gly Leu Ile Val Val Val Ala His Cys
 1               5                  10                  15

Ala Thr Leu Ser Ser Ser Ala Ser Thr Ile Pro Ile Gln Ser Gln Gly
            20                  25                  30

Lys Asp

<210> SEQ ID NO 487
<211> LENGTH: 35
<212> TYPE: PRT
<213> ORGANISM: Artificial Sequence
<220> FEATURE:
<223> OTHER INFORMATION: Description of Artificial Sequence; NOTE =
      Synthetic Construct
```

```
<400> SEQUENCE: 487

Met Ser Gly His Ile Leu Thr Val Gly Leu Ile Val Val Ala His
1               5                   10                  15

Cys Ala Thr Leu Ser Ser Ser Ala Ser Thr Ile Pro Ile Gln Ser Gln
            20                  25                  30

Gly Lys Asp
        35

<210> SEQ ID NO 488
<211> LENGTH: 35
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 488

Arg Thr Asn Arg Ala Glu Tyr Val Leu Ala Thr Gly Gly Pro Tyr Asp
1               5                   10                  15

Asn Tyr Val Val Glu Ile Ile Asp Gly Pro Asn Pro Asn Asp Ile Ser
            20                  25                  30

Leu Lys Gln
        35

<210> SEQ ID NO 489
<211> LENGTH: 40
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 489

Lys Ser Thr Pro Ser Gly Lys Glu Ser His Pro Thr Ala Thr Gln Thr
1               5                   10                  15

Ser Gly Arg Arg Pro Ser Gln Ser Pro Cys Gly Glu Ser Arg Pro Ser
            20                  25                  30

Gly Ser Ala Thr Ser Gly Arg Arg
        35                  40

<210> SEQ ID NO 490
<211> LENGTH: 35
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 490

Lys Asp Phe Pro Val Pro Phe Val Ser Glu Gln Thr Asp Asp Phe Tyr
1               5                   10                  15

Asp Asp Lys Phe Tyr Pro Asp Ile Ser Asp Asp Asn Ile Asn Glu Val
            20                  25                  30

Val Arg Asp
        35

<210> SEQ ID NO 491
<211> LENGTH: 38
<212> TYPE: PRT
<213> ORGANISM: Artificial Sequence
<220> FEATURE:
<223> OTHER INFORMATION: Description of Artificial Sequence; NOTE =
      Synthetic Construct
```

<400> SEQUENCE: 491

Arg Ile Phe Arg Thr Asn Arg Ala Glu Tyr Val Leu Ala Thr Gly Gly
1               5                   10                  15

Pro Tyr Asp Asn Tyr Val Val Glu Ile Ile Asp Gly Pro Asn Pro Asn
            20                  25                  30

Asp Ile Ser Leu Lys Gln
        35

<210> SEQ ID NO 492
<211> LENGTH: 41
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 492

Arg Arg Pro Ser Gln Ser Pro Cys Gly Glu Ser Arg Pro Ser Gly Ser
1               5                   10                  15

Ala Thr Ser Gly Arg Arg Pro Ser Gln Ser Pro Arg Gly Glu Ser Leu
            20                  25                  30

Pro Pro Ala Thr Leu Ala Gly Arg Gln
        35                  40

<210> SEQ ID NO 493
<211> LENGTH: 41
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 493

Lys Glu Ser His Pro Thr Ala Thr Gln Thr Ser Gly Arg Arg Pro Ser
1               5                   10                  15

Gln Ser Pro Cys Gly Glu Ser Arg Pro Ser Gly Ser Ala Thr Ser Gly
            20                  25                  30

Arg Arg Pro Ser Gln Ser Pro Arg Gly
        35                  40

<210> SEQ ID NO 494
<211> LENGTH: 42
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 494

Arg Ala Glu Tyr Val Leu Ala Thr Gly Gly Pro Tyr Asp Asn Tyr Val
1               5                   10                  15

Val Glu Ile Ile Asp Gly Pro Asn Pro Asn Asp Ile Ser Leu Lys Gln
            20                  25                  30

Ser Thr Thr Met Gly Gly Asp Ser Lys Leu
        35                  40

<210> SEQ ID NO 495
<211> LENGTH: 39
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 495

Lys Asp Phe Pro Val Pro Phe Val Ser Glu Gln Thr Asp Asp Phe Tyr
1               5                   10                  15

Asp Asp Lys Phe Tyr Pro Asp Ile Ser Asp Asp Asn Ile Asn Glu Val
            20                  25                  30

Val Arg Asp Asn Gly Arg Lys
        35

<210> SEQ ID NO 496
<211> LENGTH: 45
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 496

Arg Thr Asn Arg Ala Glu Tyr Val Leu Ala Thr Gly Gly Pro Tyr Asp
1               5                   10                  15

Asn Tyr Val Val Glu Ile Ile Asp Gly Pro Asn Pro Asn Asp Ile Ser
            20                  25                  30

Leu Lys Gln Ser Thr Thr Met Gly Gly Asp Ser Lys Leu
        35                  40                  45

<210> SEQ ID NO 497
<211> LENGTH: 50
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 497

Arg Ala Glu Tyr Val Leu Ala Thr Gly Gly Pro Tyr Asp Asn Tyr Val
1               5                   10                  15

Val Glu Ile Ile Asp Gly Pro Asn Pro Asn Asp Ile Ser Leu Lys Gln
            20                  25                  30

Ser Thr Thr Met Gly Gly Asp Ser Lys Leu Ile Leu Asp Asn Pro Asn
        35                  40                  45

Arg Asn
    50

<210> SEQ ID NO 498
<211> LENGTH: 52
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 498

Ser Gly His Ile Leu Thr Val Gly Leu Ile Val Val Ala His Cys
1               5                   10                  15

Ala Thr Leu Ser Ser Ser Ala Ser Thr Ile Pro Ile Gln Ser Gln Gly
            20                  25                  30

Lys Asp Phe Pro Val Pro Phe Val Ser Glu Gln Thr Asp Asp Phe Tyr
        35                  40                  45

Asp Asp Lys Phe
    50

<210> SEQ ID NO 499

<211> LENGTH: 53
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 499

Met Ser Gly His Ile Leu Thr Val Gly Leu Ile Val Val Val Ala His
1               5                   10                  15

Cys Ala Thr Leu Ser Ser Ser Ala Ser Thr Ile Pro Ile Gln Ser Gln
            20                  25                  30

Gly Lys Asp Phe Pro Val Pro Phe Val Ser Glu Gln Thr Asp Asp Phe
        35                  40                  45

Tyr Asp Asp Lys Phe
    50

<210> SEQ ID NO 500
<211> LENGTH: 67
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 500

Ser Gly His Ile Leu Thr Val Gly Leu Ile Val Val Val Ala His Cys
1               5                   10                  15

Ala Thr Leu Ser Ser Ser Ala Ser Thr Ile Pro Ile Gln Ser Gln Gly
            20                  25                  30

Lys Asp Phe Pro Val Pro Phe Val Ser Glu Gln Thr Asp Asp Phe Tyr
        35                  40                  45

Asp Asp Lys Phe Tyr Pro Asp Ile Ser Asp Asp Asn Ile Asn Glu Val
    50                  55                  60

Val Arg Asp
65

<210> SEQ ID NO 501
<211> LENGTH: 66
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 501

Met Ser Gly His Ile Leu Thr Val Gly Leu Ile Val Val Val Ala His
1               5                   10                  15

Cys Ala Thr Leu Ser Ser Ser Ala Ser Thr Ile Pro Ile Gln Ser Gln
            20                  25                  30

Gly Lys Asp Phe Pro Val Pro Phe Val Ser Glu Gln Thr Asp Asp Phe
        35                  40                  45

Tyr Asp Asp Lys Phe Tyr Pro Asp Ile Ser Asp Asp Asn Glu Val Val
    50                  55                  60

Arg Asp
65

<210> SEQ ID NO 502
<211> LENGTH: 7
<212> TYPE: PRT
<213> ORGANISM: Artificial Sequence
<220> FEATURE:
<223> OTHER INFORMATION: Description of Artificial Sequence; NOTE =

Synthetic Construct

<400> SEQUENCE: 502

Lys Ser Ile Ser Pro Lys Asn
1               5

<210> SEQ ID NO 503
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 503

Lys Ser Ile Gln Ile Lys Gly
1               5

<210> SEQ ID NO 504
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 504

Lys Lys Ser Ile Ser Pro Lys Asn
1               5

<210> SEQ ID NO 505
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 505

Lys Gly Lys Ser Ile Asn Arg Ala
1               5

<210> SEQ ID NO 506
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 506

Lys Ile Lys Ser Ala Met Lys Ile
1               5

<210> SEQ ID NO 507
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 507

Lys Ser Gly Ile Val Phe Arg Leu
1               5

<210> SEQ ID NO 508
<211> LENGTH: 7

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 508

Lys Glu Gln Tyr Asp Lys Ile
1               5

<210> SEQ ID NO 509
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 509

Lys Ile Lys Ser Ala Met Lys Ile
1               5

<210> SEQ ID NO 510
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 510

Lys Tyr Ser Val Lys Met Lys Lys
1               5

<210> SEQ ID NO 511
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 511

Lys Tyr Ala Tyr Lys Gly Arg Gly
1               5

<210> SEQ ID NO 512
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 512

Lys Asn Asp Asn Asn Tyr Lys Ser
1               5

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 513

Lys Ser Ile Gln Ile Lys Gly Lys Ser
1               5
```

```
<210> SEQ ID NO 514
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 514

Lys Tyr Ser Val Lys Met Lys Lys
1               5

<210> SEQ ID NO 515
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 515

Lys Ser Thr Glu Gly Phe Leu Lys Arg
1               5

<210> SEQ ID NO 516
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 516

Lys Glu Ile Asp Gln Asp Gly Lys Val
1               5

<210> SEQ ID NO 517
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 517

Lys Ala Glu Trp Ala Thr Thr Lys Gly
1               5

<210> SEQ ID NO 518
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 518

Arg Ala Ala Gly Phe Ser Ser Phe Lys Phe
1               5                   10

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct
```

```
<400> SEQUENCE: 519

Lys Thr Ile Glu Lys Asp Asp Lys Thr
1               5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 520

Lys Val Gln Ser Leu Asp Trp Lys Glu
1               5

<210> SEQ ID NO 521
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 521

Lys Tyr Ser Val Lys Met Lys Lys Glu
1               5

<210> SEQ ID NO 522
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 522

Lys Leu Tyr Thr Phe Asp Asp Lys Ser
1               5

<210> SEQ ID NO 523
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 523

Lys Ser Gly Ile Val Phe Arg Leu Lys Thr
1               5                   10

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 524

Lys Glu Gln Tyr Asp Lys Ile Lys Ser
1               5

<210> SEQ ID NO 525
<211> LENGTH: 10
<212> TYPE: PRT
<213> ORGANISM: Artificial Sequence
```

```
<220> FEATURE:
<223> OTHER INFORMATION: Description of Artificial Sequence; NOTE =
      Synthetic Construct

<400> SEQUENCE: 525

Lys Tyr Glu Gly Ile Val Leu Leu Lys Ser
1               5                   10

<210> SEQ ID NO 526
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 526

Lys Ser Thr Glu Gly Phe Leu Lys Arg Ser
1               5                   10

<210> SEQ ID NO 527
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 527

Lys Glu Asp His Glu Ile Phe Thr Lys Tyr
1               5                   10

<210> SEQ ID NO 528
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 528

Lys Val Gly Glu Leu Ile Glu Val Gly Asp Lys Tyr
1               5                   10

<210> SEQ ID NO 529
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 529

Lys Asn Gln Trp Val Phe Leu Pro Arg Lys
1               5                   10

<210> SEQ ID NO 530
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 530

Lys Thr Glu Glu Thr Ile Gly Cys Asn Lys Ile
1               5                   10
```

```
<210> SEQ ID NO 531
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 531

Lys Leu Asn Ser Asn Ser Leu Trp Ile Lys Glu
 1               5                  10

<210> SEQ ID NO 532
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 532

Lys Ala Glu Trp Ala Thr Thr Lys Gly Asp Lys Met
 1               5                  10

<210> SEQ ID NO 533
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 533

Lys Lys Glu Asp His Glu Ile Phe Thr Lys Tyr
 1               5                  10

<210> SEQ ID NO 534
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 534

Lys Ser Thr Glu Gly Phe Leu Lys Arg Ser Gln
 1               5                  10

<210> SEQ ID NO 535
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 535

Lys Cys Ser Glu Arg Pro Phe Asp Thr Lys Thr
 1               5                  10

<210> SEQ ID NO 536
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 536
```

Lys Asn Gln Trp Val Phe Leu Pro Arg Lys Cys
 1               5                  10

<210> SEQ ID NO 537
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 537

Lys Asn Asp Asn Asn Tyr Lys Ser Ile Val Lys Val
 1               5                  10

<210> SEQ ID NO 538
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 538

Lys Trp Lys Leu Tyr Thr Phe Asp Asp Lys Ser
 1               5                  10

<210> SEQ ID NO 539
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 539

Lys Ser Ile Gln Ile Lys Gly Lys Ser Ile Asn Arg Ala
 1               5                  10

<210> SEQ ID NO 540
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 540

Arg Gly Ala Glu Leu Ser Glu Phe Leu Ile Tyr Lys Trp
 1               5                  10

<210> SEQ ID NO 541
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 541

Lys Ser Ile Ser Pro Lys Asn Asp Asn Asn Tyr Lys Ser
 1               5                  10

<210> SEQ ID NO 542
<211> LENGTH: 12
<212> TYPE: PRT
<213> ORGANISM: Artificial Sequence
<220> FEATURE:
<223> OTHER INFORMATION: Description of Artificial Sequence; NOTE =

-continued

```
      Synthetic Construct

<400> SEQUENCE: 542

Arg Lys Cys Ser Glu Arg Pro Phe Asp Thr Lys Thr
 1               5                  10

<210> SEQ ID NO 543
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 543

Lys Ser Ile Asn Arg Ala Ala Gly Phe Ser Ser Phe Lys Phe
 1               5                  10

<210> SEQ ID NO 544
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 544

Lys Leu Lys Asn Gln Trp Val Phe Leu Pro Arg Lys
 1               5                  10

<210> SEQ ID NO 545
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 545

Lys Glu Gln Tyr Asp Lys Ile Lys Ser Ala Met Lys Ile
 1               5                  10

<210> SEQ ID NO 546
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 546

Lys Thr Gly Lys Leu Asn Ser Asn Ser Leu Trp Ile Lys Glu
 1               5                  10

<210> SEQ ID NO 547
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 547

Lys Ile Ile Ile Ala Ser Glu Asn Phe Glu Ile Ile Lys Ser
 1               5                  10

<210> SEQ ID NO 548
<211> LENGTH: 14
```

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 548

Arg Val Leu Met Pro Glu Met Gln Ile Asn Ser Asp Lys Tyr
1               5                  10

<210> SEQ ID NO 549
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 549

Lys Met Tyr Val Gly Ser Thr Gly Ile Ser Phe Thr Asp Lys Thr
1               5                  10                  15

<210> SEQ ID NO 550
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 550

Lys Met Lys Lys Glu Asp His Glu Ile Phe Thr Lys Tyr
1               5                  10

<210> SEQ ID NO 551
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 551

Lys Lys Ser Ile Ser Pro Lys Asn Asp Asn Asn Tyr Lys Ser
1               5                  10

<210> SEQ ID NO 552
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 552

Arg Val Leu Met Pro Glu Met Gln Ile Asn Ser Asp Lys Tyr
1               5                  10

<210> SEQ ID NO 553
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 553

Lys Thr Ala Thr Tyr Ile Thr Val Ile Asp Ile Thr Gly Arg Val
1               5                  10                  15
```

```
<210> SEQ ID NO 554
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 554

Lys Leu Lys Asn Gln Trp Val Phe Leu Pro Arg Lys Cys
1               5                   10

<210> SEQ ID NO 555
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 555

Arg Val Leu Met Pro Glu Met Gln Ile Asn Ser Asp Lys Tyr
1               5                   10

<210> SEQ ID NO 556
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 556

Lys Gly Lys Ser Ile Asn Arg Ala Ala Gly Phe Ser Ser Phe Lys Phe
1               5                   10                  15

<210> SEQ ID NO 557
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 557

Lys Gly Arg Gly Ala Glu Leu Ser Glu Phe Leu Ile Tyr Lys Trp
1               5                   10                  15

<210> SEQ ID NO 558
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 558

Lys Ser Ile Val Lys Val Gly Glu Leu Ile Glu Val Gly Asp Lys Tyr
1               5                   10                  15

<210> SEQ ID NO 559
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct
```

-continued

```
<400> SEQUENCE: 559

Lys Val Gly Glu Leu Ile Glu Val Gly Asp Lys Tyr Ser Val Lys Met
1               5                   10                  15

<210> SEQ ID NO 560
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 560

Lys Val Gln Ser Leu Asp Trp Lys Glu Gln Tyr Asp Lys Ile
1               5                   10

<210> SEQ ID NO 561
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 561

Lys Glu Asp His Glu Ile Phe Thr Lys Tyr Ala Tyr Lys Gly
1               5                   10

<210> SEQ ID NO 562
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 562

Lys Leu Tyr Thr Phe Asp Asp Lys Ser Gly Ile Val Phe Arg Leu
1               5                   10                  15

<210> SEQ ID NO 563
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 563

Arg Gly Ala Glu Leu Ser Glu Phe Leu Ile Tyr Lys Trp Lys Leu
1               5                   10                  15

<210> SEQ ID NO 564
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 564

Lys Phe Leu Pro Asp Ser Asp Asp Gln Ile Leu Leu Ala Leu Lys Thr
1               5                   10                  15

<210> SEQ ID NO 565
<211> LENGTH: 17
<212> TYPE: PRT
<213> ORGANISM: Artificial Sequence
```

```
<220> FEATURE:
<223> OTHER INFORMATION: Description of Artificial Sequence; NOTE =
      Synthetic Construct

<400> SEQUENCE: 565

Arg Ser Gly Thr Ile Tyr Asn Phe Ala Ile Ala Asp Leu Asp Lys
 1               5                  10                  15

Lys

<210> SEQ ID NO 566
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 566

Lys Glu Ile Asp Gln Asp Gly Lys Val Gln Ser Leu Asp Trp Lys Glu
 1               5                  10                  15

<210> SEQ ID NO 567
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 567

Lys Lys Glu Asp His Glu Ile Phe Thr Lys Tyr Ala Tyr Lys Gly
 1               5                  10                  15

<210> SEQ ID NO 568
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 568

Lys Met Tyr Val Gly Ser Thr Gly Ile Ser Phe Thr Asp Lys Thr Gly
 1               5                  10                  15

Lys Leu

<210> SEQ ID NO 569
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 569

Lys Tyr Glu Gly Ile Val Leu Leu Lys Ser Thr Glu Gly Phe Leu Lys
 1               5                  10                  15

Arg

<210> SEQ ID NO 570
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct
```

```
<400> SEQUENCE: 570

Lys Gly Asp Lys Met Tyr Val Gly Ser Thr Gly Ile Ser Phe Thr Asp
 1               5                  10                  15

Lys Thr

<210> SEQ ID NO 571
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 571

Lys Ser Ile Ser Pro Lys Asn Asp Asn Asn Tyr Lys Ser Ile Val Lys
 1               5                  10                  15

Val

<210> SEQ ID NO 572
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 572

Lys Met Tyr Val Gly Ser Thr Gly Ile Ser Phe Thr Asp Lys Thr Gly
 1               5                  10                  15

Lys Leu

<210> SEQ ID NO 573
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 573

Lys Gly Asp Lys Met Tyr Val Gly Ser Thr Gly Ile Ser Phe Thr Asp
 1               5                  10                  15

Lys Thr

<210> SEQ ID NO 574
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 574

Lys Glu Asp His Glu Ile Phe Thr Lys Tyr Ala Tyr Lys Gly Arg Gly
 1               5                  10                  15

<210> SEQ ID NO 575
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 575
```

-continued

Arg Ser Gly Thr Ile Tyr Asn Phe Ala Ile Ile Ala Asp Leu Asp Lys
1               5                   10                  15

Lys Ser

<210> SEQ ID NO 576
<211> LENGTH: 16
<212> TYPE: PRT
<213> ORGANISM: Artificial Sequence
<220> FEATURE:
<223> OTHER INFORMATION: Description of Artificial Sequence; NOTE = 
      Synthetic Construct

<400> SEQUENCE: 576

Lys Val Gln Ser Leu Asp Trp Lys Glu Gln Tyr Asp Lys Ile Lys Ser
1               5                   10                  15

<210> SEQ ID NO 577
<211> LENGTH: 18
<212> TYPE: PRT
<213> ORGANISM: Artificial Sequence
<220> FEATURE:
<223> OTHER INFORMATION: Description of Artificial Sequence; NOTE = 
      Synthetic Construct

<400> SEQUENCE: 577

Lys Asp Asp Lys Thr Ala Thr Tyr Ile Thr Val Ile Asp Ile Thr Gly
1               5                   10                  15

Arg Val

<210> SEQ ID NO 578
<211> LENGTH: 18
<212> TYPE: PRT
<213> ORGANISM: Artificial Sequence
<220> FEATURE:
<223> OTHER INFORMATION: Description of Artificial Sequence; NOTE = 
      Synthetic Construct

<400> SEQUENCE: 578

Lys Val Gly Glu Leu Ile Glu Val Gly Asp Lys Tyr Ser Val Lys Met
1               5                   10                  15

Lys Lys

<210> SEQ ID NO 579
<211> LENGTH: 17
<212> TYPE: PRT
<213> ORGANISM: Artificial Sequence
<220> FEATURE:
<223> OTHER INFORMATION: Description of Artificial Sequence; NOTE = 
      Synthetic Construct

<400> SEQUENCE: 579

Lys Gly Arg Gly Ala Glu Leu Ser Glu Phe Leu Ile Tyr Lys Trp Lys
1               5                   10                  15

Leu

<210> SEQ ID NO 580
<211> LENGTH: 17
<212> TYPE: PRT
<213> ORGANISM: Artificial Sequence
<220> FEATURE:
<223> OTHER INFORMATION: Description of Artificial Sequence; NOTE = 
      Synthetic Construct

<400> SEQUENCE: 580

Lys Ile Pro Asn Gly Phe Ile Trp His Glu Ala Val Asn Trp Ser Lys
1               5                   10                  15

Leu

<210> SEQ ID NO 581
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 581

Lys Leu Tyr Thr Phe Asp Asp Lys Ser Gly Ile Val Phe Arg Leu Lys
 1               5                  10                  15

Thr

<210> SEQ ID NO 582
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 582

Lys Tyr Glu Gly Ile Val Leu Leu Lys Ser Thr Glu Gly Phe Leu Lys
 1               5                  10                  15

Arg Ser

<210> SEQ ID NO 583
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 583

Lys Leu Asn Ser Asn Ser Leu Trp Ile Lys Glu Ile Asp Gln Asp Gly
 1               5                  10                  15

Lys Val

<210> SEQ ID NO 584
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 584

Lys Trp Lys Leu Tyr Thr Phe Asp Asp Lys Ser Gly Ile Val Phe Arg
 1               5                  10                  15

Leu

<210> SEQ ID NO 585
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 585

Lys Ile Ile Ile Ala Ser Glu Asn Phe Glu Ile Ile Lys Ser Ile Gln
 1               5                  10                  15

Ile Lys Gly

<210> SEQ ID NO 586
<211> LENGTH: 20
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 586

Lys Ser Ile Val Lys Val Gly Glu Leu Ile Glu Val Gly Asp Lys Tyr
1               5                   10                  15

Ser Val Lys Met
            20

<210> SEQ ID NO 587
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 587

Lys Gly Asp Lys Met Tyr Val Gly Ser Thr Gly Ile Ser Phe Thr Asp
1               5                   10                  15

Lys Thr Gly Lys Leu
            20

<210> SEQ ID NO 588
<211> LENGTH: 19
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 588

Lys Tyr Ala Tyr Lys Gly Arg Gly Ala Glu Leu Ser Glu Phe Leu Ile
1               5                   10                  15

Tyr Lys Trp

<210> SEQ ID NO 589
<211> LENGTH: 19
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 589

Lys Ile Pro Asn Gly Phe Ile Trp His Glu Ala Val Asn Trp Ser Lys
1               5                   10                  15

Leu Lys Asn

<210> SEQ ID NO 590
<211> LENGTH: 20
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 590

```
Lys Phe Leu Pro Asp Ser Asp Asp Gln Ile Leu Leu Ala Leu Lys Thr
 1               5                  10                  15

Ile Glu Lys Asp
            20
```

<210> SEQ ID NO 591
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 591

```
Lys Ile Ile Ile Ala Ser Glu Asn Phe Glu Ile Ile Lys Ser Ile Gln
 1               5                  10                  15

Ile Lys Gly Lys Ser
            20
```

<210> SEQ ID NO 592
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 592

```
Lys Thr Gly Lys Leu Asn Ser Asn Ser Leu Trp Ile Lys Glu Ile Asp
 1               5                  10                  15

Gln Asp Gly Lys Val
            20
```

<210> SEQ ID NO 593
<211> LENGTH: 20
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 593

```
Lys Cys Ser Glu Arg Pro Phe Asp Thr Lys Thr Glu Glu Thr Ile Gly
 1               5                  10                  15

Cys Asn Lys Ile
            20
```

<210> SEQ ID NO 594
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 594

```
Lys Ser Ala Met Lys Ile Pro Asn Gly Phe Ile Trp His Glu Ala Val
 1               5                  10                  15

Asn Trp Ser Lys Leu
            20
```

<210> SEQ ID NO 595
<211> LENGTH: 22
<212> TYPE: PRT
<213> ORGANISM: Artificial Sequence
<220> FEATURE:

```
<223> OTHER INFORMATION: Description of Artificial Sequence; NOTE =
      Synthetic Construct

<400> SEQUENCE: 595

Lys Asn Asp Asn Asn Tyr Lys Ser Ile Val Lys Val Gly Glu Leu Ile
1               5                   10                  15

Glu Val Gly Asp Lys Tyr
            20

<210> SEQ ID NO 596
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 596

Lys Thr Ile Glu Lys Asp Asp Lys Thr Ala Thr Tyr Ile Thr Val Ile
1               5                   10                  15

Asp Ile Thr Gly Arg Val
            20

<210> SEQ ID NO 597
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 597

Lys Phe Cys Ile Val Ala Phe Ala Ile Cys Leu Ser Ile Asn Leu Ser
1               5                   10                  15

Glu Gly Ala Pro Arg Ser
            20

<210> SEQ ID NO 598
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 598

Arg Ser Gly Thr Ile Tyr Asn Phe Ala Ile Ile Ala Asp Leu Asp Lys
1               5                   10                  15

Lys Ser Ile Ser Pro Lys Asn
            20

<210> SEQ ID NO 599
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 599

Arg Val Leu Met Pro Glu Met Gln Ile Asn Ser Asp Lys Tyr Glu Gly
1               5                   10                  15

Ile Val Leu Leu Lys Ser
            20
```

-continued

```
<210> SEQ ID NO 600
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 600

Lys Asn Gln Trp Val Phe Leu Pro Arg Lys Cys Ser Glu Arg Pro Phe
 1               5                  10                  15

Asp Thr Lys Thr
            20

<210> SEQ ID NO 601
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 601

Lys Glu Ile Asp Gln Asp Gly Lys Val Gln Ser Leu Asp Trp Lys Glu
 1               5                  10                  15

Gln Tyr Asp Lys Ile
            20

<210> SEQ ID NO 602
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 602

Arg Lys Cys Ser Glu Arg Pro Phe Asp Thr Lys Thr Glu Glu Thr Ile
 1               5                  10                  15

Gly Cys Asn Lys Ile
            20

<210> SEQ ID NO 603
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 603

Arg Val Leu Met Pro Glu Met Gln Ile Asn Ser Asp Lys Tyr Glu Gly
 1               5                  10                  15

Ile Val Leu Leu Lys Ser
            20

<210> SEQ ID NO 604
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 604

Arg Ala Ala Gly Phe Ser Ser Phe Lys Phe Leu Pro Asp Ser Asp Asp
 1               5                  10                  15
```

Gln Ile Leu Leu Ala Leu Lys Thr
            20

<210> SEQ ID NO 605
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 605

Lys Phe Leu Pro Asp Ser Asp Asp Gln Ile Leu Leu Ala Leu Lys Thr
1               5                   10                  15

Ile Glu Lys Asp Asp Lys Thr
            20

<210> SEQ ID NO 606
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 606

Lys Thr Glu Glu Thr Ile Gly Cys Asn Lys Ile Ile Ala Ser Glu
1               5                   10                  15

Asn Phe Glu Ile Ile Lys Ser
            20

<210> SEQ ID NO 607
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 607

Lys Thr Asn Ala Asp Leu Ile Pro Trp Val Thr Leu Ala Asn Gly Asn
1               5                   10                  15

Gly Asp Gln Thr Asp Gly Phe Lys Ala
            20                  25

<210> SEQ ID NO 608
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 608

Lys Ile Lys Ser Ala Met Lys Ile Pro Asn Gly Phe Ile Trp His Glu
1               5                   10                  15

Ala Val Asn Trp Ser Lys Leu
            20

<210> SEQ ID NO 609
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

```
<400> SEQUENCE: 609

Lys Ser Ala Met Lys Ile Pro Asn Gly Phe Ile Trp His Glu Ala Val
1               5                   10                  15
Asn Trp Ser Lys Leu Lys Asn
            20

<210> SEQ ID NO 610
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 610

Arg Gly Ala Glu Leu Ser Glu Phe Leu Ile Tyr Lys Trp Lys Leu Tyr
1               5                   10                  15
Thr Phe Asp Asp Lys Ser
            20

<210> SEQ ID NO 611
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 611

Lys Ala Glu Trp Ala Thr Thr Lys Gly Asp Lys Met Tyr Val Gly Ser
1               5                   10                  15
Thr Gly Ile Ser Phe Thr Asp Lys Thr
            20                  25

<210> SEQ ID NO 612
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 612

Arg Leu Lys Thr Asn Ala Asp Leu Ile Pro Trp Val Thr Leu Ala Asn
1               5                   10                  15
Gly Asn Gly Asp Gln Thr Asp Gly Phe Lys Ala
            20                  25

<210> SEQ ID NO 613
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 613

Phe Leu Lys Phe Cys Ile Val Ala Phe Ala Ile Cys Leu Ser Ile Asn
1               5                   10                  15
Leu Ser Glu Gly Ala Pro Arg Ser
            20

<210> SEQ ID NO 614
<211> LENGTH: 25
```

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 614

Lys Leu Asn Ser Asn Ser Leu Trp Ile Lys Glu Ile Asp Gln Asp Gly
 1               5                  10                  15

Lys Val Gln Ser Leu Asp Trp Lys Glu
            20                  25

<210> SEQ ID NO 615
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 615

Lys Met Tyr Val Gly Ser Thr Gly Ile Ser Phe Thr Asp Lys Thr Gly
 1               5                  10                  15

Lys Leu Asn Ser Asn Ser Leu Trp Ile Lys Glu
            20                  25

<210> SEQ ID NO 616
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 616

Met Phe Leu Lys Phe Cys Ile Val Ala Phe Ala Ile Cys Leu Ser Ile
 1               5                  10                  15

Asn Leu Ser Glu Gly Ala Pro Arg Ser
            20                  25

<210> SEQ ID NO 617
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 617

Lys Thr Ala Thr Tyr Ile Thr Val Ile Asp Ile Thr Gly Arg Val Leu
 1               5                  10                  15

Met Pro Glu Met Gln Ile Asn Ser Asp Lys Tyr
            20                  25

<210> SEQ ID NO 618
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 618

Lys Ser Ile Asn Arg Ala Ala Gly Phe Ser Ser Phe Lys Phe Leu Pro
 1               5                  10                  15

Asp Ser Asp Asp Gln Ile Leu Leu Ala Leu Lys Thr
```

```
            20                  25

<210> SEQ ID NO 619
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 619

Arg Ala Ala Gly Phe Ser Ser Phe Lys Phe Leu Pro Asp Ser Asp Asp
 1               5                  10                  15

Gln Ile Leu Leu Ala Leu Lys Thr Ile Glu Lys Asp
            20                  25

<210> SEQ ID NO 620
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 620

Lys Thr Glu Glu Thr Ile Gly Cys Asn Lys Ile Ile Ile Ala Ser Glu
 1               5                  10                  15

Asn Phe Glu Ile Ile Lys Ser Ile Gln Ile Lys Gly
            20                  25

<210> SEQ ID NO 621
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 621

Lys Ile Pro Asn Gly Phe Ile Trp His Glu Ala Val Asn Trp Ser Lys
 1               5                  10                  15

Leu Lys Asn Gln Trp Val Phe Leu Pro Arg Lys
            20                  25

<210> SEQ ID NO 622
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 622

Arg Val Leu Met Pro Glu Met Gln Ile Asn Ser Asp Lys Tyr Glu Gly
 1               5                  10                  15

Ile Val Leu Leu Lys Ser Thr Glu Gly Phe Leu Lys Arg
            20                  25

<210> SEQ ID NO 623
<211> LENGTH: 30
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 623
```

```
Lys Asp Asp Lys Thr Ala Thr Tyr Ile Thr Val Ile Asp Ile Thr Gly
  1               5                  10                  15

Arg Val Leu Met Pro Glu Met Gln Ile Asn Ser Asp Lys Tyr
             20                  25                  30

<210> SEQ ID NO 624
<211> LENGTH: 32
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 624

Lys Thr Asn Ala Asp Leu Ile Pro Trp Val Thr Leu Ala Asn Gly Asn
  1               5                  10                  15

Gly Asp Gln Thr Asp Gly Phe Lys Ala Glu Trp Ala Thr Thr Lys Gly
             20                  25                  30

<210> SEQ ID NO 625
<211> LENGTH: 33
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 625

Lys Ser Gly Ile Val Phe Arg Leu Lys Thr Asn Ala Asp Leu Ile Pro
  1               5                  10                  15

Trp Val Thr Leu Ala Asn Gly Asn Gly Asp Gln Thr Asp Gly Phe Lys
             20                  25                  30

Ala

<210> SEQ ID NO 626
<211> LENGTH: 34
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 626

Arg Leu Lys Thr Asn Ala Asp Leu Ile Pro Trp Val Thr Leu Ala Asn
  1               5                  10                  15

Gly Asn Gly Asp Gln Thr Asp Gly Phe Lys Ala Glu Trp Ala Thr Thr
             20                  25                  30

Lys Gly

<210> SEQ ID NO 627
<211> LENGTH: 35
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 627

Lys Thr Asn Ala Asp Leu Ile Pro Trp Val Thr Leu Ala Asn Gly Asn
  1               5                  10                  15

Gly Asp Gln Thr Asp Gly Phe Lys Ala Glu Trp Ala Thr Thr Lys Gly
             20                  25                  30

Asp Lys Met
```

35

<210> SEQ ID NO 628
<211> LENGTH: 32
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 628

Lys Cys Ser Glu Arg Pro Phe Asp Thr Lys Thr Glu Glu Thr Ile Gly
1               5                   10                  15

Cys Asn Lys Ile Ile Ile Ala Ser Glu Asn Phe Glu Ile Ile Lys Ser
            20                  25                  30

<210> SEQ ID NO 629
<211> LENGTH: 35
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 629

Lys Thr Ala Thr Tyr Ile Thr Val Ile Asp Ile Thr Gly Arg Val Leu
1               5                   10                  15

Met Pro Glu Met Gln Ile Asn Ser Asp Lys Tyr Glu Gly Ile Val Leu
            20                  25                  30

Leu Lys Ser
        35

<210> SEQ ID NO 630
<211> LENGTH: 37
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 630

Lys Phe Cys Ile Val Ala Phe Ala Ile Cys Leu Ser Ile Asn Leu Ser
1               5                   10                  15

Glu Gly Ala Pro Arg Ser Gly Thr Ile Tyr Asn Phe Ala Ile Ile Ala
            20                  25                  30

Asp Leu Asp Lys Lys
        35

<210> SEQ ID NO 631
<211> LENGTH: 38
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 631

Lys Phe Cys Ile Val Ala Phe Ala Ile Cys Leu Ser Ile Asn Leu Ser
1               5                   10                  15

Glu Gly Ala Pro Arg Ser Gly Thr Ile Tyr Asn Phe Ala Ile Ile Ala
            20                  25                  30

Asp Leu Asp Lys Lys Ser
        35

```
<210> SEQ ID NO 632
<211> LENGTH: 39
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 632

Phe Leu Lys Phe Cys Ile Val Ala Phe Ala Ile Cys Leu Ser Ile Asn
 1               5                  10                  15

Leu Ser Glu Gly Ala Pro Arg Ser Gly Thr Ile Tyr Asn Phe Ala Ile
            20                  25                  30

Ile Ala Asp Leu Asp Lys Lys
        35

<210> SEQ ID NO 633
<211> LENGTH: 40
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 633

Met Phe Leu Lys Phe Cys Ile Val Ala Phe Ala Ile Cys Leu Ser Ile
 1               5                  10                  15

Asn Leu Ser Glu Gly Ala Pro Arg Ser Gly Thr Ile Tyr Asn Phe Ala
            20                  25                  30

Ile Ile Ala Asp Leu Asp Lys Lys
        35                  40

<210> SEQ ID NO 634
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 634

Lys Lys Lys Gly Ser Lys Leu
 1               5

<210> SEQ ID NO 635
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 635

Lys Leu Ile Gly Asp Arg Gly
 1               5

<210> SEQ ID NO 636
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 636

Arg Leu Met Lys Val Lys Thr
 1               5
```

<210> SEQ ID NO 637
<211> LENGTH: 7
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 637

Lys Thr Tyr Pro Ile Lys Lys
1               5

<210> SEQ ID NO 638
<211> LENGTH: 7
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 638

Lys Leu Leu Lys Lys Lys Gly
1               5

<210> SEQ ID NO 639
<211> LENGTH: 7
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 639

Lys Val Lys Thr Lys Arg Ala
1               5

<210> SEQ ID NO 640
<211> LENGTH: 7
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 640

Arg Leu Met Lys Val Lys Thr
1               5

<210> SEQ ID NO 641
<211> LENGTH: 8
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 641

Arg Ala Ile Lys Gly Glu Lys Cys
1               5

<210> SEQ ID NO 642
<211> LENGTH: 8
<212> TYPE: PRT
<213> ORGANISM: Artificial Sequence
<220> FEATURE:
<223> OTHER INFORMATION: Description of Artificial Sequence; NOTE = Synthetic Construct

```
<400> SEQUENCE: 642

Lys Phe Ser Gly Lys Ser Lys Gln
  1               5

<210> SEQ ID NO 643
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 643

Lys Arg Cys Ser Asp Lys Asn
  1               5

<210> SEQ ID NO 644
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 644

Lys Glu His Lys Phe Lys Ala
  1               5

<210> SEQ ID NO 645
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 645

Lys Gly Glu Lys Cys Gln Gly
  1               5

<210> SEQ ID NO 646
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 646

Lys Thr Lys Arg Ala Ile Lys Gly
  1               5

<210> SEQ ID NO 647
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 647

Arg Lys Thr Tyr Pro Ile Lys Lys
  1               5

<210> SEQ ID NO 648
<211> LENGTH: 9
<212> TYPE: PRT
<213> ORGANISM: Artificial Sequence
```

```
<220> FEATURE:
<223> OTHER INFORMATION: Description of Artificial Sequence; NOTE =
      Synthetic Construct

<400> SEQUENCE: 648

Lys Gly Ser Lys Leu Glu Pro Lys Leu
 1               5

<210> SEQ ID NO 649
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 649

Lys Gly Glu Ala Trp Ser Leu Lys Asp
 1               5

<210> SEQ ID NO 650
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 650

Lys Arg Ala Ile Lys Gly Glu Lys Cys
 1               5

<210> SEQ ID NO 651
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 651

Arg Leu Asp Thr Lys Leu Leu Lys Lys
 1               5

<210> SEQ ID NO 652
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 652

Arg Leu Met Lys Val Lys Thr Lys Arg
 1               5

<210> SEQ ID NO 653
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 653

Lys Lys Gly Ser Lys Leu Glu Pro Lys Leu
 1               5                   10
```

```
<210> SEQ ID NO 654
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 654

Arg Cys Ser Asp Lys Asn Glu Lys Thr
 1               5

<210> SEQ ID NO 655
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 655

Lys Leu Ile Gly Asp Arg Gly Phe Lys Thr
 1               5                  10

<210> SEQ ID NO 656
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 656

Lys Leu Tyr Arg Leu Asp Thr Lys Leu
 1               5

<210> SEQ ID NO 657
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 657

Lys Lys Gly Glu Ala Trp Ser Leu Lys Asp
 1               5                  10

<210> SEQ ID NO 658
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 658

Arg Leu Asp Thr Lys Leu Leu Lys Lys Lys
 1               5                  10

<210> SEQ ID NO 659
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 659
```

```
Arg Tyr Glu Leu Thr Gly Glu Ala Gly Lys Asn
1               5                   10
```

<210> SEQ ID NO 660
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 660

```
Lys Met Leu Phe Phe Gly Ile Pro Arg Ile
1               5                   10
```

<210> SEQ ID NO 661
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 661

```
Arg Ala Ile Lys Gly Glu Lys Cys Gln Gly
1               5                   10
```

<210> SEQ ID NO 662
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 662

```
Lys Ser Asn Tyr Pro Glu Ile His Arg Tyr
1               5                   10
```

<210> SEQ ID NO 663
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 663

```
Arg Ala Tyr Glu Trp Ser Glu Ile Lys Leu
1               5                   10
```

<210> SEQ ID NO 664
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 664

```
Arg Gln Val Ser Cys Trp Asn Ile Lys His
1               5                   10
```

<210> SEQ ID NO 665
<211> LENGTH: 11
<212> TYPE: PRT
<213> ORGANISM: Artificial Sequence
<220> FEATURE:
<223> OTHER INFORMATION: Description of Artificial Sequence; NOTE =

Synthetic Construct

<400> SEQUENCE: 665

Lys Leu Glu Pro Lys Leu Ile Gly Asp Arg Gly
1               5                   10

<210> SEQ ID NO 666
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 666

Lys Lys Lys Gly Glu Ala Trp Ser Leu Lys Asp
1               5                   10

<210> SEQ ID NO 667
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 667

Arg Gln Val Ser Cys Trp Asn Ile Lys His
1               5                   10

<210> SEQ ID NO 668
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 668

Lys Arg Cys Ser Asp Lys Asn Glu Lys Thr
1               5                   10

<210> SEQ ID NO 669
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 669

Lys Ala Gly Ile Phe Gly Ile Ala Leu Gly Asp Arg Asn
1               5                   10

<210> SEQ ID NO 670
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 670

Lys Met Glu Tyr Asp Val Pro Gln Ile Arg Leu
1               5                   10

<210> SEQ ID NO 671
<211> LENGTH: 12

<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 671

Lys Val Leu Phe Phe Ala Glu Ala Asp Ser Arg Gln
1               5                   10

<210> SEQ ID NO 672
<211> LENGTH: 13
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 672

Arg Val Pro Ile Thr Phe Ala Gln Leu Ser Thr Arg Ser
1               5                   10

<210> SEQ ID NO 673
<211> LENGTH: 13
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 673

Lys Lys Pro Ser Leu Ile Ala Phe Asp Leu Thr Lys Ser
1               5                   10

<210> SEQ ID NO 674
<211> LENGTH: 12
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 674

Lys Leu Tyr Arg Leu Asp Thr Lys Leu Leu Lys Lys
1               5                   10

<210> SEQ ID NO 675
<211> LENGTH: 14
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 675

Lys Gly Ser Lys Leu Glu Pro Lys Leu Ile Gly Asp Arg Gly
1               5                   10

<210> SEQ ID NO 676
<211> LENGTH: 15
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 676

Lys Ala Gly Ile Phe Gly Ile Ala Leu Gly Asp Arg Asn Lys Glu
1               5                   10                  15

```
<210> SEQ ID NO 677
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 677

Lys Phe Lys Ala Gly Ile Phe Gly Ile Ala Leu Gly Asp Arg Asn
1               5                   10                  15

<210> SEQ ID NO 678
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 678

Lys Leu Glu Pro Lys Leu Ile Gly Asp Arg Gly Phe Lys Thr
1               5                   10

<210> SEQ ID NO 679
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 679

Lys Thr Glu Ala Ile Ala Leu Ala Tyr Asp Pro Glu Thr Lys Val
1               5                   10                  15

<210> SEQ ID NO 680
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 680

Lys Met Leu Phe Phe Gly Ile Pro Arg Ile Tyr Ser Arg Val
1               5                   10

<210> SEQ ID NO 681
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 681

Lys Met Glu Tyr Asp Val Pro Gln Ile Arg Leu Met Lys Val
1               5                   10

<210> SEQ ID NO 682
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct
```

-continued

```
<400> SEQUENCE: 682

Arg Ser Tyr Asn Ser Ala Glu Ile Pro Asn Pro Pro Leu Asp Lys Phe
1               5                   10                  15

<210> SEQ ID NO 683
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 683

Lys Phe Lys Ala Gly Ile Phe Gly Ile Ala Leu Gly Asp Arg Asn Lys
1               5                   10                  15

Glu

<210> SEQ ID NO 684
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 684

Lys Glu Gly Asn Arg Pro Ala Tyr Tyr Leu Ala Gly Ser Ser Thr Lys
1               5                   10                  15

Leu

<210> SEQ ID NO 685
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 685

Lys Asn Pro Leu Gly Tyr Gly Gly Phe Ala Val Asp Val Val Asn Pro
1               5                   10                  15

Lys Arg

<210> SEQ ID NO 686
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 686

Arg Leu Trp Val Leu Asp Val Gly Ile Val Glu Asn Glu Ala Glu Arg
1               5                   10                  15

Lys

<210> SEQ ID NO 687
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 687
```

Lys Met Glu Tyr Asp Val Pro Gln Ile Arg Leu Met Lys Val Lys Thr
1               5                   10                  15

<210> SEQ ID NO 688
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 688

Arg Ile Tyr Ser Arg Val Pro Ile Thr Phe Ala Gln Leu Ser Thr Arg
1               5                   10                  15

Ser

<210> SEQ ID NO 689
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 689

Arg Gly Phe Lys Thr Glu Ala Ile Ala Leu Ala Tyr Asp Pro Glu Thr
1               5                   10                  15

Lys Val

<210> SEQ ID NO 690
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 690

Lys Glu His Lys Phe Lys Ala Gly Ile Phe Gly Ile Ala Leu Gly Asp
1               5                   10                  15

Arg Asn

<210> SEQ ID NO 691
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 691

Lys Gln Pro Leu Thr Ser Val Tyr Gln Pro Val Ile Asp Asp Cys Arg
1               5                   10                  15

Arg

<210> SEQ ID NO 692
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 692

Lys Asn Pro Leu Gly Tyr Gly Gly Phe Ala Val Asp Val Val Asn Pro
1               5                   10                  15

Lys Arg Cys

<210> SEQ ID NO 693
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 693

Lys Thr Tyr Pro Ile Lys Lys Pro Ser Leu Ile Ala Phe Asp Leu Thr
1               5                   10                  15

Lys Ser

<210> SEQ ID NO 694
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 694

Lys Asp Asp Ser Phe Lys Pro Glu Gly Val Thr Thr Phe Thr Leu Asn
1               5                   10                  15

Gly Lys Glu

<210> SEQ ID NO 695
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 695

Arg Asn Lys Glu Gly Asn Arg Pro Ala Tyr Tyr Leu Ala Gly Ser Ser
1               5                   10                  15

Thr Lys Leu

<210> SEQ ID NO 696
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 696

Lys Gly Phe Leu Trp Phe Met Ser Asn Gly Gln Pro Pro Ile Asp Glu
1               5                   10                  15

Lys Met

<210> SEQ ID NO 697
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 697

Arg Leu Trp Val Leu Asp Val Gly Ile Val Glu Asn Glu Ala Glu Arg
1               5                   10                  15

Lys Thr

<210> SEQ ID NO 698
<211> LENGTH: 18
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 698

Lys Gly Phe Leu Trp Phe Met Ser Asn Gly Gln Pro Pro Ile Asp Glu
 1               5                  10                  15

Lys Met

<210> SEQ ID NO 699
<211> LENGTH: 18
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 699

Arg Arg Leu Trp Val Leu Asp Val Gly Ile Val Glu Asn Glu Ala Glu
 1               5                  10                  15

Arg Lys

<210> SEQ ID NO 700
<211> LENGTH: 18
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 700

Lys Gln Pro Leu Thr Ser Val Tyr Gln Pro Val Ile Asp Asp Cys Arg
 1               5                  10                  15

Arg Leu

<210> SEQ ID NO 701
<211> LENGTH: 19
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 701

Arg Lys Thr Tyr Pro Ile Lys Lys Pro Ser Leu Ile Ala Phe Asp Leu
 1               5                  10                  15

Thr Lys Ser

<210> SEQ ID NO 702
<211> LENGTH: 19
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 702

Lys Ser Asn Tyr Pro Glu Ile His Arg Tyr Glu Leu Thr Gly Glu Ala
 1               5                  10                  15

Gly Lys Asn

<210> SEQ ID NO 703
<211> LENGTH: 20
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 703

Arg Ser Tyr Asn Ser Ala Glu Ile Pro Asn Pro Pro Leu Asp Lys Phe
1               5                   10                  15

Ser Gly Lys Ser
            20

<210> SEQ ID NO 704
<211> LENGTH: 19
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 704

Lys Ser Lys Gln Pro Leu Thr Ser Val Tyr Gln Pro Val Ile Asp Asp
1               5                   10                  15

Cys Arg Arg

<210> SEQ ID NO 705
<211> LENGTH: 19
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 705

Arg Arg Leu Trp Val Leu Asp Val Gly Ile Val Glu Asn Glu Ala Glu
1               5                   10                  15

Arg Lys Thr

<210> SEQ ID NO 706
<211> LENGTH: 20
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 706

Lys Glu Gly Asn Arg Pro Ala Tyr Tyr Leu Ala Gly Ser Ser Thr Lys
1               5                   10                  15

Leu Tyr Arg Leu
20

<210> SEQ ID NO 707
<211> LENGTH: 20
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 707

```
Lys Ser Lys Gln Pro Leu Thr Ser Val Tyr Gln Pro Val Ile Asp Asp
1               5                   10                  15

Cys Arg Arg Leu
            20

<210> SEQ ID NO 708
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 708

Arg Ser Tyr Asn Ser Ala Glu Ile Pro Asn Pro Pro Leu Asp Lys Phe
1               5                   10                  15

Ser Gly Lys Ser Lys Gln
            20

<210> SEQ ID NO 709
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 709

Lys Thr Tyr Ile Tyr Ile Ala Asn Phe Asp Glu Asn Ser Leu Ile Val
1               5                   10                  15

Tyr Asp Lys Lys
            20

<210> SEQ ID NO 710
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 710

Lys Val Leu Phe Phe Ala Glu Ala Asp Ser Arg Gln Val Ser Cys Trp
1               5                   10                  15

Asn Ile Lys His
            20

<210> SEQ ID NO 711
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 711

Lys Lys Pro Ser Leu Ile Ala Phe Asp Leu Thr Lys Ser Asn Tyr Pro
1               5                   10                  15

Glu Ile His Arg Tyr
            20

<210> SEQ ID NO 712
<211> LENGTH: 22
<212> TYPE: PRT
<213> ORGANISM: Artificial Sequence
<220> FEATURE:
```

-continued

```
<223> OTHER INFORMATION: Description of Artificial Sequence; NOTE =
      Synthetic Construct

<400> SEQUENCE: 712

Lys Asp Asp Ser Phe Lys Pro Glu Gly Val Thr Thr Phe Thr Leu Asn
1               5                   10                  15

Gly Lys Glu His Lys Phe
            20

<210> SEQ ID NO 713
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 713

Arg Asn Lys Glu Gly Asn Arg Pro Ala Tyr Tyr Leu Ala Gly Ser Ser
1               5                   10                  15

Thr Lys Leu Tyr Arg Leu
            20

<210> SEQ ID NO 714
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 714

Lys Asn Pro Leu Gly Tyr Gly Gly Phe Ala Val Asp Val Val Asn Pro
1               5                   10                  15

Lys Arg Cys Ser Asp Lys Asn
            20

<210> SEQ ID NO 715
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 715

Lys Leu Ile Gly Asp Arg Gly Phe Lys Thr Glu Ala Ile Ala Leu Ala
1               5                   10                  15

Tyr Asp Pro Glu Thr Lys Val
            20

<210> SEQ ID NO 716
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 716

Lys Thr Tyr Ile Tyr Ile Ala Asn Phe Asp Glu Asn Ser Leu Ile Val
1               5                   10                  15

Tyr Asp Lys Lys Lys
            20
```

<210> SEQ ID NO 717
<211> LENGTH: 23
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 717

Lys Leu Ile Leu Cys Val Leu Ser Phe Leu Ser Leu Gln Val Ala Leu
1               5                   10                  15

Ser Asp Asp Val Gly Arg Ala
            20

<210> SEQ ID NO 718
<211> LENGTH: 22
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 718

Lys Thr Tyr Ile Tyr Ile Ala Asn Phe Asp Glu Asn Ser Leu Ile Val
1               5                   10                  15

Tyr Asp Lys Lys Lys Gly
            20

<210> SEQ ID NO 719
<211> LENGTH: 23
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 719

Lys Phe Ser Gly Lys Ser Lys Gln Pro Leu Thr Ser Val Tyr Gln Pro
1               5                   10                  15

Val Ile Asp Asp Cys Arg Arg
            20

<210> SEQ ID NO 720
<211> LENGTH: 23
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 720

Arg Leu Trp Val Leu Asp Val Gly Ile Val Glu Asn Glu Ala Glu Arg
1               5                   10                  15

Lys Thr Tyr Pro Ile Lys Lys
            20

<210> SEQ ID NO 721
<211> LENGTH: 24
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 721

Lys Glu Gly Asn Arg Pro Ala Tyr Tyr Leu Ala Gly Ser Ser Thr Lys
1               5                   10                  15

Leu Tyr Arg Leu Asp Thr Lys Leu
            20

<210> SEQ ID NO 722
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 722

Lys Asp Asp Ser Phe Lys Pro Glu Gly Val Thr Thr Phe Thr Leu Asn
1               5                   10                  15

Gly Lys Glu His Lys Phe Lys Ala
            20

<210> SEQ ID NO 723
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 723

Lys Asn Glu Lys Thr Tyr Ile Tyr Ile Ala Asn Phe Asp Glu Asn Ser
1               5                   10                  15

Leu Ile Val Tyr Asp Lys Lys
            20

<210> SEQ ID NO 724
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 724

Lys Thr Glu Ala Ile Ala Leu Ala Tyr Asp Pro Glu Thr Lys Val Leu
1               5                   10                  15

Phe Phe Ala Glu Ala Asp Ser Arg Gln
            20                  25

<210> SEQ ID NO 725
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 725

Met Lys Leu Ile Leu Cys Val Leu Ser Phe Leu Ser Leu Gln Val Ala
1               5                   10                  15

Leu Ser Asp Asp Val Gly Arg Ala
            20

<210> SEQ ID NO 726
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

```
<400> SEQUENCE: 726

Arg Tyr Glu Leu Thr Gly Glu Ala Gly Lys Asn Pro Leu Gly Tyr Gly
 1               5                  10                  15
Gly Phe Ala Val Asp Val Val Asn Pro Lys Arg
             20                  25

<210> SEQ ID NO 727
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 727

Lys Gly Glu Ala Trp Ser Leu Lys Asp Asp Ser Phe Lys Pro Glu Gly
 1               5                  10                  15
Val Thr Thr Phe Thr Leu Asn Gly Lys Glu
             20                  25

<210> SEQ ID NO 728
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 728

Lys Leu Val Gly Val Arg Pro Asn Ala Tyr Asp Ser Gly Asn Ile Val
 1               5                  10                  15
Pro Thr Gly Val Ala Tyr Asp Ala Ala Ser Lys Met
             20                  25

<210> SEQ ID NO 729
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 729

Lys Asn Glu Lys Thr Tyr Ile Tyr Ile Ala Asn Phe Asp Glu Asn Ser
 1               5                  10                  15
Leu Ile Val Tyr Asp Lys Lys Lys
             20

<210> SEQ ID NO 730
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 730

Lys Met Leu Phe Phe Gly Ile Pro Arg Ile Tyr Ser Arg Val Pro Ile
 1               5                  10                  15
Thr Phe Ala Gln Leu Ser Thr Arg Ser
             20                  25

<210> SEQ ID NO 731
<211> LENGTH: 28
```

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 731

Arg Tyr Glu Leu Thr Gly Glu Ala Gly Lys Asn Pro Leu Gly Tyr Gly
1               5                   10                  15

Gly Phe Ala Val Asp Val Val Asn Pro Lys Arg Cys
            20                  25

<210> SEQ ID NO 732
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 732

Lys Lys Gly Glu Ala Trp Ser Leu Lys Asp Asp Ser Phe Lys Pro Glu
1               5                   10                  15

Gly Val Thr Thr Phe Thr Leu Asn Gly Lys Glu
            20                  25

<210> SEQ ID NO 733
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 733

Arg Val Pro Ile Thr Phe Ala Gln Leu Ser Thr Arg Ser Tyr Asn Ser
1               5                   10                  15

Ala Glu Ile Pro Asn Pro Pro Leu Asp Lys Phe
            20                  25

<210> SEQ ID NO 734
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 734

Lys Thr Tyr Pro Ile Lys Lys Pro Ser Leu Ile Ala Phe Asp Leu Thr
1               5                   10                  15

Lys Ser Asn Tyr Pro Glu Ile His Arg Tyr
            20                  25

<210> SEQ ID NO 735
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 735

Arg Gly Phe Lys Thr Glu Ala Ile Ala Leu Ala Tyr Asp Pro Glu Thr
1               5                   10                  15

Lys Val Leu Phe Phe Ala Glu Ala Asp Ser Arg Gln
```

20              25

<210> SEQ ID NO 736
<211> LENGTH: 30
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 736

Lys Ala Gly Ile Phe Gly Ile Ala Leu Gly Asp Arg Asn Lys Glu Gly
1               5                   10                  15

Asn Arg Pro Ala Tyr Tyr Leu Ala Gly Ser Ser Thr Lys Leu
            20                  25                  30

<210> SEQ ID NO 737
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 737

Lys Gly Phe Leu Trp Phe Met Ser Asn Gly Gln Pro Pro Ile Asp Glu
1               5                   10                  15

Lys Met Glu Tyr Asp Val Pro Gln Ile Arg Leu
            20                  25

<210> SEQ ID NO 738
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 738

Lys Gly Glu Ala Trp Ser Leu Lys Asp Asp Ser Phe Lys Pro Glu Gly
1               5                   10                  15

Val Thr Thr Phe Thr Leu Asn Gly Lys Glu His Lys Phe
            20                  25

<210> SEQ ID NO 739
<211> LENGTH: 27
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 739

Arg Cys Ser Asp Lys Asn Glu Lys Thr Tyr Ile Tyr Ile Ala Asn Phe
1               5                   10                  15

Asp Glu Asn Ser Leu Ile Val Tyr Asp Lys Lys
            20                  25

<210> SEQ ID NO 740
<211> LENGTH: 30
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 740

Lys His Glu Leu Lys Pro Glu Asn Val Gly Val Ile Tyr Ala Asn Pro
1               5                   10                  15

Asn Phe Asn Phe Gly Thr Asp Ile Met Val Asp Ser Lys Gly
            20                  25                  30

<210> SEQ ID NO 741
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 741

Arg Val Pro Ile Thr Phe Ala Gln Leu Ser Thr Arg Ser Tyr Asn Ser
1               5                   10                  15

Ala Glu Ile Pro Asn Pro Pro Leu Asp Lys Phe Ser Gly Lys Ser
            20                  25                  30

<210> SEQ ID NO 742
<211> LENGTH: 30
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 742

Lys Lys Pro Ser Leu Ile Ala Phe Asp Leu Thr Lys Ser Asn Tyr Pro
1               5                   10                  15

Glu Ile His Arg Tyr Glu Leu Thr Gly Glu Ala Gly Lys Asn
            20                  25                  30

<210> SEQ ID NO 743
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 743

Arg Ile Tyr Ser Arg Val Pro Ile Thr Phe Ala Gln Leu Ser Thr Arg
1               5                   10                  15

Ser Tyr Asn Ser Ala Glu Ile Pro Asn Pro Pro Leu Asp Lys Phe
            20                  25                  30

<210> SEQ ID NO 744
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 744

Lys Leu Ile Leu Cys Val Leu Ser Phe Leu Ser Leu Gln Val Ala Leu
1               5                   10                  15

Ser Asp Asp Val Gly Arg Ala Tyr Glu Trp Ser Glu Ile Lys Leu
            20                  25                  30

<210> SEQ ID NO 745
<211> LENGTH: 30
<212> TYPE: PRT
<213> ORGANISM: Artificial Sequence

```
<220> FEATURE:
<223> OTHER INFORMATION: Description of Artificial Sequence; NOTE =
      Synthetic Construct

<400> SEQUENCE: 745

Lys Gly Phe Leu Trp Phe Met Ser Asn Gly Gln Pro Pro Ile Asp Glu
1               5                   10                  15

Lys Met Glu Tyr Asp Val Pro Gln Ile Arg Leu Met Lys Val
            20                  25                  30

<210> SEQ ID NO 746
<211> LENGTH: 33
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 746

Lys Thr Glu Ala Ile Ala Leu Ala Tyr Asp Pro Glu Thr Lys Val Leu
1               5                   10                  15

Phe Phe Ala Glu Ala Asp Ser Arg Gln Val Ser Cys Trp Asn Ile Lys
            20                  25                  30

His

<210> SEQ ID NO 747
<211> LENGTH: 35
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 747

Lys Ser Asn Tyr Pro Glu Ile His Arg Tyr Glu Leu Thr Gly Glu Ala
1               5                   10                  15

Gly Lys Asn Pro Leu Gly Tyr Gly Gly Phe Ala Val Asp Val Val Asn
            20                  25                  30

Pro Lys Arg
        35

<210> SEQ ID NO 748
<211> LENGTH: 36
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 748

Lys Leu Val Gly Val Arg Pro Asn Ala Tyr Asp Ser Gly Asn Ile Val
1               5                   10                  15

Pro Thr Gly Val Ala Tyr Asp Ala Ala Ser Lys Met Leu Phe Phe Gly
            20                  25                  30

Ile Pro Arg Ile
        35

<210> SEQ ID NO 749
<211> LENGTH: 32
<212> TYPE: PRT
<213> ORGANISM: Artificial Sequence
<220> FEATURE:
<223> OTHER INFORMATION: Description of Artificial Sequence; NOTE =
      Synthetic Construct
```

-continued

```
<400> SEQUENCE: 749

Met Lys Leu Ile Leu Cys Val Leu Ser Phe Leu Ser Leu Gln Val Ala
1               5                   10                  15

Leu Ser Asp Asp Val Gly Arg Ala Tyr Glu Trp Ser Glu Ile Lys Leu
            20                  25                  30

<210> SEQ ID NO 750
<211> LENGTH: 36
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 750

Arg Ala Tyr Glu Trp Ser Glu Ile Lys Leu Val Gly Val Arg Pro Asn
1               5                   10                  15

Ala Tyr Asp Ser Gly Asn Ile Val Pro Thr Gly Val Ala Tyr Asp Ala
            20                  25                  30

Ala Ser Lys Met
        35

<210> SEQ ID NO 751
<211> LENGTH: 33
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 751

Lys Gln Pro Leu Thr Ser Val Tyr Gln Pro Val Ile Asp Asp Cys Arg
1               5                   10                  15

Arg Leu Trp Val Leu Asp Val Gly Ile Val Glu Asn Glu Ala Glu Arg
            20                  25                  30

Lys

<210> SEQ ID NO 752
<211> LENGTH: 40
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 752

Lys Leu Val Gly Val Arg Pro Asn Ala Tyr Asp Ser Gly Asn Ile Val
1               5                   10                  15

Pro Thr Gly Val Ala Tyr Asp Ala Ala Ser Lys Met Leu Phe Phe Gly
            20                  25                  30

Ile Pro Arg Ile Tyr Ser Arg Val
        35                  40

<210> SEQ ID NO 753
<211> LENGTH: 38
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 753

Arg Gln Val Ser Cys Trp Asn Ile Lys His Glu Leu Lys Pro Glu Asn
1               5                   10                  15
```

```
Val Gly Val Ile Tyr Ala Asn Pro Asn Phe Asn Phe Gly Thr Asp Ile
            20                  25                  30

Met Val Asp Ser Lys Gly
            35

<210> SEQ ID NO 754
<211> LENGTH: 44
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 754

Arg Ala Tyr Glu Trp Ser Glu Ile Lys Leu Val Gly Val Arg Pro Asn
1               5                   10                  15

Ala Tyr Asp Ser Gly Asn Ile Val Pro Thr Gly Val Ala Tyr Asp Ala
            20                  25                  30

Ala Ser Lys Met Leu Phe Phe Gly Ile Pro Arg Ile
            35                  40

<210> SEQ ID NO 755
<211> LENGTH: 46
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 755

Lys His Glu Leu Lys Pro Glu Asn Val Gly Val Ile Tyr Ala Asn Pro
1               5                   10                  15

Asn Phe Asn Phe Gly Thr Asp Ile Met Val Asp Ser Lys Gly Phe Leu
            20                  25                  30

Trp Phe Met Ser Asn Gly Gln Pro Pro Ile Asp Glu Lys Met
            35                  40                  45

<210> SEQ ID NO 756
<211> LENGTH: 48
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 756

Lys Val Leu Phe Phe Ala Glu Ala Asp Ser Arg Gln Val Ser Cys Trp
1               5                   10                  15

Asn Ile Lys His Glu Leu Lys Pro Glu Asn Val Gly Val Ile Tyr Ala
            20                  25                  30

Asn Pro Asn Phe Asn Phe Gly Thr Asp Ile Met Val Asp Ser Lys Gly
            35                  40                  45

<210> SEQ ID NO 757
<211> LENGTH: 57
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 757

Lys Leu Ile Leu Cys Val Leu Ser Phe Leu Ser Leu Gln Val Ala Leu
1               5                   10                  15
```

```
Ser Asp Asp Val Gly Arg Ala Tyr Glu Trp Ser Glu Ile Lys Leu Val
            20                  25                  30

Gly Val Arg Pro Asn Ala Tyr Asp Ser Gly Asn Ile Val Pro Thr Gly
        35                  40                  45

Val Ala Tyr Asp Ala Ala Ser Lys Met
    50                  55

<210> SEQ ID NO 758
<211> LENGTH: 54
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 758

Arg Gln Val Ser Cys Trp Asn Ile Lys His Glu Leu Lys Pro Glu Asn
 1               5                  10                  15

Val Gly Val Ile Tyr Ala Asn Pro Asn Phe Asn Phe Gly Thr Asp Ile
            20                  25                  30

Met Val Asp Ser Lys Gly Phe Leu Trp Phe Met Ser Asn Gly Gln Pro
        35                  40                  45

Pro Ile Asp Glu Lys Met
    50

<210> SEQ ID NO 759
<211> LENGTH: 55
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 759

Lys His Glu Leu Lys Pro Glu Asn Val Gly Val Ile Tyr Ala Asn Pro
 1               5                  10                  15

Asn Phe Asn Phe Gly Thr Asp Ile Met Val Asp Ser Lys Gly Phe Leu
            20                  25                  30

Trp Phe Met Ser Asn Gly Gln Pro Pro Ile Asp Glu Lys Met Glu Tyr
        35                  40                  45

Asp Val Pro Gln Ile Arg Leu
    50                  55

<210> SEQ ID NO 760
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 760

Arg Leu Leu Gly Glu Arg Gly
 1               5

<210> SEQ ID NO 761
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 761
```

```
Lys Glu Leu Ile Pro Lys Asn
1               5

<210> SEQ ID NO 762
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 762

Lys Leu Asp Phe Asp Lys Arg
1               5

<210> SEQ ID NO 763
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 763

Arg Ser Pro Pro Phe Ser Lys Phe
1               5

<210> SEQ ID NO 764
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 764

Lys Gly Ala Ser Leu Lys Pro Arg Leu
1               5

<210> SEQ ID NO 765
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 765

Lys Ser Val Phe Asn His Lys Gly
1               5

<210> SEQ ID NO 766
<211> LENGTH: 7
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 766

Arg Phe Tyr Ala Trp Arg Asn
1               5

<210> SEQ ID NO 767
<211> LENGTH: 9
<212> TYPE: PRT
<213> ORGANISM: Artificial Sequence
<220> FEATURE:
```

```
<223> OTHER INFORMATION: Description of Artificial Sequence; NOTE =
      Synthetic Construct

<400> SEQUENCE: 767

Lys Leu Glu Gly Asp Val Ala Arg Ser
 1               5

<210> SEQ ID NO 768
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 768

Lys Asn Lys Asn Ala Trp Lys Phe
 1               5

<210> SEQ ID NO 769
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 769

Lys Phe Asn Ser Gln Ser Gly Lys Glu
 1               5

<210> SEQ ID NO 770
<211> LENGTH: 8
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 770

Lys Leu Asp Phe Asp Lys Arg Gln
 1               5

<210> SEQ ID NO 771
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 771

Lys Leu Tyr Phe Gly Val Pro Arg Arg
 1               5

<210> SEQ ID NO 772
<211> LENGTH: 9
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 772

Arg Asn Leu Pro Cys Glu Val Arg Lys
 1               5

<210> SEQ ID NO 773
```

```
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 773

Arg Leu Leu Gly Glu Arg Gly Phe Lys Thr
1               5                   10

<210> SEQ ID NO 774
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 774

Lys His Gly Asn Glu Tyr Pro Thr Lys Asn
1               5                   10

<210> SEQ ID NO 775
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 775

Arg Asn Ile Thr Phe Glu Asp Val Lys Glu
1               5                   10

<210> SEQ ID NO 776
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 776

Lys Lys Leu Tyr Phe Gly Val Pro Arg Arg
1               5                   10

<210> SEQ ID NO 777
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 777

Lys Glu Lys Gly Ala Ser Leu Lys Pro Arg Leu
1               5                   10

<210> SEQ ID NO 778
<211> LENGTH: 10
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 778

Lys Leu Tyr Phe Gly Val Pro Arg Arg Tyr
```

<210> SEQ ID NO 779
<211> LENGTH: 10
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 779

Arg Leu Met Tyr Val Pro Thr His Arg Ala
1               5                   10

<210> SEQ ID NO 780
<211> LENGTH: 11
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 780

Arg Tyr Lys Leu Glu Gly Asp Val Ala Arg Ser
1               5                   10

<210> SEQ ID NO 781
<211> LENGTH: 10
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 781

Arg Asn Tyr Asn Arg Ser Glu Ile Arg Ser
1               5                   10

<210> SEQ ID NO 782
<211> LENGTH: 11
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 782

Arg Gln Val Ser Ala Trp Asn Ile Gln Lys Glu
1               5                   10

<210> SEQ ID NO 783
<211> LENGTH: 11
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 783

Lys Lys His Gly Asn Glu Tyr Pro Thr Lys Asn
1               5                   10

<210> SEQ ID NO 784
<211> LENGTH: 12
<212> TYPE: PRT
<213> ORGANISM: Artificial Sequence
<220> FEATURE:
<223> OTHER INFORMATION: Description of Artificial Sequence; NOTE = Synthetic Construct

```
<400> SEQUENCE: 784

Lys Val Tyr Ser Val Asn Thr Ala Ser Leu Lys Glu
1               5                   10

<210> SEQ ID NO 785
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 785

Lys Lys Leu Tyr Phe Gly Val Pro Arg Arg Tyr
1               5                   10

<210> SEQ ID NO 786
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 786

Arg Ser Glu Ile Arg Ser Pro Pro Phe Ser Lys Phe
1               5                   10

<210> SEQ ID NO 787
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 787

Lys Leu Asp Phe Asp Lys Arg Gln Ile Arg Leu
1               5                   10

<210> SEQ ID NO 788
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 788

Lys Thr Glu Ala Ile Ala Leu Ala Tyr Asp Pro Lys Thr
1               5                   10

<210> SEQ ID NO 789
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 789

Lys Val Ile Phe Phe Val Glu Ser Asp Ser Arg Gln
1               5                   10

<210> SEQ ID NO 790
<211> LENGTH: 12
<212> TYPE: PRT
```

```
<213> ORGANISM: Artificial Sequence
<220> FEATURE:
<223> OTHER INFORMATION: Description of Artificial Sequence; NOTE =
      Synthetic Construct

<400> SEQUENCE: 790

Lys Thr Lys Lys Leu Tyr Phe Gly Val Pro Arg Arg
1               5                   10

<210> SEQ ID NO 791
<211> LENGTH: 12
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 791

Arg Ala Ile Arg Asn Leu Pro Cys Glu Val Arg Lys
1               5                   10

<210> SEQ ID NO 792
<211> LENGTH: 11
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 792

Arg Asn Leu Pro Cys Glu Val Arg Lys Pro Lys
1               5                   10

<210> SEQ ID NO 793
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 793

Lys Gly Ala Ser Leu Lys Pro Arg Leu Leu Gly Glu Arg Gly
1               5                   10

<210> SEQ ID NO 794
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 794

Lys Val Tyr Ser Val Asn Thr Ala Ser Leu Lys Glu Lys Gly
1               5                   10

<210> SEQ ID NO 795
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 795

Arg Leu Met Tyr Val Pro Thr His Arg Ala Ile Arg Asn
1               5                   10
```

<210> SEQ ID NO 796
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 796

Lys Phe Asn Asp Asp Ser Phe Lys Pro Glu Pro Gly Lys Ser
 1               5                  10

<210> SEQ ID NO 797
<211> LENGTH: 13
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 797

Arg Gln Ile Arg Leu Met Tyr Val Pro Thr His Arg Ala
 1               5                  10

<210> SEQ ID NO 798
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 798

Arg Ser Pro Pro Phe Ser Lys Phe Asn Ser Gln Ser Gly Lys Glu
 1               5                  10                  15

<210> SEQ ID NO 799
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 799

Lys Thr Glu Ala Ile Ala Leu Ala Tyr Asp Pro Lys Thr Lys Val
 1               5                  10                  15

<210> SEQ ID NO 800
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 800

Lys Thr Lys Val Ile Phe Phe Val Glu Ser Asp Ser Arg Gln
 1               5                  10

<210> SEQ ID NO 801
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 801

```
Arg Leu Trp Val Leu Asp Val Gly Gln Val Asp Tyr Lys Lys
1               5                   10
```

<210> SEQ ID NO 802
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 802

```
Arg Gly Phe Lys Thr Glu Ala Ile Ala Leu Ala Tyr Asp Pro Lys Thr
1               5                   10                  15
```

<210> SEQ ID NO 803
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 803

```
Lys Glu Lys Gly Ala Ser Leu Lys Pro Arg Leu Leu Gly Glu Arg Gly
1               5                   10                  15
```

<210> SEQ ID NO 804
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 804

```
Arg Leu Trp Val Leu Asp Val Gly Gln Val Asp Tyr Lys Lys His
1               5                   10                  15
```

<210> SEQ ID NO 805
<211> LENGTH: 14
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 805

```
Lys Arg Gln Ile Arg Leu Met Tyr Val Pro Thr His Arg Ala
1               5                   10
```

<210> SEQ ID NO 806
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 806

```
Arg Arg Leu Trp Val Leu Asp Val Gly Gln Val Asp Tyr Lys Lys
1               5                   10                  15
```

<210> SEQ ID NO 807
<211> LENGTH: 14
<212> TYPE: PRT
<213> ORGANISM: Artificial Sequence
<220> FEATURE:

-continued

```
<223> OTHER INFORMATION: Description of Artificial Sequence; NOTE =
      Synthetic Construct

<400> SEQUENCE: 807

Arg Ala Ile Arg Asn Leu Pro Cys Glu Val Arg Lys Pro Lys
1               5                   10

<210> SEQ ID NO 808
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 808

Lys Asp Gly His Arg Pro Ala Tyr Tyr Ile Ala Gly Ser Ser Thr Lys
1               5                   10                  15

Val

<210> SEQ ID NO 809
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 809

Lys Gly Ala Ser Leu Lys Pro Arg Leu Leu Gly Glu Arg Gly Phe Lys
1               5                   10                  15

Thr

<210> SEQ ID NO 810
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 810

Arg Gln Val Ser Ala Trp Asn Ile Gln Lys Glu Leu Ile Pro Lys Asn
1               5                   10                  15

<210> SEQ ID NO 811
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 811

Arg Tyr Ser Asn Ile Pro Tyr Thr Leu Ala Glu Ile Asp Thr Arg Asn
1               5                   10                  15

<210> SEQ ID NO 812
<211> LENGTH: 15
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 812

Arg Phe Tyr Ala Trp Arg Asn Ile Thr Phe Glu Asp Val Lys Glu
```

```
<210> SEQ ID NO 813
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 813

Arg Asn Tyr Asn Arg Ser Glu Ile Arg Ser Pro Pro Phe Ser Lys Phe
1               5                   10                  15

<210> SEQ ID NO 814
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 814

Arg Arg Leu Trp Val Leu Asp Val Gly Gln Val Asp Tyr Lys Lys His
1               5                   10                  15

<210> SEQ ID NO 815
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 815

Arg Gln Ile Arg Leu Met Tyr Val Pro Thr His Arg Ala Ile Arg Asn
1               5                   10                  15

<210> SEQ ID NO 816
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 816

Arg Gly Phe Lys Thr Glu Ala Ile Ala Leu Ala Tyr Asp Pro Lys Thr
1               5                   10                  15

Lys Val

<210> SEQ ID NO 817
<211> LENGTH: 16
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 817

Lys Glu Phe Thr Ser Ile Tyr Gln Pro Val Ile Asp Asp Cys Arg Arg
1               5                   10                  15

<210> SEQ ID NO 818
<211> LENGTH: 17
<212> TYPE: PRT
<213> ORGANISM: Artificial Sequence
<220> FEATURE:
```

```
<223> OTHER INFORMATION: Description of Artificial Sequence; NOTE =
      Synthetic Construct

<400> SEQUENCE: 818

Arg Arg Tyr Ser Asn Ile Pro Tyr Thr Leu Ala Glu Ile Asp Thr Arg
 1               5                  10                  15
Asn

<210> SEQ ID NO 819
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 819

Arg Asn Lys Asp Gly His Arg Pro Ala Tyr Tyr Ile Ala Gly Ser Ser
 1               5                  10                  15
Thr Lys Val

<210> SEQ ID NO 820
<211> LENGTH: 18
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 820

Lys Asn Ala Trp Lys Phe Asn Asp Asp Ser Phe Lys Pro Glu Pro Gly
 1               5                  10                  15
Lys Ser

<210> SEQ ID NO 821
<211> LENGTH: 19
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 821

Arg Ser Glu Ile Arg Ser Pro Pro Phe Ser Lys Phe Asn Ser Gln Ser
 1               5                  10                  15
Gly Lys Glu

<210> SEQ ID NO 822
<211> LENGTH: 17
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 822

Lys Glu Phe Thr Ser Ile Tyr Gln Pro Val Ile Asp Asp Cys Arg Arg
 1               5                  10                  15
Leu

<210> SEQ ID NO 823
<211> LENGTH: 20
<212> TYPE: PRT
<213> ORGANISM: Artificial Sequence
<220> FEATURE:
```

-continued

<223> OTHER INFORMATION: Description of Artificial Sequence; NOTE = 
      Synthetic Construct

<400> SEQUENCE: 823

Lys Gly Glu Gln Tyr Ser Tyr Ile Ala Gly Ile Phe Gly Ile Thr Leu
1               5                   10                  15

Gly Asp Arg Asn
            20

<210> SEQ ID NO 824
<211> LENGTH: 21
<212> TYPE: PRT
<213> ORGANISM: Artificial Sequence
<220> FEATURE:
<223> OTHER INFORMATION: Description of Artificial Sequence; NOTE = 
      Synthetic Construct

<400> SEQUENCE: 824

Lys Glu Gly Thr Tyr Lys Pro Gly Asp Val Ile Pro Thr Gly Val Thr
1               5                   10                  15

His Asp Ala Lys Thr
            20

<210> SEQ ID NO 825
<211> LENGTH: 21
<212> TYPE: PRT
<213> ORGANISM: Artificial Sequence
<220> FEATURE:
<223> OTHER INFORMATION: Description of Artificial Sequence; NOTE = 
      Synthetic Construct

<400> SEQUENCE: 825

Lys Val Tyr Ser Val Asn Thr Ala Ser Leu Lys Glu Lys Gly Ala Ser
1               5                   10                  15

Leu Lys Pro Arg Leu
            20

<210> SEQ ID NO 826
<211> LENGTH: 21
<212> TYPE: PRT
<213> ORGANISM: Artificial Sequence
<220> FEATURE:
<223> OTHER INFORMATION: Description of Artificial Sequence; NOTE = 
      Synthetic Construct

<400> SEQUENCE: 826

Arg Leu Leu Gly Glu Arg Gly Phe Lys Thr Glu Ala Ile Ala Leu Ala
1               5                   10                  15

Tyr Asp Pro Lys Thr
            20

<210> SEQ ID NO 827
<211> LENGTH: 20
<212> TYPE: PRT
<213> ORGANISM: Artificial Sequence
<220> FEATURE:
<223> OTHER INFORMATION: Description of Artificial Sequence; NOTE = 
      Synthetic Construct

<400> SEQUENCE: 827

Lys Phe Asn Asp Asp Ser Phe Lys Pro Glu Pro Gly Lys Ser Val Phe
1               5                   10                  15

Asn His Lys Gly
            20

-continued

<210> SEQ ID NO 828
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 828

Lys Asn Lys Asn Ala Trp Lys Phe Asn Asp Asp Ser Phe Lys Pro Glu
1               5                   10                  15

Pro Gly Lys Ser
            20

<210> SEQ ID NO 829
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 829

Arg Ser Pro Leu Gly Phe Gly Gly Phe Ala Val Asp Val Ile Asn Pro
1               5                   10                  15

Asn Gly Asn Cys Ala Lys Ser
            20

<210> SEQ ID NO 830
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 830

Lys Asn Pro Glu Ile Ile Ala Phe Asp Leu Asn Gln Glu Gly Asn Pro
1               5                   10                  15

Glu Val His Arg Tyr
            20

<210> SEQ ID NO 831
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 831

Lys Gly Glu Gln Tyr Ser Tyr Ile Ala Gly Ile Phe Gly Ile Thr Leu
1               5                   10                  15

Gly Asp Arg Asn Lys Asp
            20

<210> SEQ ID NO 832
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 832

Arg Tyr Ser Asn Ile Pro Tyr Thr Leu Ala Glu Ile Asp Thr Arg Asn
1               5                   10                  15

Tyr Asn Arg Ser
            20

<210> SEQ ID NO 833
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 833

Lys Glu Gly Thr Tyr Lys Pro Gly Asp Val Ile Pro Thr Gly Val Thr
 1               5                  10                  15

His Asp Ala Lys Thr Lys Lys
            20

<210> SEQ ID NO 834
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 834

Arg Leu Met Tyr Val Pro Thr His Arg Ala Ile Arg Asn Leu Pro Cys
 1               5                  10                  15

Glu Val Arg Lys
            20

<210> SEQ ID NO 835
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 835

Lys Val Ile Phe Phe Val Glu Ser Asp Ser Arg Gln Val Ser Ala Trp
 1               5                  10                  15

Asn Ile Gln Lys Glu
            20

<210> SEQ ID NO 836
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 836

Lys Glu Gly Thr Tyr Lys Pro Gly Asp Val Ile Pro Thr Gly Val Thr
 1               5                  10                  15

His Asp Ala Lys Thr Lys Lys Leu
            20

<210> SEQ ID NO 837
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 837

Arg Arg Tyr Ser Asn Ile Pro Tyr Thr Leu Ala Glu Ile Asp Thr Arg
1               5                   10                  15
Asn Tyr Asn Arg Ser
            20

<210> SEQ ID NO 838
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 838

Lys Thr Lys Val Ile Phe Phe Val Glu Ser Asp Ser Arg Gln Val Ser
1               5                   10                  15
Ala Trp Asn Ile Gln Lys Glu
            20

<210> SEQ ID NO 839
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 839

Lys Asn Pro Glu Ile Ile Ala Phe Asp Leu Asn Gln Glu Gly Asn Pro
1               5                   10                  15
Glu Val His Arg Tyr Lys Leu
            20

<210> SEQ ID NO 840
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 840

Arg Leu Trp Val Leu Asp Val Gly Gln Val Asp Tyr Lys Lys His Gly
1               5                   10                  15
Asn Glu Tyr Pro Thr Lys Asn
            20

<210> SEQ ID NO 841
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 841

Lys Phe Asn Ser Gln Ser Gly Lys Glu Phe Thr Ser Ile Tyr Gln Pro
1               5                   10                  15
Val Ile Asp Asp Cys Arg Arg
            20

<210> SEQ ID NO 842
<211> LENGTH: 23

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 842

Lys Phe Phe Leu Ser Val Ile Ala Leu Ala Ser Phe Gln Tyr Val Phe
1               5                   10                  15

Cys Asp Asp Val Glu Arg Phe
            20

<210> SEQ ID NO 843
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 843

Lys Asn Ala Trp Lys Phe Asn Asp Asp Ser Phe Lys Pro Glu Pro Gly
1               5                   10                  15

Lys Ser Val Phe Asn His Lys Gly
            20

<210> SEQ ID NO 844
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 844

Lys Thr Glu Ala Ile Ala Leu Ala Tyr Asp Pro Lys Thr Lys Val Ile
1               5                   10                  15

Phe Phe Val Glu Ser Asp Ser Arg Gln
            20                  25

<210> SEQ ID NO 845
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 845

Lys Ser Asp Glu Thr Tyr Leu Tyr Ile Thr Asn Phe Ile Asp Asn Ala
1               5                   10                  15

Leu Ile Val Tyr Asp Met Lys Asn
            20

<210> SEQ ID NO 846
<211> LENGTH: 24
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 846

Lys Leu Tyr Phe Gly Val Pro Arg Arg Tyr Ser Asn Ile Pro Tyr Thr
1               5                   10                  15

Leu Ala Glu Ile Asp Thr Arg Asn
```

<210> SEQ ID NO 847
<211> LENGTH: 24
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 847

Lys Phe Asn Ser Gln Ser Gly Lys Glu Phe Thr Ser Ile Tyr Gln Pro
 1               5                  10                  15

Val Ile Asp Asp Cys Arg Arg Leu
            20

<210> SEQ ID NO 848
<211> LENGTH: 26
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 848

Lys Ser Val Phe Asn His Lys Gly Glu Gln Tyr Ser Tyr Ile Ala Gly
 1               5                  10                  15

Ile Phe Gly Ile Thr Leu Gly Asp Arg Asn
            20                  25

<210> SEQ ID NO 849
<211> LENGTH: 27
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 849

Lys Asp Gly His Arg Pro Ala Tyr Tyr Ile Ala Gly Ser Ser Thr Lys
 1               5                  10                  15

Val Tyr Ser Val Asn Thr Ala Ser Leu Lys Glu
            20                  25

<210> SEQ ID NO 850
<211> LENGTH: 24
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 850

Arg Tyr Ser Asn Ile Pro Tyr Thr Leu Ala Glu Ile Asp Thr Arg Asn
 1               5                  10                  15

Tyr Asn Arg Ser Glu Ile Arg Ser
            20

<210> SEQ ID NO 851
<211> LENGTH: 24
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 851

Met Lys Phe Phe Leu Ser Val Ile Ala Leu Ala Ser Phe Gln Tyr Val
1               5                   10                  15
Phe Cys Asp Asp Val Glu Arg Phe
            20

<210> SEQ ID NO 852
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 852

Lys Val Ile Phe Phe Val Glu Ser Asp Ser Arg Gln Val Ser Ala Trp
1               5                   10                  15
Asn Ile Gln Lys Glu Leu Ile Pro Lys Asn
            20                  25

<210> SEQ ID NO 853
<211> LENGTH: 26
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 853

Lys Ser Asp Glu Thr Tyr Leu Tyr Ile Thr Asn Phe Ile Asp Asn Ala
1               5                   10                  15
Leu Ile Val Tyr Asp Met Lys Asn Lys Asn
            20                  25

<210> SEQ ID NO 854
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 854

Lys Ser Val Phe Asn His Lys Gly Glu Gln Tyr Ser Tyr Ile Ala Gly
1               5                   10                  15
Ile Phe Gly Ile Thr Leu Gly Asp Arg Asn Lys Asp
            20                  25

<210> SEQ ID NO 855
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 855

Arg Asn Lys Asp Gly His Arg Pro Ala Tyr Tyr Ile Ala Gly Ser Ser
1               5                   10                  15
Thr Lys Val Tyr Ser Val Asn Thr Ala Ser Leu Lys Glu
            20                  25

<210> SEQ ID NO 856
<211> LENGTH: 29
<212> TYPE: PRT
<213> ORGANISM: Artificial Sequence

```
<220> FEATURE:
<223> OTHER INFORMATION: Description of Artificial Sequence; NOTE =
      Synthetic Construct

<400> SEQUENCE: 856

Arg Asn Ile Thr Phe Glu Asp Val Lys Glu Gly Thr Tyr Lys Pro Gly
1               5                   10                  15

Asp Val Ile Pro Thr Gly Val Thr His Asp Ala Lys Thr
            20                  25

<210> SEQ ID NO 857
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 857

Lys Asp Gly His Arg Pro Ala Tyr Tyr Ile Ala Gly Ser Ser Thr Lys
1               5                   10                  15

Val Tyr Ser Val Asn Thr Ala Ser Leu Lys Glu Lys Gly
            20                  25

<210> SEQ ID NO 858
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 858

Lys His Gly Asn Glu Tyr Pro Thr Lys Asn Pro Glu Ile Ile Ala Phe
1               5                   10                  15

Asp Leu Asn Gln Glu Gly Asn Pro Glu Val His Arg Tyr
            20                  25

<210> SEQ ID NO 859
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 859

Arg Ser Pro Pro Phe Ser Lys Phe Asn Ser Gln Ser Gly Lys Glu Phe
1               5                   10                  15

Thr Ser Ile Tyr Gln Pro Val Ile Asp Asp Cys Arg Arg
            20                  25

<210> SEQ ID NO 860
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 860

Arg Asn Ile Thr Phe Glu Asp Val Lys Glu Gly Thr Tyr Lys Pro Gly
1               5                   10                  15

Asp Val Ile Pro Thr Gly Val Thr His Asp Ala Lys Thr Lys Lys
            20                  25                  30
```

```
<210> SEQ ID NO 861
<211> LENGTH: 32
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 861

Arg Tyr Lys Leu Glu Gly Asp Val Ala Arg Ser Pro Leu Gly Phe Gly
 1               5                  10                  15

Gly Phe Ala Val Asp Val Ile Asn Pro Asn Gly Asn Cys Ala Lys Ser
            20                  25                  30

<210> SEQ ID NO 862
<211> LENGTH: 30
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 862

Lys Asn Pro Glu Ile Ile Ala Phe Asp Leu Asn Gln Glu Gly Asn Pro
 1               5                  10                  15

Glu Val His Arg Tyr Lys Leu Glu Gly Asp Val Ala Arg Ser
            20                  25                  30

<210> SEQ ID NO 863
<211> LENGTH: 30
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 863

Lys Lys His Gly Asn Glu Tyr Pro Thr Lys Asn Pro Glu Ile Ile Ala
 1               5                  10                  15

Phe Asp Leu Asn Gln Glu Gly Asn Pro Glu Val His Arg Tyr
            20                  25                  30

<210> SEQ ID NO 864
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 864

Lys Phe Phe Leu Ser Val Ile Ala Leu Ala Ser Phe Gln Tyr Val Phe
 1               5                  10                  15

Cys Asp Asp Val Glu Arg Phe Tyr Ala Trp Arg Asn
            20                  25

<210> SEQ ID NO 865
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 865

Lys Glu Phe Thr Ser Ile Tyr Gln Pro Val Ile Asp Asp Cys Arg Arg
```

```
                1               5                  10                 15
Leu Trp Val Leu Asp Val Gly Gln Val Asp Tyr Lys Lys
            20                  25

<210> SEQ ID NO 866
<211> LENGTH: 30
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 866

Lys Ser Asp Glu Thr Tyr Leu Tyr Ile Thr Asn Phe Ile Asp Asn Ala
1               5                  10                 15
Leu Ile Val Tyr Asp Met Lys Asn Lys Asn Ala Trp Lys Phe
            20                  25                  30

<210> SEQ ID NO 867
<211> LENGTH: 31
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 867

Lys His Gly Asn Glu Tyr Pro Thr Lys Asn Pro Glu Ile Ile Ala Phe
1               5                  10                 15
Asp Leu Asn Gln Glu Gly Asn Pro Glu Val His Arg Tyr Lys Leu
            20                  25                  30

<210> SEQ ID NO 868
<211> LENGTH: 28
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 868

Lys Phe Phe Leu Ser Val Ile Ala Leu Ala Ser Phe Gln Tyr Val Phe
1               5                  10                 15
Cys Asp Asp Val Glu Arg Phe Tyr Ala Trp Arg Asn
            20                  25

<210> SEQ ID NO 869
<211> LENGTH: 29
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 869

Met Lys Phe Phe Leu Ser Val Ile Ala Leu Ala Ser Phe Gln Tyr Val
1               5                  10                 15
Phe Cys Asp Asp Val Glu Arg Phe Tyr Ala Trp Arg Asn
            20                  25

<210> SEQ ID NO 870
<211> LENGTH: 37
<212> TYPE: PRT
<213> ORGANISM: Artificial Sequence
<220> FEATURE:
<223> OTHER INFORMATION: Description of Artificial Sequence; NOTE =
```

-continued

Synthetic Construct

<400> SEQUENCE: 870

Lys Gly Glu Gln Tyr Ser Tyr Ile Ala Gly Ile Phe Gly Ile Thr Leu
1               5                   10                  15

Gly Asp Arg Asn Lys Asp Gly His Arg Pro Ala Tyr Tyr Ile Ala Gly
            20                  25                  30

Ser Ser Thr Lys Val
        35

<210> SEQ ID NO 871
<211> LENGTH: 38
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 871

Lys Phe Asn Asp Asp Ser Phe Lys Pro Glu Pro Gly Lys Ser Val Phe
1               5                   10                  15

Asn His Lys Gly Glu Gln Tyr Ser Tyr Ile Ala Gly Ile Phe Gly Ile
            20                  25                  30

Thr Leu Gly Asp Arg Asn
        35

<210> SEQ ID NO 872
<211> LENGTH: 36
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 872

Lys Phe Phe Leu Ser Val Ile Ala Leu Ala Ser Phe Gln Tyr Val Phe
1               5                   10                  15

Cys Asp Asp Val Glu Arg Phe Tyr Ala Trp Arg Asn Ile Thr Phe Glu
            20                  25                  30

Asp Val Lys Glu
        35

<210> SEQ ID NO 873
<211> LENGTH: 41
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 873

Lys Asn Val Gly Val Ile Tyr Thr Asn Ala Tyr Phe Val Phe Gly Thr
1               5                   10                  15

Asp Ile Met Val Asp Ala Asp Ser Thr Leu Trp Phe Met Ser Asn Ala
            20                  25                  30

His Pro Pro Thr Glu Leu Pro Lys Leu
        35                  40

<210> SEQ ID NO 874
<211> LENGTH: 46
<212> TYPE: PRT
<213> ORGANISM: Artificial Sequence
<220> FEATURE:
<223> OTHER INFORMATION: Description of Artificial Sequence; NOTE =

-continued

Synthetic Construct

<400> SEQUENCE: 874

Lys Glu Leu Ile Pro Lys Asn Val Gly Val Ile Tyr Thr Asn Ala Tyr
1               5                   10                  15

Phe Val Phe Gly Thr Asp Ile Met Val Asp Ala Asp Ser Thr Leu Trp
            20                  25                  30

Phe Met Ser Asn Ala His Pro Pro Thr Glu Leu Pro Lys Leu
        35                  40                  45

<210> SEQ ID NO 875
<211> LENGTH: 46
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 875

Lys Asn Val Gly Val Ile Tyr Thr Asn Ala Tyr Phe Val Phe Gly Thr
1               5                   10                  15

Asp Ile Met Val Asp Ala Asp Ser Thr Leu Trp Phe Met Ser Asn Ala
            20                  25                  30

His Pro Pro Thr Glu Leu Pro Lys Leu Asp Phe Asp Lys Arg
        35                  40                  45

<210> SEQ ID NO 876
<211> LENGTH: 47
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 876

Arg Ser Pro Leu Gly Phe Gly Gly Phe Ala Val Asp Val Ile Asn Pro
1               5                   10                  15

Asn Gly Asn Cys Ala Lys Ser Asp Glu Thr Tyr Leu Tyr Ile Thr Asn
            20                  25                  30

Phe Ile Asp Asn Ala Leu Ile Val Tyr Asp Met Lys Asn Lys Asn
        35                  40                  45

<210> SEQ ID NO 877
<211> LENGTH: 47
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 877

Lys Asn Val Gly Val Ile Tyr Thr Asn Ala Tyr Phe Val Phe Gly Thr
1               5                   10                  15

Asp Ile Met Val Asp Ala Asp Ser Thr Leu Trp Phe Met Ser Asn Ala
            20                  25                  30

His Pro Pro Thr Glu Leu Pro Lys Leu Asp Phe Asp Lys Arg Gln
        35                  40                  45

<210> SEQ ID NO 878
<211> LENGTH: 52
<212> TYPE: PRT
<213> ORGANISM: Artificial Sequence
<220> FEATURE:
<223> OTHER INFORMATION: Description of Artificial Sequence; NOTE =

Synthetic Construct

<400> SEQUENCE: 878

Lys Leu Glu Gly Asp Val Ala Arg Ser Pro Leu Gly Phe Gly Gly Phe
1               5                   10                  15

Ala Val Asp Val Ile Asn Pro Asn Gly Asn Cys Ala Lys Ser Asp Glu
            20                  25                  30

Thr Tyr Leu Tyr Ile Thr Asn Phe Ile Asp Asn Ala Leu Ile Val Tyr
        35                  40                  45

Asp Met Lys Asn
    50

<210> SEQ ID NO 879
<211> LENGTH: 51
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 879

Lys Glu Leu Ile Pro Lys Asn Val Gly Val Ile Tyr Thr Asn Ala Tyr
1               5                   10                  15

Phe Val Phe Gly Thr Asp Ile Met Val Asp Ala Asp Ser Thr Leu Trp
            20                  25                  30

Phe Met Ser Asn Ala His Pro Pro Thr Glu Leu Pro Lys Leu Asp Phe
        35                  40                  45

Asp Lys Arg
    50

<210> SEQ ID NO 880
<211> LENGTH: 55
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 880

Arg Gln Val Ser Ala Trp Asn Ile Gln Lys Glu Leu Ile Pro Lys Asn
1               5                   10                  15

Val Gly Val Ile Tyr Thr Asn Ala Tyr Phe Val Phe Gly Thr Asp Ile
            20                  25                  30

Met Val Asp Ala Asp Ser Thr Leu Trp Phe Met Ser Asn Ala His Pro
        35                  40                  45

Pro Thr Glu Leu Pro Lys Leu
    50                  55

<210> SEQ ID NO 881
<211> LENGTH: 22
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 881
aagtactcta gcaattgtga gc                                            22

<210> SEQ ID NO 882
<211> LENGTH: 22
<212> TYPE: DNA
<213> ORGANISM: Artificial Sequence

```
<220> FEATURE:
<223> OTHER INFORMATION: Description of Artificial Sequence; NOTE =
      Synthetic Construct

<400> SEQUENCE: 882
ctcttcgcta ttacgccagc tg                                            22

<210> SEQ ID NO 883
<211> LENGTH: 27
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 883
tgcggatccg aaaatccatc aaagaag                                       27

<210> SEQ ID NO 884
<211> LENGTH: 27
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 884
attggatcct tatatattga ttgtttt                                       27
```